United States Patent
Peretz et al.

(10) Patent No.: US 7,834,144 B2
(45) Date of Patent: Nov. 16, 2010

(54) PRION-SPECIFIC PEPTOID REAGENTS

(75) Inventors: David Peretz, El Cerrito, CA (US);
Michael D. Connolly, Dublin, CA (US);
Ronald Zuckermann, El Cerrito, CA (US); Man Gao, San Ramon, CA (US);
Gulliver Timoteo, Hayward, CA (US);
Robert M. Shimizu, Petaluma, CA (US)

(73) Assignee: Novartis AG, Basel (CH)

( * ) Notice: Subject to any disclaimer, the term of this patent is extended or adjusted under 35 U.S.C. 154(b) by 583 days.

(21) Appl. No.: 11/518,091

(22) Filed: Sep. 8, 2006

(65) Prior Publication Data

US 2007/0087972 A1    Apr. 19, 2007

Related U.S. Application Data

(60) Provisional application No. 60/715,761, filed on Sep. 9, 2005, provisional application No. 60/726,686, filed on Oct. 14, 2005, provisional application No. 60/758,934, filed on Jan. 13, 2006.

(51) Int. Cl.
*C07K 7/00* (2006.01)
(52) U.S. Cl. .................. 530/328; 514/2; 530/326; 530/327; 530/329; 530/330; 530/345
(58) Field of Classification Search .......... 514/2; 530/326, 327, 328, 329, 330, 345
See application file for complete search history.

(56) References Cited

U.S. PATENT DOCUMENTS

| | | | |
|---|---|---|---|
| 5,422,425 A | 6/1995 | Kriegler et al. | |
| 6,075,121 A | 6/2000 | Simon et al. | |
| 6,211,149 B1 | 4/2001 | Chesebro et al. | |
| 6,251,433 B1 | 6/2001 | Zuckermann et al. | |
| 6,372,214 B1 | 4/2002 | Prusiner et al. | |
| 6,462,171 B1 | 10/2002 | Soto-Jara et al. | |
| 6,656,716 B1 | 12/2003 | Plowman et al. | |
| 6,680,170 B2 | 1/2004 | Plowman et al. | |
| 6,765,088 B1 | 7/2004 | Korth et al. | |
| 6,787,319 B2 | 9/2004 | Ozenberger et al. | |
| 7,005,295 B1 | 2/2006 | Ozenberger et al. | |
| 7,097,997 B1 | 8/2006 | Deslys et al. | |
| 7,101,973 B2 | 9/2006 | Ozenberger et al. | |
| 7,166,471 B2 | 1/2007 | Orser et al. | |
| 7,435,540 B2 | 10/2008 | Cashman et al. | |
| 7,479,482 B2 | 1/2009 | Frangione et al. | |
| 7,482,172 B2 | 1/2009 | Zheng | |
| 2003/0040468 A1 | 2/2003 | Barron et al. | |
| 2003/0092613 A1 | 5/2003 | Lee et al. | |
| 2003/0215880 A1 | 11/2003 | Burton et al. | |
| 2004/0009167 A1* | 1/2004 | Rider | 424/132.1 |
| 2004/0052928 A1 | 3/2004 | Gazit | |
| 2004/0072236 A1 | 4/2004 | Cashman et al. | |
| 2004/0186273 A1 | 9/2004 | Hammond et al. | |
| 2004/0208919 A1 | 10/2004 | Nicolau et al. | |
| 2004/0229280 A1 | 11/2004 | Hammond et al. | |
| 2005/0014196 A1 | 1/2005 | Carbonell et al. | |
| 2005/0026165 A1 | 2/2005 | Orser et al. | |
| 2005/0100962 A1 | 5/2005 | van Oers et al. | |
| 2005/0118645 A1 | 6/2005 | Michelitsch et al. | |
| 2006/0035242 A1 | 2/2006 | Michelitsch et al. | |
| 2006/0057671 A1 | 3/2006 | Orser et al. | |
| 2006/0094071 A1 | 5/2006 | Engenann et al. | |
| 2006/0235199 A1 | 10/2006 | Mihara et al. | |
| 2006/0248605 A1 | 11/2006 | Ozenberger et al. | |
| 2006/0275910 A1 | 12/2006 | Orser et al. | |
| 2006/0286672 A1 | 12/2006 | Orser et al. | |
| 2007/0093415 A1 | 4/2007 | Martin | |
| 2008/0171341 A1 | 7/2008 | Orser et al. | |
| 2009/0099343 A1 | 4/2009 | Peretz et al. | |
| 2009/0130774 A1 | 5/2009 | Peretz et al. | |

FOREIGN PATENT DOCUMENTS

| | | |
|---|---|---|
| DE | 19741607 | 3/1999 |
| EP | 0909388 | 4/1999 |
| EP | 1382971 | 1/2004 |
| EP | 1457500 | 9/2004 |
| EP | 1643252 A2 | 4/2006 |
| WO | WO-93/11155 | 6/1993 |
| WO | WO-93/23432 | 11/1993 |
| WO | WO94/06451 | 3/1994 |
| WO | WO-94/06451 | 3/1994 |
| WO | WO-97/16728 | 5/1997 |
| WO | WO-99/15651 | 4/1999 |
| WO | WO-00/29849 | 5/2000 |
| WO | WO-00/43791 | 7/2000 |
| WO | WO-00/78344 | 12/2000 |
| WO | WO-01/07479 | 2/2001 |
| WO | WO-01/23425 | 4/2001 |
| WO | WO-01/35104 | 5/2001 |
| WO | WO-01/77687 | 10/2001 |
| WO | WO-01/97785 | 12/2001 |
| WO | WO-02/04954 | 1/2002 |
| WO | WO-02/14351 | 2/2002 |

(Continued)

OTHER PUBLICATIONS

Alluri (J Am Chem Soc 125, 13995-14004 2003).*

(Continued)

*Primary Examiner*—David Lukton
(74) *Attorney, Agent, or Firm*—Mei Hong; Patricia Tsao

(57) ABSTRACT

The invention relates to peptoid reagents that interact preferentially with a pathogenic form of a conformational disease protein as compared to a nonpathogenic form of the conformational disease protein where the peptoid reagent comprises an amino-terminal region, a carboxy-terminal region, and at least one peptoid region between the amino-terminal region and the carboxy-terminal region where the peptoid region comprises 3 to about 30 N-substituted glycines, and optionally one or more amino acids. The invention also relates to methods of using the peptoids in detecting and isolating prions, and in the treatment and prevention of prion-related diseases.

50 Claims, 4 Drawing Sheets

FOREIGN PATENT DOCUMENTS

| WO | WO-02/052046 | 7/2002 |
|---|---|---|
| WO | WO02052046 | 7/2002 |
| WO | WO-02/065134 | 8/2002 |
| WO | WO-02/097444 | 12/2002 |
| WO | WO-03/045128 | 6/2003 |
| WO | WO-03/050139 | 6/2003 |
| WO | WO 03/073106 | 9/2003 |
| WO | WO-03/085086 | 10/2003 |
| WO | WO-2004/005920 | 1/2004 |
| WO | WO-2004/018511 | 3/2004 |
| WO | WO-2004/029072 | 4/2004 |
| WO | WO-2004/037854 | 5/2004 |
| WO | WO-2004/046728 | 6/2004 |
| WO | WO-2004/050851 | 6/2004 |
| WO | WO-2004/090102 | 10/2004 |
| WO | WO-2004/091523 | 10/2004 |
| WO | WO-2004/092197 | 10/2004 |
| WO | WO-2005/016127 | 2/2005 |
| WO | WO-2005/016957 | 2/2005 |
| WO | WO2005016127 | 2/2005 |
| WO | WO-2005/057166 | 6/2005 |
| WO | WO-2005/060697 | 7/2005 |
| WO | WO2005060697 | 7/2005 |
| WO | WO-2005/075507 | 8/2005 |
| WO | WO-2006/026977 | 3/2006 |
| WO | WO 2006/076687 | 7/2006 |
| WO | WO-2006/087550 | 8/2006 |
| WO | WO-2006/088823 | 8/2006 |
| WO | WO-2007/030804 | 3/2007 |
| WO | WO-2007/145589 | 12/2007 |
| WO | WO-2008/013859 | 1/2008 |
| WO | WO-2008/134034 | 11/2008 |

OTHER PUBLICATIONS

Wender (Proc Natl Acad Sci 97(24), 13003-13008, 2000).*
Kodadek, Thomas (Molecular BioSystems 2(1), 25-35, 2006).*
Reddy et al., "Transformation of Low-Affinity Lead Compounds into High-Affinity Protein Capture Agents", Chemistry & Biology, vol. 11(8), pp. 1127-1137.
Firer, M A. (Oct. 30, 2001). "Efficient elution of functional proteins in affinity chromatography," *Journal Of Biochemical And Biophysical Methods* 49:433-442.
Fischer, M. B. et al. (Nov. 23, 2000). "Binding of disease-associated prion protein to plasminogen," *Nature* 408(6811):479-483.
Gasset, M. et al. (1992). "Predicted .alpha.-Helical Regions of the Prion Protein When Synthesized as Peptides Form Amyloid," *Proc. Natl. Acad. Sci. USA* 89:10940-10944.
Gasset, M. et al. (1993). "Perturbation of the secondary structure of the scrapie prion protein under conditions that alter infectivity," *Proc. Natl. Acad. Sci. USA* 90(1):1-5.
Gauczynski, E. et al. (2001). "Interaction of Prion Proteins With Cell Surface Receptors, Molecular Chaperones, and Other Molecules," *Advances In Protein Chemistry* 57:229-272.
Georgieva, (2002). "Prion diseases. Antibody-mediated prion prevention," *Experimental Pathology and Parasitology* p. 60-63.
Gorske et al. (Apr. 14, 2005). "Expedient synthesis and design strategies for new peptoid construction," *Organic Letters* 7(8):1521-1524.
Haynes et al. (Jul. 4, 2005). "Comblike, monodisperse polypeptoid drag-tags for DNA separations by end-labeled free-solution elecrtophoresis (ELPSE)," *Bioconjugate Chemistry* 16(4):929-938.
Huang et al. (Jun. 1998). "Lipitoids—novel cationic lipids for cellular delivery of plasmid DNA in vitro," *Chemistry and Biology* 5(6):345-354.
Ingrosso, L. et al. (Jun. 2002). "Molecular Diagnostics of Transmissible Spongiform Encephalopathies," *Trends in Molecular Medicine* 8(6):273-280.
International Search Report and Written Opinion mailed Aug. 5, 2009, for PCT Application No. PCT/US2009/042185 filed on Apr. 29, 2009, 15 pages.
International Search Report mailed Feb. 13, 2007, for PCT Application No. PCT/US2006/035226 filed Sep. 8, 2006, 1 page.
International Search Report mailed Jan. 8, 2007, for PCT Application No. PCT/US2006/001433 filed Jan. 13, 2006, 1 page.
International Search Report mailed Oct. 3, 2007, for PCT Application No. PCT/US2006/001437 filed Jan. 13, 2006, 2 pages.
International Search Report mailed Sep. 24, 2007, for PCT Application No. PCT/US2006/001090 filed Jan. 13, 2006, 2 pages.
Irani et al. (2003). "Diagnosis and prevention of bovine spongiform encephalopathy and variant Creutzfeldt-Jakob disease," *Annual Review of Medicine* 54:305-319.
Ironside, J. W. et al. (2002). "Pathological Diagnosis of Variant Creutzfeldt-Jakob Disease," *APMIS* 110:79-87.
Kirshenbaum et al. (Apr. 14, 1998). "Sequence-specific polypeptoids: A diverse family of heteropolymers with stable secondary structure," *Proc. Natl. Acad. Sci. USA* 95(8):4303-4308.
Koller et al. (2002). "Induction of antibodies against murine full-length prion protein in wild-type mice," *Journal of Neuroimmunology* 132:113-116.
Lau, A L et al. (Jul. 10, 2007). "Characterization of prion protein (PrP)-derived peptides that discriminate full-length PrP from PrP," *Proc. Natl. Acad. Sci. USA* 104(28):11551-11556.
Lee et al. (1996). "Crystal structure of the conserved core of HIV-1 Nef complexed with a Src family SH3 domain," *Cell* 85:931-942.
Lee et al. (1997). "Simulation of pH elution in high-performance affinity chromatography using non-porous adsorbents," *Chemical Engineering Journal* 65:175-186.
Lundberg, P. et al. (Nov. 22, 2002). "Cell Membrane Translocation of the N-Terminal (1-28) Part of the Prion Protein," *Biochemical and Biophysical Research Communications* 299(1):85-90.
McLeod A H et al (May 14, 2004). "Proteolytic inactivation of the bovine spongiform encephalopathy agent" *Biochemical and Biophysical Research Communications* 317(4):1165-1170.
Meier, P et al: (Apr. 4, 2003). "Soluble dimeric prion protein binds PrP(Sc) in vivo and antagonizes prion disease," *Cell* 113(1):49-60.
Monari, L. et al. (1994). "Fatal familial insomnia and familial Creutzfeldt-Jakob disease: Different prion proteins determined by a DNA polymorphism" *Proc Natl Acad Sci* 91:2839-2842.
Morel, N. et al. (Jul. 16, 2004). "Selective and efficient immunoprecipitation of the disease-associated form of the prion protein can be mediated by nonspecific interactions between monoclonal antibodies and scrapie-associated fibrils," *J Biol Chem* 279(29):30143-30149.
Moroncini, G et al. (Jul. 13, 2004). "Motif-grafted antibodies containing the replicative interface of cellular PrP are specific for PrPSc." *Proc. Natl. Acad. Sci. USA* 101(28):10404-10409.
Nguyen et al. (1995). "Prion Protein Peptides Induce .alpha.-Helix to .beta.-Sheet Conformational Transitions," *Biochemistry* 34:4186-4192.
Pan, T. et al. (2002). "Cell-Surface Prion Protein Interacts with Glycosaminoglycans," *Biochemical Journal* 368:81-90.
Peretz et al. (1997). "A Conformational Transition at the N Terminus of the Prion Protein Features in Formation of the Scrapie Isoform," *Journal of Molecular Biology* 273:614-622.
Peretz et al., (2001). "Antibodies Inhibit Prion Propagation and Clear Cell Cultures of Prion Infectivity," *Nature* 412:739-743.
Pierce Biotechnology, Inc. (Nov. 2004). "Optimize elution conditions for immunoaffinity purification" Technical Resource, No. TR0027.0.
Priola, (2001). "Prion Protein Diversity and Disease in the Transmissible Spongiform Encephalopathies," *Advances in Protein Chemistry* 57:1-27.
Ryou et al., (2003). "Differential Inhibition of Prion Propagation by Enantiomers of Quinacrine," *Laboratory Investigation* 83:837-843.
Safar et al. (2002). "Measuring Prions Causing Bovine Spongiform Encephalopathy or Chronic Wasting Disease by Immunoassays and Transgenic Mice," *Nature Biotechnology* 20:1147-1150.
Tagliavini et al. (2001). "Studies on Peptide Fragments of Prion Proteins," *Advances in Protein Chemistry* 57:171-201.
Tagliavini et al., (1993). "Synthetic Peptides Homologous to Prion Protein Residues 106-147 Form Amyloid-Like Fibrils in vitro," *Proc. Natl. Acad. Sci. USA* 90:9678-9682.
Tcherkasskaya, O. et al. (2003). "The Role of Hydrophobic Interactions in Amyloidogenesis: Example of Prion-Related Polypeptides," *Journal of Biomolecular Structure & Dynamics* 21(3):353-365.

United States Office Action mailed Apr. 13, 2007, for U.S. Appl. No. 11/056,950, filed Feb. 11, 2005, 10 pages.
United States Office Action mailed Dec. 31, 2007, for U.S. Appl. No. 11/056,950, filed Feb. 11, 2005, 9 pages.
United States Office Action mailed Feb. 3, 2010, for U.S. Appl. No. 12/079,573, filed Mar. 27, 2008, 7 pages.
United States Office Action mailed May 14, 2007, for U.S. Appl. No. 10/917,646, filed Aug. 13, 2004, 10 pages.
United States Office Action mailed Nov. 14, 2006, for U.S. Appl. No. 10/917,646, filed Aug. 13, 2004, 17 pages.
U.S. Appl. No. 11/795,164, filed Jan. 13, 2006 for Chien et al.
Williamson et al., (1998). "Mapping the Prion Protein Using Recombinant Antibodies" *Journal of Virology* 72:9413-9418.
Yehiely, F. et al. (Jan. 1, 1997). "Identification of Candidate Proteins Binding to Prion Protein," *Neurobiology of Disease* 3(4):339-355.
Gorske et al., "Expedient Synthesis and Design Strategies for New Peptoid Construction", Organic Letters, vol. 7, No. 8, Apr. 14, 2005, pp. 1521-1524.
Haynes et al., "Comblike, Monodisperse Polypeptoid Drag-Tags for DNA Separations by End-Labeled Free-Solution Electrophoresis (ELFSE)", Bioconjugate Chemistry, vol. 16, No. 4, Jul. 4, 2005, pp. 929-938.
Huang et al., "Lipitoids—novel cationic lipids for cellular delivery of plasmid DNA in vitro", Chemistry & Biology, vol. 5, No. 6, Jun. 1998, pp. 345-354.
Kirshenbaum et al., "Sequence-specific polypeptoids: A diverse family of heteropolymers with stable secondary structure", Proc. Natl. Acad. Sci., vol. 95, No. 8, Apr. 14, 1998, pp. 4303-4308.
Reddy et al., "Transformation of Low-Affinity Lead Compounds into High-Affinity Protein Capture Agents", Chemistry & Biology, vol. 11(8), pp. 1127-1137, 2004.
Bienkiewicz et al. (2000). "Conformation of the RNA polymerase II C-terminal domain: circular dichroism of long and short fragments," *Journal of Molecular Biology* 297:119-133.
Clarke, N. J. et al. (Jul. 3, 1998). "Detection and quantitation of cellularly derived amyloid beta peptides by immunoprecipitation-HPLC-MS," *FEBS Letters* 430(3):419-423.
Coulthart et al. (2001). "Variant Creutzfeldt-Jakob disease: a summary of current scientific knowledge in relation to public health," *CMAJ* 165:51-58.
European Search Report mailed Apr. 7, 2009, for EP Application No. 06718190.9, filed Aug. 13, 2007.
European Search Report mailed Oct. 9, 2008, for EP Application No. 06718499.4, filed Jan. 13, 2006.
European Search Report mailed Mar. 4, 2010, for EP Application No. 06718499.4, filed Jan. 13, 2006.
Bonomo et al. (2000). "Copper(II) Binding Modes in the Prion Octapeptide PHGGGWGQ: A Spectroscopic and Voltammetric Study," *Chem. Eur. J.* 6(22):4195-4202.
Gilch et al. (2003). "Polyclonal Anti-PrP Auto-antibodies Induced with Dimeric PrP Interfere Efficiently with PrPSc Propagation in Prion-infected Cells," *The Journal of Biological Chemistry* 278(20):18524-18531.
United States Office Action mailed Feb. 3, 2010, for U.S. Appl. No. 12/079,573 filed Mar. 27, 2008, 8 pages.

\* cited by examiner

Fig. 1A Detection of $PrP^C$ in normal human plasma
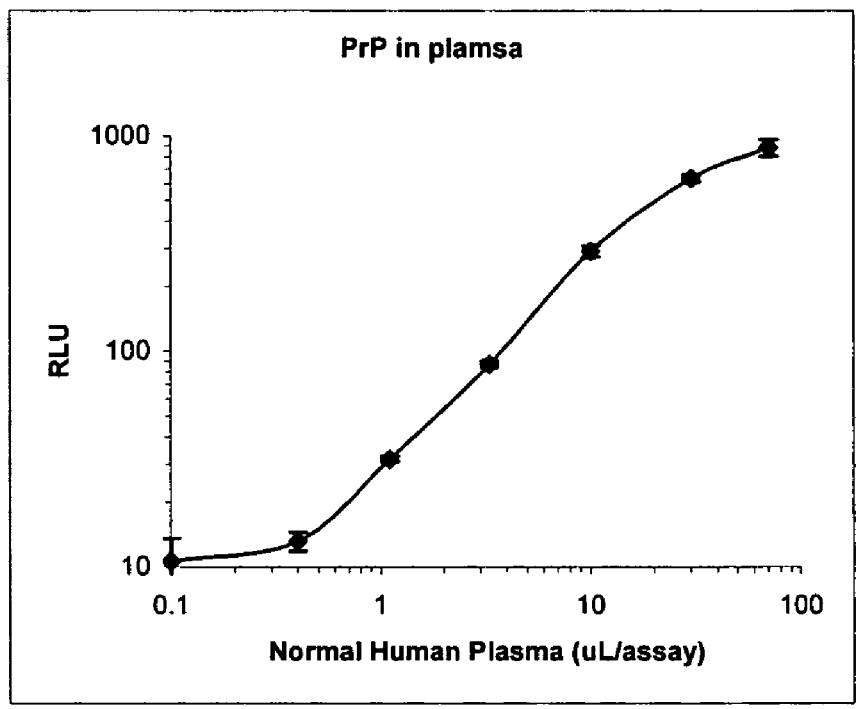
Fig. 1B Detection of human recombinant PrP
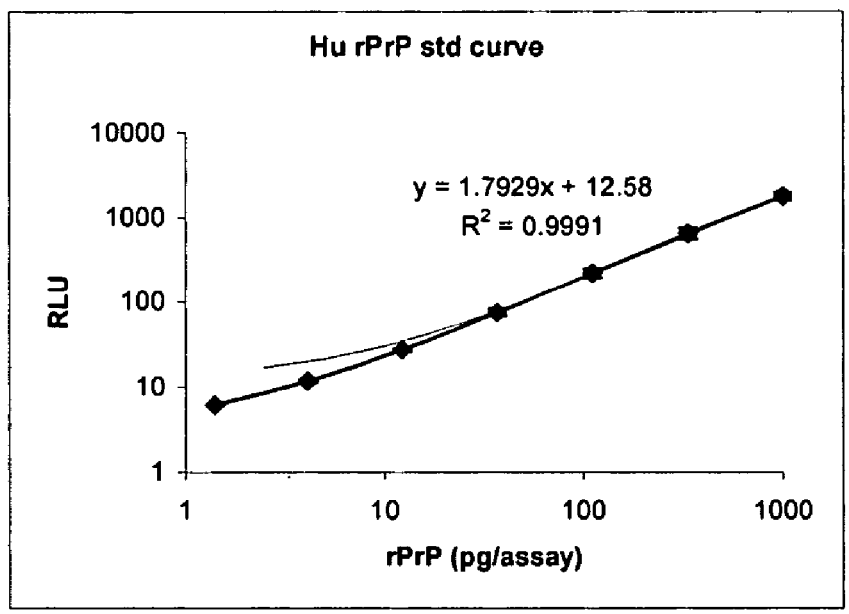

FIGURE 2

PRION AMINO ACID SEQUENCES

Amino Acid Sequence of a Full Length Human Prion Protein:

SEQ ID NO. 1: M A N L G C W M L V L F V A T W S D L G L C K K
R P K P G G W N T G G S R Y P G Q G S P G G N R Y P P Q G G G G
W G Q P H G G G W G Q P H G G G W G Q P H G G G W G Q P H G
G G W G Q G G G T H S Q W N K P S K P K T N M K H M A G A A
A A G A V V G G L G G Y M L G S A M S R P I I H F G S D Y E D R
Y Y R E N M H R Y P N Q V Y Y R P M D E Y S N Q N N F V H D C
V N I T I K Q H T V T T T T K G E N F T E T D V K M M E R V V E
Q M C I T Q Y E R E S Q A Y Y Q R G S S M V L F S S P P V I L L I S
F L I F L I V G

Amino Acid Sequence of a Full Length Mouse Prion Protein:

SEQ ID. NO. 2: M A N L G Y W L L A L F V T M W T D V G L C K
K R P K P G G W N T G G S R Y P G Q G S P G G N R Y P P Q G G T
W G Q P H G G G W G Q P H G G S W G Q P H G G S W G Q P H G
G G W G Q G G G T H N Q W N K P S K P K T N L K H V A G A A A
A G A V V G G L G G Y M L G S A M S R P M I H F G N D W E D R
Y Y R E N M Y R Y P N Q V Y Y R P V D Q Y S N Q N N F V H D C
V N I T I K Q H T V T T T T K G E N F T E T D V K M M E R V V E
Q M C V T Q Y Q K E S Q A Y Y D G R R S S S T V L F S S P P V I L
L I S F L I F L I V G

FIGURE 3

```
Human     --MANLGCWMLVLFVATWSDLGLCKKRPKPGG-WNTGGSRYPGQGSPGGNRYPPQGGGGW
Hamster   --MANLSYWLLALFVAMWTDVGLCKKRPKPGG-WNTGGSRYPGQGSPGGNRYPPQGGGTW
Bovine    MVKSHIGSWILVLFVAMWSDVGLCKKRPKPGGGWNTGGSRYPGQGXPGGNRYPPQGGGGW
Sheep     MVKSHIGSWILVLFVAMWSDVGLCKKRPKPGGGWNTGGSRYPGQGSPGGNRYPPQGGGGW
Mouse     --MANLGYWLLALFVTMWTDVGLCKKRPKPGG-WNTGGSRYPGQGSPGGNRYPPQGG-TW
Elk       MVKSHIGSWILVLFVAMWSDVGLCKKRPKPGGGWNTGGSRYPGQGSPGGNRYPPQGGGGW
Fallow    MVKSHIGSWILVLFVAMWSDVGLCKKRPKPGGGWNTGGSRYPGQGSPGGNRYPPQGGGGW
Mule      MVKSHIGSWILVLFVAMWSDVGLCKKRPKPGGGWNTGGSRYPGQGSPGGNRYPPQGGGGW
White     MVKSHIGSWILVLFVAMWSDVGLCKKRPKPGGGWNTGGSRYPGQGSPGGNRYPPQGGGGW
          :::. *:*.***: *:*:************  *************  *********** *

Human     GQPHGGGWGQPHGGGWGQPHGG--------GWGQPHGGG-WGQGGGTHSQWNKPSKPKTN
Hamster   GQPHGGGWGQPHGGGWGQPHGG--------GWGQPHGGG-WGQGGGTHNQWNKPSKPKTN
Bovine    GQPHGGGWGQPHGGGWGQPHGGGWGQPHGGGWGQGG-THGQWNKPSKPKTN
Sheep     GQPHGGGWGQPHGGGWGQPHGG--------GWGQPHGGGGWGQGG-SHSQWNKPSKPKTN
Mouse     GQPHGGGWGQPHGGSWGQPHGG--------SWGQPHGGG-WGQGGGTHNQWNKPSKPKTN
Elk       GQPHGGGWGQPHGGGWGQPHGG--------GWGQPHGGGGWGQGG-THSQWNKPSKPKTN
Fallow    GQPHGGGWGQPHGGGWGQPHGG--------GWGQPHGGGGWGQGG-THSQWNKPSKPKTN
Mule      GQPHGGGWGQPHGGGWGQPHGG--------GWGQPHGGGGWGQGG-THSQWNKPSKPKTN
White     GQPHGGGWGQPHGGGWGQPHGG--------GWGQPHGGGGWGQGG-THSQWNKPSKPKTN
          **************.*******        .******* **** :*.***********

Human     MKHMAGAAAAGAVVGGLGGYMLGSAMSRPIIHFGSDYEDRYYRENMHRYPNQVYYRPMDE
Hamster   MKHMAGAAAAGAVVGGLGGYMLGSAMSRPMMHFGNDWEDRYYRENMNRYPNQVYYRPVDQ
Bovine    MKHVAGAAAAGAVVGGLGGYMLGSAMSRPLIHFGXDYEDRYYRENMHRYPNQVYYRPVDQ
Sheep     MKHVAGAAAAGAVVGGLGGYMLGSAMSRPLIHFGNDYEDRYYRENMYRYPNQVYYRPVDR
Mouse     LKHVAGAAAAGAVVGGLGGYMLGSAMSRPMIHFGNDWEDRYYRENMYRYPNQVYYRPVDQ
Elk       MKHVAGAAAAGAVVGGLGGYMLGSAMSRPLIHFGNDYEDRYYRENMYRYPNQVYYRPVDQ
Fallow    MKHVAGAAAAGAVVGGLGGYMLGSAMNRPLIHFGNDYEDRYYRENMYRYPNQVYYRPVDQ
Mule      MKHVAGAAAAGAVVGGLGGYMLGSAMSRPLIHFGNDYEDRYYRENMYRYPNQVYYRPVDQ
White     MKHVAGAAAAGAVVGGLGGYMLGSAMSRPLIHFGNDYEDRYYRENMYRYPNQVYYRPVDQ
          :**:******************** **::***  *:*********  ***********:*.

Human     YSNQNNFVHDCVNITIKQHTVTTTTKGENFTETDVKMMERVVEQMCITQYERESQAYYQ-
Hamster   YNNQNNFVHDCVNITIKQHTVTTTTKGENFTETDIKIMERVVEQMCTTQYQKESQAYYDG
Bovine    YSNQNNFVHDCVNITVKEHTVTTTTKGENFTETDIKMMERVVEQMCITQYQRESQAYYQ-
Sheep     YSNQNNFVHDCVNITVKQHTVTTTTKGENFTETDIKIMERVVEQMCITQYQRESQAYYQ-
Mouse     YSNQNNFVHDCVNITIKQHTVTTTTKGENFTETDVKMMERVVEQMCVTQYQKESQAYYDG
Elk       YNNQNTFVHDCVNITVKQHTVTTTTKGENFTETDIKMMERVVEQMCITQYQRESEAYYQ-
Fallow    YNNQNTFVHDCVNITVKQHTVTTTTKGENFTETDIKMMERVVEQMCITQYQRESEAYYQ-
Mule      YNNQNTFVHDCVNITVKQHTVTTTTKGENFTETDIKMMERVVEQMCITQYQRESQAYYQ-
White     YNNQNTFVHDCVNITVKQHTVTTTTKGENFTETDIKMMERVVEQMCITQYQRESQAYYQ-
          *.***.**********:*:*************:*:********* ***::**:***:

Human     -RGSSMVLFSSPPVILLISFLIFLIVG    (SEQ ID NO:3)
Hamster   RRSS-AVLFSSPPVILLISFLIFLMVG    (SEQ ID NO:4)
Bovine    -RGASVILFSSPPVILLISFLIFLIVG    (SEQ ID NO:5)
Sheep     -RGASVILFSSPPVILLISFLIFLIVG    (SEQ ID NO:6)
Mouse     RRSSSTVLFSSPPVILLISFLIFLIVG    (SEQ ID NO:7)
Elk       -RGASVILFSSPPVILLISFLIFLIVG    (SEQ ID NO:8)
Fallow    -RGASVILFSSPPVILLISFLIFLIVG    (SEQ ID NO:9)
Mule      -RGASVILFSSPPVILLISFLIFLIVG    (SEQ ID NO:10)
White     -RGASVILFSSPPVILLISFLIFLIVG    (SEQ ID NO:11)
```

Denaturation Profiles for vCJD (○) and sCJD (●)

PRION-SPECIFIC PEPTOID REAGENTS

CROSS REFERENCE TO RELATED APPLICATIONS

This application claims the benefit of U.S. Ser. Nos. 60/715,761, filed Sep. 9, 2005; 60/726,686, filed Oct. 14, 2005, and 60/758,934, filed Jan. 13, 2006, the disclosures of each of which are incorporated herein by reference in their entireties.

FIELD OF THE INVENTION

The invention relates to peptoid reagents useful in detecting and isolating prions, and in the treatment and prevention of prion-related diseases. The invention also relates to complexes, compositions and kits comprising the peptoid reagents and processes for preparing them.

BACKGROUND

Prion protein ($PrP^C$) is a 33-35 kD protein of uncertain function and, in humans, is transcribed by a gene on the short arm of chromosome 20. The 27-30 kD protease-resistant core (prion, scrapie protein, or $PrP^{Sc}$) is the functional component, with several isoforms responsible for "prion diseases," which are protein conformational diseases.

Protein conformational diseases arise from aberrant conformational transition of a protein (a conformational disease protein such as $PrP^C$), which in turn leads to self-association of the aberrant protein forms (e.g., $PrP^{Sc}$) resulting in tissue deposition and damage. Prions ($PrP^{Sc}$) have a substantially pleated sheet conformation rather than the α-helix structure of normal $PrP^C$, lack detectable nucleic acid, and generally do not elicit an immune response. In general, protein conformational diseases share striking similarities in clinical presentations, typically a rapid progression from diagnosis to death following varying lengths of incubation.

In humans, prion diseases, also known as, "transmissible spongiform encephalopathies" (TSEs), include, Creutzfeldt-Jakob disease (CJD), Gerstmann-Straussler-Scheinker syndrome (GSS), Fatal Familial Insomnia, and Kuru (see, e.g., Isselbacher et al., eds. (1994). *Harrison's Principles of Internal Medicine*. New York: McGraw-Hill, Inc.; Medori et al. (1992) *N. Engl. J. Med.* 326: 444-9). In animals, TSEs include sheep scrapie, bovine spongiform encephalopathy (BSE), transmissible mink encephalopathy, and chronic wasting disease of captive mule deer and elk (Gajdusek, (1990). Subacute Spongiform Encephalopathies: Transmissible Cerebral Amyloidoses Caused by Unconventional Viruses. In: *Virology*, Fields, ed., New York: Raven Press, Ltd. (pp. 2289-2324)). Transmissible spongiform encephalopathies are characterized by the same hallmarks: the presence of the abnormal (beta-rich, proteinase K resistant) conformation of the prion protein that transmits disease when experimentally inoculated into laboratory animals including primates, rodents, and transgenic mice.

Recently, the rapid spread of BSE and its correlation with elevated occurrence of TSEs in humans has led to increased interest in the detection of TSEs in non-human mammals. The tragic consequences of accidental transmission of these diseases (see, e.g., Gajdusek, *Infectious Amyloids, and Prusiner Prions In Fields Virology*. Fields, et al., eds. Philadelphia: Lippincott-Ravin, Pub. (1996); Brown et al. *Lancet*, 340: 24-27 (1992)), decontamination difficulties (Asher et al. (1986) In: Laboratory Safety: Principles and Practices, Miller ed., (pp. 59-71) Am. Soc. Micro.), and concern about BSE (*British Med. J.* (1995) 311: 1415-1421) underlie the urgency of having both a diagnostic test that would identify humans and animals with TSEs and therapies for infected subjects.

Prions differ significantly from bacteria, viruses and viroids. The dominating hypothesis is that, unlike all other infectious pathogens, infection is caused by an abnormal conformation of the prion protein, which acts as a template and converts normal prion conformations into abnormal, aberrant conformations. A prion protein was first characterized in the early 1980s. (See, e.g., Bolton, McKinley et al. (1982) *Science.* 218: 1309-1311; Prusiner, Bolton et al. (1982) *Biochemistry* 21: 6942-6950; McKinley, Bolton et al. (1983) *Cell* 35: 57-62). Complete prion protein-encoding genes have since been cloned, sequenced and expressed in transgenic animals. (See, e.g., Basler, Oesch et al. (1986) *Cell* 46: 417-428.)

The key characteristic of prion diseases is the formation of the abnormally shaped protein ($PrP^{Sc}$) from the normal form of prion protein (cellular or nonpathogenic or $PrP^C$). (See, e.g., Zhang et al. (1997) *Biochem.* 36(12): 3543-3553; Cohen & Prusiner (1998) *Ann. Rev. Biochem.* 67: 793-819; Pan et al. (1993) *Proc. Natl. Acad. Sci.* USA 90:10962-10966; Safar et al. (1993) *J Biol. Chem.* 268: 20276-20284.) The substantially β-sheet structure of $PrP^{Sc}$ as compared to the predominantly α-helical folded non-disease forms of $PrP^C$ has been revealed by optical spectroscopy and crystallography studies. (See, e.g., Wille et al. (2001) *Proc. Nat'l Acad. Sci. USA* 99: 3563-3568; Peretz et al. (1997) *J. Mol. Biol.* 273: 614-622; Cohen & Prusiner, (1999) 5: Structural Studies of Prion Proteins. In *Prion Biology And Diseases*, S. Prusiner, ed. Cold Spring Harbor, N.Y.: Cold Spring Harbor Laboratory Press. (pp: 191-228.) The structural changes appear to be followed by alterations in biochemical properties: $PrP^C$ is soluble in non- denaturing detergents, $PrP^{Sc}$ is insoluble; $PrP^C$ is readily digested by proteases, while $PrP^{Sc}$ is partially resistant, resulting in the formation of an amino-terminally truncated fragment known as "PrPres" (Baldwin et al. (1995); Cohen & Prusiner (1995)), "PrP 27-30" (27-30 kDa) or "PK-resistant" (proteinase K resistant) form. Additionally, $PrP^{Sc}$ can convert $PrP^C$ to the pathogenic conformation. See, e.g., Kaneko et al. (1995) *Proc. Nat'l Acad. Sci. USA* 92:11160-11164; Caughey (2003) *Br Med Bull.* 66: 109-20.

Detection of the pathogenic isoforms of conformational disease proteins in living subjects, and samples obtained from living subjects, has proven difficult. Thus, definitive diagnosis and palliative treatments for these transmissible and amyloid-containing conditions before death of the subject remains a substantially unmet challenge. Histopathological examination of brain biopsies is risky to the subject and lesions and amyloid deposits can be missed depending on where the biopsy sample is taken from. Also, there are still risks involved with biopsies to animals, patients, and health care personnel. Further, the results from brain tests on animals are not usually obtained until the animal has entered the food supply. Also, typically, antibodies generated against prion peptides recognize both denatured $PrP^{Sc}$ and $PrP^C$ but are unable to selectively recognize infectious (undenatured) $PrP^{Sc}$. (See, e.g., Matsunaga et al. (2001) *Proteins: Structure, Function and Genetics* 44: 110-118).

A number of tests for TSE are available (See, Soto, C. (2004) Nature Reviews Microbiol. 2:809, Biffiger et al. (2002) J. Virol. Meth. 101:79; Safar et al. (2002) Nature Biotech. 20:1147, Schaller et al. Acta Neuropathol. (1999) 98:437, Lane et al. (2003) Clin. Chem. 49:1774). However, all of these utilize brain tissue samples and are suitable only as post-mortem tests. Most of these require proteinase K treatment of the samples as well, which can be time-consuming, incomplete digestion of PrP$^C$ can lead to false positive results, and digestion of PK-sensitive PrP$^{SC}$ can yield false negative results.

Thus, there remains a need for compositions and methods for detecting the presence of the pathogenic prion proteins in various samples, for example in samples obtained from living subjects, in blood supplies, in farm animals and in other human and animal food supplies. There also remains a need for methods and compositions for diagnosing and treating prion-related diseases. This invention is directed to these, as well as other, important ends.

SUMMARY OF THE INVENTION

The present invention relates to peptoid reagents that interact with a conformational disease protein such as a prion protein, preferentially with a pathogenic form as compared to a nonpathogenic form of the conformational disease protein, having a formula of:

$$X^a\text{-}(Q)_n\text{-}X^b$$

wherein:
each Q is independently an amino acid or an N-substituted glycine, and -(Q)$_n$- defines a peptoid region;
$X^a$ is H, (C$_1$-C$_6$)alkyl, cycloalkyl, aryl, aralkyl, heteroaryl, heteroarylalkyl, heterocycloalkyl, (C$_1$-C$_6$)acyl, amino (C$_{1-6}$)acyl, an amino acid, an amino protecting group, or a polypeptide of 2 to about 100 amino acids, wherein $X^a$ is optionally substituted by a conjugate moiety that is optionally attached through a linker moiety;
$X^b$ is H, (C$_1$-C$_6$)alkyl, aryl, aralkyl, heteroaryl, heteroarylalkyl, heterocycloalkyl, amino, alkylamino, dialkylamino, hydroxyl, (C$_1$-C$_6$)alkoxy, aryloxy, aralkoxy, a carboxy protecting group, an amino acid, or a polypeptide of 2 to about 100 amino acids, wherein $X^b$ is optionally substituted by a conjugate moiety that is optionally attached through a linker moiety; and
n is 3 to about 30;

wherein at least about 50% of the peptoid region -(Q)$_n$- comprises N-substituted glycines.

The present invention also relates to peptoid reagents that are polyionic and have a net charge at physiologically relevant pH. In some embodiments, the peptoid reagents have a net positive charge at physiologically relevant pH, such as a charge of at least 3+ or at least 4+. The net charge can arise from one or more N-substituted glycines of the peptoid region.

The present invention further relates to a peptoid reagent that interacts preferentially with a pathogenic form of a conformational disease protein as compared to a nonpathogenic form of the conformational disease protein, wherein the reagent comprises an amino-terminal region, a carboxy-terminal region, and at least one peptoid region between the amino-terminal region and the carboxy-terminal region, wherein the peptoid region comprises 3 to about 30 N-substituted glycines and optionally one or more amino acids.

The present invention further provides a peptoid reagent that interacts preferentially with a pathogenic form of a conformational disease protein as compared to a nonpathogenic form of the conformational disease protein, wherein the reagent comprises a peptoid region comprising 3 to 15 contiguous N-substituted glycines, and wherein the peptoid region has a net charge at physiologically relevant pH. In some embodiments, the net charge is a net positive charge such as a net charge of at least 3+ or at least 4+ at physiologically relevant pH. In some embodiments, the peptoid reagent has a net charge of 2+ to 6+, 3+ to 5+, or 4+ at physiologically relevant pH.

The peptoid reagents of the invention can be used in a wide range of applications, including as tools to isolate pathogenic prions or to detect pathogenic prions in a sample, as components of a therapeutic or prophylactic composition and/or to generate prion-specific antibodies. For example, peptoid reagents that interact preferentially with PrP$^{SC}$ as compared to PrP$^C$ are useful for direct detection of pathogenic forms in samples obtained from living or once-living subjects, for example, for diagnosis of a disease or for screening donated blood samples or screening organs for organ donation. The peptoid reagents of the invention can be used to bind specifically to any PrP$^{SC}$ in the sample forming a complex. The complex can be detected directly by methods such as UV/Visible spectroscopy, FTIR, nuclear magnetic resonance spectroscopy, Raman spectroscopy, mass spectrometry, HPLC, capillary electrophoresis, surface plasmon resonance spectroscopy, Micro-Electro-Mechanical Systems (MEMS), or can be detected by the binding of additional prion-specific reagents (for example, a second peptoid reagent or a prion-binding reagent (as defined herein)) to the PrP$^{SC}$ in the complex or after dissociation from the complex.

Thus, the present invention relates to a method for detection of the presence of a pathogenic prion in a sample, which comprises contacting the sample with a first peptoid reagent of the invention under conditions that allow binding of the peptoid reagent to the pathogenic prion, if present, to form a complex, and detecting the formation of the complex, the formation of the complex being indicative of the presence of the pathogenic prion.

The method of detection of pathogenic prion in a sample also can comprise contacting the sample with a first peptoid reagent of the invention under conditions that allow binding of the first peptoid reagent to the pathogenic prion, if present, to form a first complex, contacting the first complex with a second peptoid reagent of the invention, optionally detectably labeled, under conditions that allow binding of the second peptoid reagent to the pathogenic prion of the first complex to form a second complex, and detecting formation of the second complex, the formation of the second complex being indicative of the presence of the pathogenic prion.

In a further embodiment, the method comprises contacting the sample with a first peptoid reagent of the invention under conditions that allow binding of the first peptoid reagent to the pathogenic prion, if present, to form a first complex, removing any unbound sample, contacting the first complex with a second peptoid reagent of the invention, optionally detectably labeled, under conditions that allow binding of the second peptoid reagent to the pathogenic prion of the first complex to form a second complex, and detecting formation of the second complex, the formation of the second complex being indicative of the presence of the pathogenic prion. The first peptoid reagent optionally comprises a solid support which aids in separation of the first complex from the unbound sample.

Further, the detection method of the invention can comprise contacting the sample with a first peptoid reagent of the invention under conditions that allow binding of the first peptoid reagent to the pathogenic prion, if present, to form a first complex, removing unbound sample, dissociating the pathogenic prion from the first complex thereby providing dissociated pathogenic prion, contacting the dissociated pathogenic prion with a second peptoid reagent of the invention, optionally detectably labeled, under conditions that allow binding of the second peptoid reagent to the dissociated pathogenic prion to form a second complex, and detecting the formation of the second complex, the formation of the second complex being indicative of the presence of the pathogenic prion.

The method of detection of pathogenic prion in a sample also can comprise contacting the sample with a first peptoid reagent of the invention under conditions that allow binding of the first peptoid reagent to the pathogenic prion, if present, to form a first complex, contacting the first complex with a prion-binding reagent, optionally detectably labeled, under conditions that allow binding of the prion-binding reagent to the pathogenic prion of the first complex to form a second complex, and detecting formation of the second complex, the formation of the second complex being indicative of the presence of the pathogenic prion.

In a further embodiment, the method comprises contacting the sample with a first peptoid reagent of the invention under conditions that allow binding of the first peptoid reagent to the pathogenic prion, if present, to form a first complex, removing any unbound sample, contacting the first complex with a prion-binding reagent, optionally detectably labeled, under conditions that allow binding of the prion-binding reagent to the pathogenic prion of the first complex to form a second complex, and detecting formation of the second complex, the formation of the second complex being indicative of the presence of the pathogenic prion. The first peptoid reagent optionally comprises a solid support which aids in separation of the first complex from the unbound sample.

Further, the detection method of the invention can comprise contacting the sample with a first peptoid reagent of the invention under conditions that allow binding of the first peptoid reagent to the pathogenic prion, if present, to form a first complex, removing unbound sample, dissociating the pathogenic prion from the first complex thereby providing dissociated pathogenic prion, contacting the dissociated pathogenic prion with a prion-binding reagent, optionally detectably labeled, under conditions that allow binding of the prion-binding reagent to the dissociated pathogenic prion to form a second complex, and detecting the formation of the second complex, the formation of the second complex being indicative of the presence of the pathogenic prion.

In a further embodiment, the detection method of the invention can comprise contacting the sample with a first peptoid reagent of the invention under conditions that allow binding of the first peptoid reagent to the pathogenic prion, if present, to form a first complex, removing unbound sample, dissociating the pathogenic prion from the first complex thereby providing dissociated pathogenic prion, contacting the dissociated pathogenic prion with a prion-binding reagent under conditions that allow binding of the prion-binding reagent to the dissociated pathogenic prion to form a second complex, and detecting the formation of the second complex using a second prion-binding reagent, optionally detectably labeled, the formation of the second complex being indicative of the presence of the pathogenic prion.

Moreover, the detection method can comprise contacting the sample with a prion-binding reagent under conditions that allow binding of the prion-binding reagent to the pathogenic prion, if present, to form a first complex, removing unbound sample, contacting the complex with a peptoid reagent of the invention, optionally detectably labeled, under conditions that allow binding of the peptoid reagent to the pathogenic prion of the first complex to form a second complex, and detecting the formation of the second complex, the formation of the second complex being indicative of the presence of the pathogenic prion. The prion-binding reagent is optionally provided on a solid support.

Further still, the detection method can comprise providing a solid support comprising a peptoid reagent of the invention, combining the solid support with a detectably labeled ligand, under conditions that allow binding of the detectably labeled ligand to the peptoid reagent, wherein the peptoid reagent of the support has a weaker binding affinity for the ligand than for the pathogenic prion, to form a first complex, combining the sample with the first complex under conditions that allow binding of the pathogenic prion, if present in the sample, to the peptoid reagent of the first complex, thereby replacing the detectably labeled ligand of the first complex and forming a second complex comprising the peptoid reagent and the pathogenic prion, and detecting the formation of the second complex, the formation of the second complex being indicative of the presence of the pathogenic prion.

The present invention further provides methods for detecting the presence of a pathogenic prion in a sample, comprising: contacting the sample with a first peptoid reagent of the invention under conditions that allow binding of the first peptoid reagent to the pathogenic prion, if present, to form a complex, removing unbound sample from the complex, dissociating the pathogenic prion from the complex thereby providing dissociated pathogenic prion, contacting the dissociated pathogenic prion with a second solid support under conditions that allow the dissociated pathogenic prion to adhere to the second solid support; and detecting the adhered dissociated pathogenic prion using a prion-binding reagent, optionally detectably labeled, wherein binding of the prion-binding reagent indicates the presence of the pathogenic prion. In some embodiments, the dissociating is carried out by exposing the complex to high pH or low pH. In some embodiments, the method further comprises the step of neutralizing the high pH or the low pH after the dissociating. In some embodiments, the dissociated pathogenic prion is denatured.

The present invention further provides methods for detecting the presence of a pathogenic prion in a sample, comprising contacting the sample with a first peptoid reagent of the invention under conditions that allow binding of the first peptoid reagent to the pathogenic prion, if present, to form a first complex, removing unbound sample from the first complex, dissociating the pathogenic prion from the first complex thereby providing dissociated pathogenic prion, contacting the dissociated pathogenic prion with a second solid support, wherein the second solid support comprises a first anti-prion antibody, under conditions that allow the dissociated pathogenic prion to bind to the first anti-prion antibody to form a second complex; and detecting the dissociated pathogenic prion of the second complex with a second anti-prion antibody, optionally detectably labeled, wherein binding of the second-anti-prion antibody indicates the presence of the pathogenic prion. In some embodiments, the dissociating is carried out by exposing the first complex to high pH or low pH. In some embodiments, the method further comprises the step of neutralizing the high pH or the low pH after the dissociating. In further embodiments, the dissociated pathogenic prion is denatured.

In all of the above methods utilizing prion-binding reagents, the prion-binding reagents can be, for example, anti-prion antibodies.

The invention further provides methods for treating or preventing prion-related infection in animals.

The invention is further directed to the detection or isolation of prion in a sample.

The invention is further directed to providing a supply of a substantially prion-free sample such as blood or food.

BRIEF DESCRIPTION OF THE DRAWINGS

FIG. 1. ELISA detection of PrP$^C$ in human plasma samples. FIG. 1A shows ELISA (RLU) measurements for increasing amounts of plasma. FIG. 1B shows a standard curve for ELISA (RLU) measurements using known amounts of recombinant PrP protein.

FIG. 2. This figure depicts the amino acid sequence of human (SEQ ID NO:1) and mouse (SEQ ID NO:2) prion proteins.

FIG. 3. This figure depicts an alignment of prion proteins from human (SEQ ID NO:3), Syrian hamster (hamster) (SEQ ID NO:4), bovine (SEQ ID NO:5), sheep (SEQ ID NO:6), mouse (SEQ ID NO:7), elk (SEQ ID NO:8), fallow deer (fallow) (SEQ ID NO:9), mule deer (mule) (SEQ ID NO:10), and white tailed deer (white) (SEQ ID NO:11). Elk, Fallow Deer, Mule Deer, and White Tailed Deer only vary from each other at two residues, S/N128 and Q/E226 (shown in bold).

DETAILED DESCRIPTION

Definitions

Figure 4:
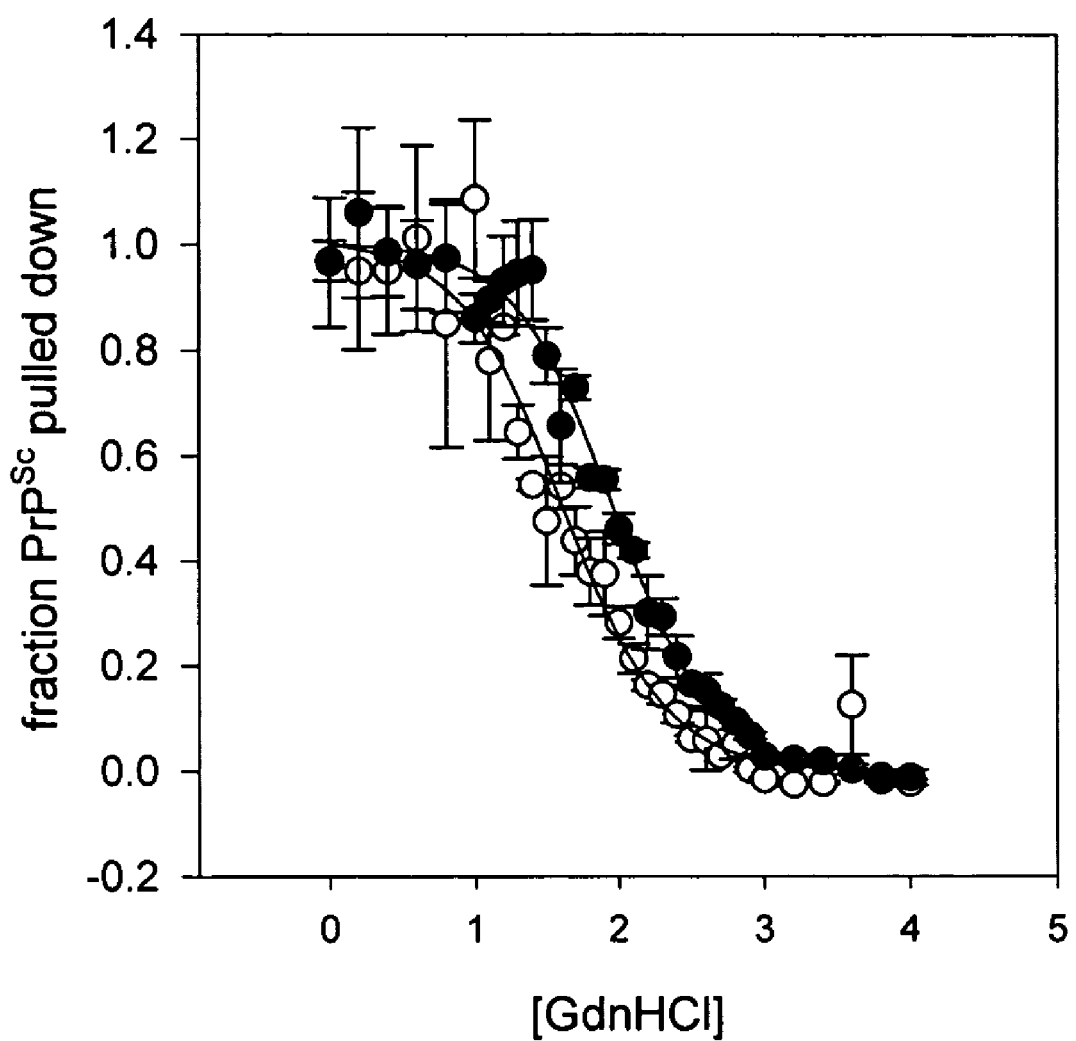
FIG. 4. This figure depicts denaturation profiles of vCJD and sCJD.

The following select terms will be discussed in the context used herein. Both the plural and singular forms of a term are included regardless of the form discussed.

"Prion," "prion protein," "PrP protein," and "PrP" are used interchangeably to refer to both the pathogenic prion protein form (also referred to as scrapie protein, pathogenic protein form, pathogenic isoform, pathogenic prion and PrP$^{Sc}$) and the non-pathogenic prion form (also referred to as cellular protein form, cellular isoform, nonpathogenic isoform, non-pathogenic prion protein, and PrP$^C$), as well as the denatured form and various recombinant forms of the prion protein that may not have either the pathogenic conformation or the normal cellular conformation.

"Conformational disease protein" refers to the pathogenic and non-pathogenic protein forms of a protein associated with a conformational disease where the structure of the protein has changed (e.g., misfolded or aggregated), resulting in an abnormal conformation such as unwanted fibril or amyloid polymerization in the context of beta pleated sheet. Example conformation disease proteins include, without limitation, prion proteins such as PrP$^{Sc}$ and PrP$^C$ and amino acid variations of the immunoglobulin light chain variable domain (VL), the protein component of the antibody molecule, which are associated with conformational diseases such as amyloidosis. A non-limiting list of diseases with associated proteins that assume two or more different conformations is shown below.

| Disease | Conformational Disease Protein(s) |
| --- | --- |
| Prion diseases (e.g., Creutzfeld Jakob disease, scrapie, bovine spongiform encephalopathy) | PrP$^{Sc}$ |
| Alzheimer's Disease | APP, A* peptide, *1-antichymotrypsin, tan, non-A* component |
| ALS | SOD and neurofilament |
| Pick's disease | Pick body |
| Parkinson's disease | Lewy body |
| Diabetes Type 1 | Amylin |
| Multiple myeloma - plasma cell dyscrasias | IgGL-chain |
| Familial amyloidotic polyneuropathy | Transthyretin |
| Medullary carcinoma of thyroid | Procalcitonin |
| Chronic Renal failure | beta2-microglobulin |
| Congestive heart failure | atrial natriuretic factor |
| senile cardiac and systemic amyloidosis | Transthyretin |
| Chronic inflammation | Serum amyloid A |
| Atherosclerosis | ApoA1 |
| Familial amyloidosis | Gelsolin |

Use of the terms "prion," "prion protein," "PrP protein," "PrP" or "conformational disease protein" is not meant to be limited to polypeptides having the exact sequences to those described herein. It is readily apparent that the terms encompass conformational disease proteins from any of the identified or unidentified species (e.g., human, bovine) or diseases (e.g., Alzheimer's, Parkinson's, etc.). See also, co-owned patent applications U.S. Ser. No. 10/917,646, filed Aug. 13, 2004, U.S. Ser. No. 11/056,950, filed Feb. 11, 2005, and International Application PCT/US2004/026363, filed Aug. 13, 2004, all entitled "Prion-Specific Peptide Reagents," which are incorporated herein by reference in their entireties. One of ordinary skill in the art in view of the teachings of the present disclosure and the art can determine regions corresponding to the sequences disclosed herein in any other prion proteins, using for example, sequence comparison programs (e.g., Basic Local Alignment Search Tool (BLAST)) or identification and alignment of structural features or motifs.

"Pathogenic" means that the protein actually causes the disease, or the protein is associated with the disease and, therefore, is present when the disease is present. Thus, a pathogenic protein, as used herein, is not necessarily a protein that is the specific causative agent of a disease. Pathogenic forms of a protein may or may not be infectious. An example of a pathogenic conformational disease protein is PrP$^{Sc}$. Accordingly, the term "non-pathogenic" describes a protein that does not normally cause disease or is not normally associated with causing disease. An example of a non-pathogenic conformational disease protein is PrP$^C$.

"Interact" in reference to a peptoid reagent interacting with a protein, e.g., a protein fragment, means the peptoid reagent binds specifically, non-specifically or in some combination of specific and non-specific binding to the prion protein. A peptoid reagent is said to "interact preferentially" with a pathogenic prion protein if it binds with greater affinity and/or greater specificity to the pathogenic form than to nonpathogenic isoforms. A peptoid reagent that interacts preferentially with a pathogenic prion protein is also referred to herein as a pathogenic prion-specific peptoid reagent. In some embodiments, the increased affinity and/or specificity is at least about 2-fold, at least about 5-fold, at least about 10-fold, at least about 50-fold, at least about 100-fold, at least about 500-fold, or at least about 1000-fold. It is to be understood that a preferential interaction does not necessarily require interaction between a specific amino acid or amino acid substitute residues and/or motifs of each peptide. For example, in some embodiments, the peptoid reagents of the invention interact preferentially with pathogenic isoforms but, nonetheless, can be capable of binding nonpathogenic isoforms at a weak, yet detectable, level (e.g., 10% or less of the binding shown to the polypeptide of interest). Typically, weak binding, or background binding, is readily discernible from the preferential interaction with the compound or polypeptide of interest, e.g., by use of appropriate controls. In general, peptoids of the invention bind pathogenic prions in the presence of a $10^6$-fold excess of nonpathogenic forms.

"Affinity" or "binding affinity," in terms of the peptoid reagent interacting with a conformational disease protein, refers to the strength of binding and can be expressed quantitatively as a dissociation constant ($K_d$). Binding affinity can be determined using techniques well known by one of ordinary skill in the art.

"Prion-related disease" refers to a disease caused in whole or in part by a pathogenic prion protein (e.g., $PrP^{Sc}$), for example, but without limitation, scrapie, bovine spongiform encephalopathies (BSE), mad cow disease, feline spongiform encephalopathies, kuru, Creutzfeldt-Jakob Disease (CJD), new variant Creutzfeldt-Jakob Disease (nvCJD), chronic wasting disease (CWD), Gerstmann-Strassler-Scheinker Disease (GSS), and fatal familial insomnia (FFI).

The term "denature" or "denatured" has the conventional meaning as applied to protein structure and means that the protein has lost its native secondary and tertiary structure. With respect to the pathogenic prion protein, a "denatured" pathogenic prion protein no longer retains the native pathogenic conformation and thus the protein is no longer "pathogenic." The denatured pathogenic prion protein has a conformation similar or identical to the denatured non-pathogenic prion protein. However, for purposes of clarity herein, the term "denatured pathogenic prion protein" will be used to refer to the pathogenic prion protein that is captured by the peptoid reagent as the pathogenic isoform and subsequently denatured. "Physiologically relevant pH" refers to a pH of about 5.5 to about 8.5; or about 6.0 to about 8.0; or usually about 6.5 to about 7.5.

"Aliphatic" refers to a straight-chained or branched hydrocarbon moiety. Aliphatic groups can include heteroatoms and carbonyl moieties.

"Alkyl," whether used alone or as part of another group, refers to an aliphatic hydrocarbon chain and includes, but is not limited to, straight and branched chains containing from 1 to 6, 1 to 5, 1 to 4, or 1 to 3 carbon atoms, unless explicitly specified otherwise. For example, methyl, ethyl, propyl, isopropyl, butyl, isobutyl, tert-butyl, etc. are encompassed by the term "alkyl."

"Alkenyl" is intended to denote alkyl groups that contain at least one double bond, e.g., 2 to 7, 2 to 6, 2 to 5, or 2 to 4 carbon atoms, including, for example but not limited to, vinyl, allyl, 2-methyl-allyl, 4-but-3-enyl, 4-hex-5-enyl, 3-methyl-but-2-enyl and the like.

"Alkynyl" is intended to denote alkyl groups that have at least one triple carbon-carbon bond, e.g., 2 to 7, 2 to 6, 2 to 5, or 2 to 4 carbon atoms. Example alkynyl groups include ethynyl, propynyl, and the like.

"Alkoxy," whether used alone or as part of another group, has its normal meaning of a group of formula —O-alkyl, e.g., methoxy, where alkyl is as defined herein.

"Halo" or "halogen," when used alone or as part of another group, has its normal meaning of Group VII elements, e.g., F, Cl, Br and I.

"Aryl," when used alone or as part of another group, means an aromatic hydrocarbon system, e.g., of 6 to 20, 6 to 14, or 6 to 10 ring carbon atoms, e.g., of 1, 2 or 3 rings, for example, phenyl, benzyl, naphthyl, naphthalene, anthracene, phenanthrenyl, anthracenyl, pyrenyl and the like. Also included in the definition of aryl are aromatic systems containing one or more fused non-aromatic carbocyclyl or heterocyclyl rings, for example, 1,2,3, 4-tetrahydronaphthalene and indan. The aryl group containing an fused non-aromatic ring can be attached through the aromatic portion or the non-aromatic portion.

"Aryl-alkyl" or "aralkyl" means a group of formula -alkyl-aryl, wherein aryl and alkyl have the definitions herein.

"Aryloxy," has its normal meaning of a group of formula —O-aryl, e.g., hydroxyphenyl, where aryl is as defined herein.

"Aralkoxy," has its normal meaning of a group of formula —O-alkyl-aryl, e.g., methoxyphenyl, where alkoxy and aryl are as defined herein.

"Cycloalkyl," whether used alone or as part of another group, has its normal meaning of a cyclic alkyl, alkenyl, or alkynyl group, e.g., a mono, bi-, tri-cyclic, fused, bridged or spiro saturated hydrocarbon moiety, e.g., of 3-10 carbon atoms, e.g., cyclopropyl. The term "cycloalkyl-aryl" is intended to denote a group of formula -aryl-cycloalkyl where aryl and cycloalkyl are as defined herein. "Cycloalkylalkyl" is intended to denote a group of formula -alkyl-cycloalkyl, for example, a cyclopropylmethyl or cyclohexylmethyl group, where alkyl and cycloalkyl are as defined herein.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example, phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 double or triple bonds.

"Heteroarylalkyl" refers to a group of formula -alkyl-heteroaryl, where alkyl and heteroaryl are as defined herein.

"Acyl" refers to a group of formula —C(O)-alkyl. In some embodiments, the acyl group has from 1 to 10, 1 to 8, 1 to 6, or 1 to 4 carbon atoms.

"Aminoacyl" refers to a group of formula —C(O)-alkyl-amino, where alkyl is as defined herein.

"Alkylamino" refers to a group of formula —NH-alkyl, where alkyl is as defined herein.

"Dialkylamino" refers to group of formula —N(alkyl)$_2$, where alkyl is as defined herein.

"Haloalkyl" refers to an alkyl group substituted by one or more halogens, where alkyl and halogen are as defined herein.

"Alkoxyalkyl" refers to a group of formula -alkyl-alkoxy, where alkyl and alkoxy are as defined herein.

"Carboxyalkyl" refers to a group of formula -alkyl-COOH, where alkyl is as defined herein.

"Carbamyl" refers to a group of formula —(O)NH$_2$.

"Carbamylalkyl" refers to a group of formula -alkyl-C(O)NH$_2$, where alkyl is as defined herein.

"Guanidinoalkyl" refers to a group of formula -alkyl-NHC(=NH)NH$_2$, where alkyl is as defined herein.

"Thiol" refers to a group of formula —SH.

"Alkylthiol" refers to a group of formula —S-alkyl, where alkyl is as defined herein.

"Alkylthioalkyl" refers to a group of formula -alkly-S-alkyl, where alkyl is as defined herein.

"Imidazolylalkyl" refers to a group of formula -alkyl-imidazolyl, where alkyl is as defined herein.

"Piperidylalkyl" refers to a group of formula -alkyl-piperidinyl, where alkyl is as defined herein.

"Naphthylalkyl" means a group of formula -alkyl-naphthyl, e.g., (8'-napthyl)methyl, where naphthyl has its normal meaning and alkyl is as defined herein.

"Indolylalkyl" means a group of formula -alkyl-indole, e.g., 3'-indolylethyl, and 3'-indolylmethyl, where indole has its normal meaning and alkyl is as defined herein.

"N-containing heterocyclyl" is meant to refer to any heteroaryl or heterocycloalkyl group containing at least one ring-forming N atom. Example N-containing heterocyclyl groups include pyridinyl, imidazolyl, piperidinyl, piperazinyl, pyrrolyl, indolyl, and the like.

"N-containing heterocyclylalkyl" is meant to refer to alkyl substituted by N-containing heterocyclylalkyl.

"Amino" and "primary amino" refer to NH$_2$. "Secondary amino" refers to NHR and "tertiary amino" refers to NR$_2$, where R is any suitable substituent.

"Ammonium" is meant to refer to the group —N(R)$_3^+$ where R can be any appropriate moiety such as alkyl, cycloalkyl, aryl, cycloalkylalkyl, arylalkyl, etc.

"Amino acid" refers to any of the twenty naturally occurring and genetically encoded α-amino acids or protected derivatives thereof. Protected derivatives of amino acids can contain one or more protecting groups on the amino moiety, carboxy moiety, or side chain moiety.

Examples of amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfonyl group, 2-nitrophenylsulfenyl, diphenylphosphine oxide and like amino-protecting groups.

Examples of carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, .beta.-(di(n -butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties.

The species of protecting group employed is not critical so long as the derivatized protecting group can be selectively removed at the appropriate point without disrupting the remainder of the molecule. Further examples of protecting groups are found in E. Haslam, *Protecting Groups in Organic Chemistry*, (J. G. W. McOmie, ed., 1973), at Chapter 2; and T. W. Greene and P. G. M. Wuts, *Protective Groups in Organic Synthesis*, (1991), at Chapter 7, the disclosures of each of which are incorporated herein by reference in their entireties.

"Peptoid" is used generally to refer to a peptide mimic that contains at least one, preferably two or more, amino acid substitutes, preferably N-substituted glycines. Peptoids are described in, inter alia, U.S. Pat. No. 5,811,387.

"N-Substituted glycine" refers to a residue of the formula —(NR—CH$_2$—CO)— where each R is a non-hydrogen moiety such as those independently selected from $(C_2-C_6)$alkyl, halo$(C_1-C_6)$alkyl, $(C_2-C_6)$alkenyl, $(C_2-C_6)$alkynyl, $(C_6-C_{10})$cycloalkyl-aryl, amino$(C_1-C_6)$alkyl, ammonium$(C_1-C_6)$alkyl, hydroxy$(C_1-C_6)$alkyl, $(C_1-C_6)$alkoxy$(C_1-C_6)$alkyl, carboxy, carboxy$(C_2-C_6)$alkyl, carbamyl, carbamyl$(C_2-C_6)$alkyl, guanidino, guanidino$(C_1-C_6)$alkyl, amidino, amidino$(C_1-C_6)$alkyl, thiol, $(C_1-C_6)$alkylthiol, alkylthioalkyl of 2-10 carbon atoms, N-containing heterocyclyl, N-containing heterocyclyl$(C_1-C_6)$alkyl, imidazolyl, imidazolylalkyl of 4-10 carbon atoms, piperidyl, piperidylalkyl of 5-10 carbon atoms, indolyl, indolylalkyl of 9-15 carbon atoms, naphthyl, naphthylalkyl of 11-16 carbon atoms, and aryl$(C_1-C_6)$alkyl; where each R moiety is optionally substituted with 1-3 substituents independently selected from halogen, hydroxy and $(C_1-C_6)$alkoxy.

In some embodiments of —(NR—CH$_2$—CO)—, R is $(C_2-C_6)$alkyl, halo$(C_1-C_6)$alkyl, $(C_2-C_6)$alkenyl, $(C_2-C_6)$alkynyl, $(C_6-C_{10})$cycloalkyl-aryl, amino$(C_1-C_6)$alkyl, hydroxy$(C_1-C_6)$alkyl, $(C_1-C_6)$alkoxy$(C_1-C_6)$alkyl, carboxy, carboxy$(C_2-C_6)$alkyl, carbamyl, carbamyl$(C_2-C_6)$alkyl, guanidino, guanidino$(C_1-C_6)$alkyl, thiol, $(C_1-C_6)$alkylthiol, alkylthioalkyl of 2-10 carbon atoms, imidazolyl, imidazolylalkyl of 4-10 carbon atoms, piperidyl, piperidylalkyl of 5-10 carbon atoms, indolyl, indolylalkyl of 9-15 carbon atoms, naphthyl, naphthylalkyl of 11-16 carbon atoms, diphenyl$(C_1-C_6)$alkyl or aryl$(C_1-C_6)$alkyl; where each R moiety is optionally substituted with 1-3 substituents independently selected from halogen, hydroxy and $(C_1-C_6)$alkoxy.

In some embodiments of —(NR—CH$_2$—CO)—, R is $(C_2-C_6)$alkyl, amino$(C_1-C_6)$alkyl, hydroxy$(C_1-C_6)$alkyl, $(C_1-C_6)$ alkoxy($C_1$-$C_6$)alkyl, guanidino($C_1$-$C_6$)alkyl, indolylalkyl of 9-15 carbon atoms, naphthylalkyl of 11-16 carbon atoms, diphenyl($C_1$-$C_6$)alkyl or aryl($C_1$-$C_6$)alkyl, substituted with 1-3 substituents independently selected from halogen, hydroxy or ($C_1$-$C_6$)alkoxy.

In some embodiments of —(NR—$CH_2$—CO)—, R is a moiety that is charged at physiologically relevant pH. Examples of positively charged R at physiologically relevant pH include, for example, amino($C_1$-$C_6$)alkyl, ammonium ($C_1$-$C_6$)alkyl, guanidino, guanidino($C_1$-$C_6$)alkyl, amidino, amidino($C_1$-$C_6$)alkyl, N-containing heterocyclyl, and N-containing heterocyclyl($C_1$-$C_6$)alkyl, wherein each R moiety is optionally substituted with 1-3 substituents independently selected from halogen, $C_1$-$C_3$ methoxy, and $C_1$-$C_3$ alkyl.

In some embodiments of —(NR—$CH_2$—CO)—, R is a moiety that is netural at physiologically relevant pH. Examples of neutral R at physiologically relevant pH include, for example, ($C_2$-$C_6$)alkyl, halo($C_1$-$C_6$)alkyl, ($C_2$-$C_6$)alkenyl, ($C_2$-$C_6$)alkynyl, ($C_6$-$C_{10}$)cycloalkyl-aryl, ($C_1$-$C_6$) alkoxy($C_1$-$C_6$)alkyl, alkylthioalkyl of 2-10 carbon atoms, diphenyl($C_1$-$C_6$)alkyl, and aryl($C_1$-$C_6$)alkyl. Further examples include ethyl, prop-1-yl, prop-2-yl, 1-methylprop-1-yl, 2-methylprop-1-yl, 3-phenylpropy-1-yl, 3-methylbutyl, benzyl, 4-chloro-benzyl, 4-methoxy-benzyl, 4-methyl-benzyl, 2-methylthioeth-1-yl, and 2,2-diphenylethyl.

In some embodiments of —(NR—$CH_2$—CO)—, R is amino($C_1$-$C_6$)alkyl (e.g., aminobutyl).

Further example N-substituted glycines include those where R is ethyl, prop-1-yl, prop-2-yl, 1-methylprop-1-yl, 2-methylprop-1-yl, 3-phenylpropy-1-yl, 3-methylbutyl, benzyl, 4-hydroxybenzyl, 4-chloro-benzyl, 4-methoxy-benzyl, 4-methyl-benzyl, 2-hydroxyethyl, mercaptoethyl, 2-aminoethyl, 3-propionic acid, 3-aminopropyl, 4-aminobutyl, 2-methylthioeth-1-yl, carboxymethyl, 2-carboxyethyl, carbamylmethyl, 2-carbamylethyl, 3-guanidinoprop-1-yl, imidazolylmethyl, 2,2-diphenylethyl or indol-3-yl-ethyl.

Also included are salts, esters, and protected forms (e.g., N-protected with Fmoc or Boc, etc.) of the N-substituted glycines.

Methods for making amino acid substitutes, including N-substituted glycines, are disclosed, inter alia, in U.S. Pat. No. 5,811,387, which is incorporated herein by reference in its entirety.

"Monomer" or "subunit" refers to a molecule that can be linked to other monomers to form a chain, e.g., a peptide. Amino acids and N-substituted glycines are example monomers. When linked with other monomers, a monomer can be referred to as a "residue."

"Peptoid reagent" as used herein refers to a peptide-like polymer in which one or more residues comprises an N-substituted glycine, as described further herein, and which interact preferentially with the pathogenic form of a conformational disease protein, particularly with a pathogenic prion protein. Linking each of the N-substituted glycines into a linear or branched chain optionally together with amino acids and/or other amino acid substitutes can produce "peptoid reagents," as described herein. The links typically constitute peptide bonds (i.e., amides).

"Peptide" refers to an amide compound comprising at least two amino acids joined by a peptide bond, i.e., by the linkage of the amino group of one amino acid to the carboxyl group of another amino acid. Peptide is used herein interchangeably with "oligopeptide" or "polypeptide," and no particular size polymer is implied by use of these terms. Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, peptides useful in this invention can have a maximum length suitable for the intended application. The peptide can be between about 2 and about 100, about 2 and about 50, about 2 and about 20, about 2 and about 10, about 2 and about 8, or about 2 and about 5 residues in length.

The "resemblance" between an amino acid in a peptide and its amino acid substitute need not be exact. For example, one may replace lysine with an N-substituted glycine residue (e.g., —(NR—$CH_2$—CO)—) in which R is an aminoalkyl group such as aminomethyl, 2-aminoethyl, 3-aminopropyl, 4-aminobutyl, 5-aminopentyl, or 6-aminohexyl. Serine can be replaced with, for example, hydroxyalkyl groups such as hydroxymethyl, 2-hydroxyethyl, 3-hydroxypropyl, 2-hydroxypropyl, and the like. In general, as an initial approach, a conventional amino acid can be replaced with an N-substituted glycine analog having a side chain of similar character, e.g., hydrophobic, hydrophilic, polar, nonpolar, aromatic, etc. Further testing and optimization of the amino acid substituted peptide can be done by the methods disclosed herein.

A "conjugate moiety" is a molecule covalently attached to the peptoid reagent. Example conjugate moieties include effector molecules, substrates, labels, cross-linking agents, binding agents, polymer scaffold, antigenic agent, spacer molecule, and the like. The attachment of conjugate groups to peptides and analogs thereof is well documented in the prior art. The conjugate moiety can be directly attached to the peptoid reagent or attached through a linking moiety. In some such embodiments, the conjugate moiety is attached to the peptoid reagent at the amino-terminal region or the carboxy-terminal region. In further embodiments, the conjugate moiety is attached at a terminal subunit such as an amino-terminal subunit or a carboxy-terminal subunit. In some such embodiments, the conjugate moiety is a cross-linking agent or binding agent. In some embodiments, the conjugate moiety comprises biotin or a mercapto group. In some embodiments, the conjugate moiety comprises a dectable label. In some embodiments, the peptoid reagent comprises two or more conjugates.

The terms "label," "labeled," "detectable label," and "detectably labeled" refer to a molecule capable of detection, including, but not limited to, radioactive isotopes, fluorescers, luminescers, chemiluminescers, enzymes, enzyme substrates, enzyme cofactors, enzyme inhibitors, chromophores, dyes, metal ions, metal sols, ligands (e.g., biotin or haptens), fluorescent nanoparticles, gold nanoparticles, and the like. The term "fluorescer" refers to a substance or a portion thereof that is capable of exhibiting fluorescence in the detectable range such as a fluorophore. Particular examples of labels that can be used with the invention include, but are not limited to fluorescein, rhodamine, dansyl, umbelliferone, Texas red, luminol, acridinium esters, NADPH, beta-galactosidase, horseradish peroxidase, glucose oxidase, alkaline phosphatase and urease. The label can also be an epitope tag (e.g., a His-His tag), an antibody or an amplifiable or otherwise detectable oligonucleotide.

The term "effector compound" includes any compound that binds to a biological receptor site and effects a biochemical event after so binding. Thus, effector compound includes pharmaceutical drug as well as insecticides, but is not limited to either.

The term "cross-linking agent" refers to moieties that have functionalities capable of forming covalent bonds with other molecules or polymeric scaffolds. Examples of cross-linking agents include those having one or more terminal mercapto, hydroxyl, amino, carboxyl, and similar functionalities. In some embodiments, the cross-linking agent has at least one mercapto functionality.

The term "binding agent" refers to a moiety that is capable of binding, through non-covalent interactions, with another molecule or substance such as a polymeric scaffold. An example binding agent is biotin or derivative thereof.

A "linker moiety," "linking moiety" or "linker" refers to a moiety that tethers the conjugate moiety to the peptoid reagent. In some embodiments, the linker moiety is a group having at least one linking region with the formula —{NH(CH$_2$)$_m$C(O)}$_p$— where m is 1 to 10 and p is 1 to 5. In some embodiments, the linker moiety comprises at least one residue of aminohexanoic acid (Ahx) or fragment thereof. Such moieties may further enhance interaction of the peptoid reagent with the prion proteins and/or further enhance detection of prion proteins.

Peptoid Reagents

The present invention provides peptoid reagents that interact with conformational disease proteins such as prion proteins, complexes, compositions and kits containing the peptoid reagents and methods of using them for the detection and isolation of conformational disease proteins such as PrP$^{Sc}$. The peptoid reagents of the invention can be utilized in the treatment and prevention of protein conformational diseases, e.g., prion diseases such as TSEs, as well as in a method for providing a blood or food supply that is substantially free of pathogenic prion.

The invention provides a peptoid reagent that interacts preferentially with a pathogenic form of a conformational disease protein as compared to a nonpathogenic form of the conformational disease protein having a formula of:

$$X^a\text{-}(Q)_n\text{-}X^b$$

wherein:
each Q is independently an amino acid or an N-substituted glycine, and -(Q)$_n$- defines a peptoid region;
$X^a$ is H, (C$_1$-C$_6$)alkyl, cycloalkyl, aryl, aralkyl, heteroaryl, heteroarylalkyl, heterocycloalkyl, (C$_1$-C$_6$)acyl, amino(C$_{1-6}$)acyl, an amino acid, an amino protecting group, or a polypeptide of 2 to about 100 amino acids, wherein $X^a$ is optionally substituted by a conjugate moiety that is optionally attached through a linker moiety;
$X^b$ is H, (C$_1$-C$_6$)alkyl, aryl, aralkyl, heteroaryl, heteroarylalkyl, heterocycloalkyl, amino, alkylamino, dialkylamino, hydroxyl, (C$_1$-C$_6$)alkoxy, aryloxy, aralkoxy, a carboxy protecting group, an amino acid, or a polypeptide of 2 to about 100 amino acids, wherein $X^b$ is optionally substituted by a conjugate moiety that is optionally attached through a linker moiety; and
n is 3 to about 30 (that is n is 3, 4, 5, 6, 7, 8, 9, 10, 11, 12, 13, 14, 15, 16, 17, 18, 19, 20, 21, 22, 23, 24, 25, 26, 27, 28, 29, or 30, or more);

wherein at least about 50% of the peptoid region -(Q)$_n$- comprises N-substituted glycines.

In some embodiments, each Q is independently an N-substituted glycine.

In some embodiments, the peptoid reagent has a formula of $X^a$-(Q)$_n$-$X^b$, where n is about 4 to about 30, preferably about 5 to about 30, and where at least about 50% of the peptoid region -(Q)$_n$- comprises N-substituted glycines, provided that the peptoid region -(Q)$_n$- comprises at least one subregion independently selected from:

(a) -AABA-;
(b) -AABAB-
(c) -ABACC-;
(d) -AAAAA-;
(e) -ABCBA-;
(f) -AABCA-; or
(g) -ABABA-;

where A, B, and C are each different N-substituted glycines.

In some embodiments, $X^a$ is (C$_1$-C$_6$)acyl or amino(C$_{1-6}$)acyl, each optionally substituted by a conjugate moiety that is optionally attached through a linker moiety.

In some embodiments, $X^a$ is (C$_1$-C$_6$)acyl or amino(C$_{1-6}$)acyl, each optionally substituted by a conjugate moiety selected from a cross-linking or binding reagent each optionally attached through a linker moiety.

In some embodiments, $X^a$ is (C$_1$-C$_6$)acyl or amino(C$_{1-6}$)acyl, each optionally substituted by a conjugate moiety selected from biotin or mercapto, where the conjugate moiety is optionally attached through a linker moiety.

In some embodiments, $X^b$ is an amino acid optionally substituted by a conjugate moiety that is optionally attached through a linker moiety.

In some embodiments, $X^b$ is amino, alkylamino, dialkylamino.

In some embodiments, $X^b$ is amino.

In some embodiments, n is about 5 to about 15; 5 to about 10; or 6.

In some embodiments, n is 4 to 10, 4 to 8, 5 to 7 or 6.

In some embodiments, $X^b$ is an amino acid optionally substituted by a conjugate moiety and n is 6.

In some embodiments, the linker moiety contains a region having the formula —{NH(CH$_2$)$_m$C(O)}$_p$—.

In some embodiments, m is 1 to 10.

In some embodiments, m is 1 to 8.

In some embodiments, m is 5.

In some embodiments, p is 1 to 5.

In some embodiments, p is 1 to 3.

In some embodiments, p is 1 or 2.

In some embodiments, $X^b$ is an amino acid optionally substituted by a conjugate moiety that is optionally attached through a linker moiety, and n is 6.

In some embodiments, $X^b$ is amino, alkylamino, or dialkylamino; $X^a$ is H, (C$_1$-C$_6$)alkyl, (C$_1$-C$_6$)acyl, amino(C$_{1-6}$)acyl, an amino acid, or an amino protecting group, wherein $X^a$ is optionally substituted by a conjugate moiety that is optionally attached through a linker moiety; and n is 6.

In some embodiments, $X^b$ is amino, alkylamino, or dialkylamino; $X^a$ is H, (C$_1$-C$_6$)alkyl, (C$_1$-C$_6$)acyl, amino(C$_{1-6}$)acyl, an amino acid, or an amino protecting group, wherein $X^a$ is substituted by a conjugate moiety selected from a crosslinking agent or binding agent, wherein the conjugate moiety is optionally attached through a linker moiety; and n is 6.

In some embodiments, $X^b$ is amino, alkylamino, or dialkylamino; $X^a$ is H, (C$_1$-C$_6$)alkyl, (C$_1$-C$_6$)acyl, amino(C$_{1-6}$)acyl, an amino acid, or an amino protecting group, wherein $X^a$ is substituted by a conjugate moiety comprising biotin or mercapto, wherein the conjugate moiety is optionally attached through a linker moiety wherein at least a portion of the linker moiety has the formula —{NH(CH$_2$)$_m$C(O)}$_p$—; n is 6; m is 1 to 10; and p is 1 to 5.

In some embodiments, each Q is independently an amino acid or an N-substituted glycine having the formula —(NR—CH$_2$—CO)— wherein each R is independently selected from (C$_2$-C$_6$)alkyl, halo(C$_1$-C$_6$)alkyl, (C$_2$-C$_6$)alkenyl, (C$_2$-C$_6$)alkynyl, (C$_6$-C$_{10}$)cycloalkyl-aryl amino(C$_1$-C$_6$)alkyl, ammonium(C$_1$-C$_6$)alkyl, hydroxy(C$_1$-C$_6$)alkyl, (C$_1$-C$_6$)alkoxy(C$_1$-C$_6$)alkyl, carboxy, carboxy(C$_2$-C$_6$)alkyl, carbamyl, carbamyl(C$_2$-C$_6$)alkyl, guanidino, guanidino(C$_1$-C$_6$)alkyl, amidino, amidino($C_1$-$C_6$)alkyl, thiol, ($C_1$-$C_6$)alkylthiol, alkylthioalkyl of 2-10 carbon atoms, N-containing heterocyclyl, N-containing heterocyclyl($C_1$-$C_6$)alkyl, imidazolyl, imidazolylalkyl of 4-10 carbon atoms, piperidyl, piperidylalkyl of 5-10 carbon atoms, indolyl, indolylalkyl of 9-15 carbon atoms, naphthyl, naphthylalkyl of 11-16 carbon atoms, and aryl($C_1$-$C_6$)alkyl; where each R moiety is optionally substituted with 1-3 substituents independently selected from halogen, hydroxy and ($C_1$-$C_6$)alkoxy.

In some embodiments, each Q is independently an amino acid or an N-substituted glycine having the formula —(NR—$CH_2$—CO)— wherein each R is independently selected from ($C_2$-$C_6$)alkyl, halo($C_1$-$C_6$)alkyl, ($C_2$-$C_6$)alkenyl, ($C_2$-$C_6$)alkynyl, ($C_6$-$C_{10}$)cycloalkyl-aryl, amino($C_1$-$C_6$)alkyl, hydroxy($C_1$-$C_6$)alkyl, ($C_1$-$C_6$)alkoxy($C_1$-$C_6$)alkyl, carboxy, carboxy($C_2$-$C_6$)alkyl, carbamyl, carbamyl($C_2$-$C_6$)alkyl, guanidino, guanidino($C_1$-$C_6$)alkyl, thiol, ($C_1$-$C_6$)alkylthiol, alkylthioalkyl of 2-10 carbon atoms, imidazolyl, imidazolylalkyl of 4-10 carbon atoms, piperidyl, piperidylalkyl of 5-10 carbon atoms, indolyl, indolylalkyl of 9-15 carbon atoms, naphthyl, naphthylalkyl of 11-16 carbon atoms, diphenyl($C_1$-$C_6$)alkyl or aryl($C_1$-$C_6$)alkyl; where each R moiety is optionally substituted with 1-3 substituents independently selected from halogen, hydroxy and ($C_1$-$C_6$)alkoxy.

In some embodiments, each Q is independently an amino acid or an N-substituted glycine of the formula —(NR—$CH_2$—CO)— wherein each R is independently selected from ($C_2$-$C_6$)alkyl, amino($C_1$-$C_6$)alkyl, hydroxy($C_1$-$C_6$)alkyl, ($C_1$-$C_6$)alkoxy($C_1$-$C_6$)alkyl, guanidino($C_1$-$C_6$)alkyl, indolylalkyl of 9-15 carbon atoms, naphthylalkyl of 11-16 carbon atoms, diphenyl($C_1$-$C_6$)alkyl or aryl($C_1$-$C_6$)alkyl, substituted with 1-3 substituents independently selected from halogen, hydroxy or ($C_1$-$C_6$)alkoxy.

In some embodiments, each Q is independently an amino acid or is an N-substituted glycine selected from N-(4-aminobutyl)glycine, N-(1-phenylethyl)glycine, N-(2-aminoethyl)glycine, N-(2-[4-methoxyphenyl]ethyl)glycine, N-(2-methoxyethyl)glycine, N-(2-hydroxyethyl)glycine, N-((1H-indol-3-yl)methyl)glycine, or N-benzylglycine.

In some embodiments, each Q is independently an amino acid or is an N-substituted glycine selected from N-(4-aminobutyl)glycine or N-benzylglycine.

In some embodiments, each Q is independently an N-substituted glycine.

In some embodiments, the peptoid region -$(Q)_n$- comprises at least 3 or at least 4 N-substituted glycines which are charged at physiologically relevant pH. In some embodiments, the charge is positive. In some embodiments, the remaining N-substituted glycines of the peptoid region are neutral at physiologically relevant pH.

In some embodiments, the peptoid region -$(Q)_n$- comprises 2 to 6, 3 to 5, or 4 N-substituted glycines which are charged at physiologically relevant pH. In some embodiments, the charge is positive. In some embodiments, the remaining N-substituted glycines of the peptoid region are neutral at physiologically relevant pH.

In some embodiments, two N-substituted glycine residues of the peptoid region -$(Q)_n$- are positively charged at physiologically relevant pH and the remaining N-substituted glycine residues of the peptoid region are neutral at physiologically relevant pH.

In some embodiments, three N-substituted glycine residues of the peptoid region -$(Q)_n$- are positively charged at physiologically relevant pH and the remaining N-substituted glycine residues of the peptoid region are neutral at physiologically relevant pH.

In some embodiments, four N-substituted glycine residues of the peptoid region -$(Q)_n$- are positively charged at physiologically relevant pH and the remaining N-substituted glycine residues of the peptoid region are neutral at physiologically relevant pH.

In some embodiments, five N-substituted glycine residues of the peptoid region -$(Q)_n$- are positively charged at physiologically relevant pH and the remaining N-substituted glycine residues of the peptoid region are neutral at physiologically relevant pH.

In some embodiments, the peptoid region -$(Q)_n$- is polyionic at physiologically relevant pH.

In some embodiments, the peptoid region -$(Q)_n$- is polycationic at physiologically relevant pH.

In some embodiments, the peptoid region -$(Q)_n$- is polyanionic at physiologically relevant pH.

In some embodiments, the peptoid region -$(Q)_n$- has a net charge of at least 3+ at physiologically relevant pH.

In some embodiments, the peptoid region -$(Q)_n$- has a net charge of at least 4+ at physiologically relevant pH.

In some embodiments, the peptoid region -$(Q)_n$- has a net charge of 2+ to 6+ at physiologically relevant pH.

In some embodiments, the peptoid region -$(Q)_n$- has a net charge of 3+ to 5+ at physiologically relevant pH.

In some embodiments, the peptoid region -$(Q)_n$- has a net charge of 4+ at physiologically relevant pH.

In some embodiments, the peptoid region -$(Q)_n$- comprises at least 3 N-substituted glycines that are positively charged at physiologically relevant pH.

In some embodiments, wherein the peptoid region -$(Q)_n$- comprises at least 4 N-substituted glycines that are positively charged at physiologically relevant pH.

In some embodiments, the peptoid region -$(Q)_n$- comprises from 2 to 6 N-substituted glycines that are positively charged at physiologically relevant pH.

In some embodiments, the peptoid region -$(Q)_n$- comprises from 3 to 5 N-substituted glycines that are positively charged at physiologically relevant pH.

In some embodiments, the peptoid region -$(Q)_n$- comprises 4 N-substituted glycines that are positively charged at physiologically relevant pH.

In some embodiments, the N-substituted glycines of peptoid region -$(Q)_n$- have the formula —(NR—$CH_2$—CO)—, wherein R is independently selected from ($C_2$-$C_6$)alkyl, halo($C_1$-$C_6$)alkyl, ($C_2$-$C_6$)alkenyl, ($C_2$-$C_6$)alkynyl, ($C_6$-$C_{10}$)cycloalkyl-aryl, amino($C_1$-$C_6$)alkyl, ammonium($C_1$-$C_6$)alkyl, hydroxy($C_1$-$C_6$)alkyl, ($C_1$-$C_6$)alkoxy($C_1$-$C_6$)alkyl, carboxy, carboxy($C_2$-$C_6$)alkyl, carbamyl, carbamyl($C_2$-$C_6$)alkyl, guanidino, guanidino($C_1$-$C_6$)alkyl, amidino, amidino($C_1$-$C_6$)alkyl, thiol, ($C_1$-$C_6$)alkylthiol, alkylthioalkyl of 2-10 carbon atoms, N-containing heterocyclyl, N-containing heterocyclyl ($C_1$-$C_6$)alkyl, imidazolyl, imidazolylalkyl of 4-10 carbon atoms, piperidyl, piperidylalkyl of 5-10 carbon atoms, indolyl, indolylalkyl of 9-15 carbon atoms, naphthyl, naphthylalkyl of 11-16 carbon atoms, and aryl($C_1$-$C_6$)alkyl; where each R moiety is optionally substituted with 1-3 substituents independently selected from halogen, hydroxy and ($C_1$-$C_6$) alkoxy, and the peptoid region -$(Q)_n$- comprises at least 3, at least 4, 2 to 6, 3 to 5, or 4 N-substituted glycines wherein R is a moiety that is charged at physiologically relevant pH.

In some embodiments, all the N-substituted glycines of the peptoid region are contiguous.

In some embodiments, the peptoid reagent comprises at least one conjugate moiety.

In some embodiments, the peptoid reagent comprises at least one conjugate moiety attached through a linker moiety.

The invention further provides a peptoid reagent that interacts preferentially with a pathogenic form of a conformational disease protein as compared to a nonpathogenic form of the conformational disease protein where the peptoid reagent comprises an amino-terminal region, a carboxy-terminal region, and at least one peptoid region between the amino-terminal region and the carboxy-terminal region where the peptoid region comprises about 3 to about 30 N-substituted glycines and optionally one or more amino acids. In some embodiments, the peptoid region comprises about 4 to about 30 or about 5 to about 30 N-substituted glycines. In some such embodiments, the peptoid region comprises about 4 to about 30, or about 5 to about 30 N-substituted glycines and a peptoid subregion selected from:

(a) -AABA-;
(b) -AABAB-
(c) -ABACC-;
(d) -AAAAA-;
(e) -ABCBA-;
(f) -AABCA-; or
(g) -ABABA-;

wherein A, B, and C are each different N-substituted glycines, and each subregion sequence is read from left to right in the amino-terminal to carboxy-terminal direction.

In some embodiments, the peptoid region comprises about 50 to about 100%, about 75 to about 100%, or 100% N-substituted glycines.

In some embodiments, the peptoid region is about 5 to about 50, about 5 to about 30, about 5 to about 15, about 5 to about 7, or 6 subunits in length.

In some embodiments, the peptoid reagent has a total length of about 5 to about 50, about 5 to about 30, about 5 to about 15, or about 6 to about 9 subunits.

In some embodiments, at least one peptoid region is greater than about 50%, greater than about 75%, or greater than about 90% of the total length of the peptoid reagent.

In some embodiments, all the N-substituted glycines are contiguous in the peptoid region.

In some embodiments, the N-substituted glycines of the peptoid region have the formula —(NR—CH$_2$—CO)— wherein R is as defined hereinthroughout.

In some embodiments, the peptoid region is polyionic at physiologically relevant pH and has characteristics according to any of the embodiments described herein throughout for charged peptoid regions.

The present invention further provides a peptoid reagent that interacts preferentially with a pathogenic form of a conformational disease protein as compared to a nonpathogenic form of the conformational disease protein, wherein the reagent comprises a peptoid region comprising 3 to 15 contiguous N-substituted glycines, and wherein the peptoid region has a net charge at physiologically relevant pH. In some embodiments, the net charge is a net positive charge such as a net charge of at least 3+ or at least 4+ at physiologically relevant pH. In some embodiments, the peptoid reagent itself has a net charge of 2+ to 6+, 3+ to 5+, or 4+ at physiologically relevant pH.

In some embodiments, at least two, at least 3, or at least 4 of the contiguous N-substituted glycines of the peptoid region are charged at physiologically relevant pH. In further embodiments, at least two of the contiguous N-substituted glycines of the peptoid region comprise at least one moiety selected from primary amino, secondary amino, tertiary amino, ammonium (quaternary amino), guanidino, amidino, or N-containing heterocyclyl.

In yet further embodiments, at least two of the contiguous N-substituted glycines of the peptoid region comprises at least one N-substituent selected from primary amino, secondary amino, ammonium, guanidino, amidino, or N-containing heterocyclyl.

In yet further embodiments, at least two of the contiguous N-substituted glycines comprise an N-substituent which is an R group according to the definitions provided herein.

In yet further embodiments, the peptoid reagent comprises a peptoid region of 6 contiguous N-substituted glycines and the peptoid reagent itself has a net charge of 3+ or 4+ at physiologically relevant pH.

The invention also provides methods for making the peptoid reagents and for using the peptoid reagents to detect pathogenic prion proteins, methods for isolation of pathogenic prion proteins using the peptoid reagents, methods for the elimination or reduction of pathogenic prion proteins from samples and kits containing components for carrying out the various methods.

A "peptoid reagent" refers to a peptoid molecule having an amino-terminal region, a carboxy-terminal region, and at least one "peptoid region" between the amino-terminal region and the carboxy-terminal region. The amino-terminal region refers to a region on the amino-terminal side of the reagent that typically does not contain any N-substituted glycines. The amino-terminal region can be H, alkyl, substituted alkyl, acyl, an amino protecting group, an amino acid, a peptide, or the like. In some embodiments, the amino-terminal region corresponds to $X^a$. The carboxy-terminal region refers to a region on the carboxy-terminal end of the peptoid that does not contain any N-substituted glycines. The carboxy-terminal region can include H, alkyl, alkoxy, amino, alkylamino, dialkylamino, a carboxy protecting group, an amino acid, a peptide, or the like. In some embodiments, the carboxy-terminal region corresponds to $X^b$. In some embodiments, the peptoid reagent has a total length of about 5 to about 50 subunits; about 5 to about 30 subunits; about 5 to about 15 subunits; or about 6 to about 9 subunits. In some embodiments, the peptoid reagent is a carboxy-terminal amide. The peptoid region generally refers to a portion of the peptoid reagent in which at least three of the amino acids therein are replaced by N-substituted glycines.

The "peptoid region" (also designated "-(Q)$_n$-" herein) can be identified as the region starting with and including the N-substituted glycine closest to the amino-terminus and ending with and including the N-substituted glycine closest to the carboxy-terminus. In some embodiments, the peptoid region comprises at least about 50%, at least about 60%, at least about 70%, at least about 80%, at least about 90%, at least about 95%, at least about 99%, or 100% N-substituted glycines. In some embodiments, the peptoid region comprises about 25 to about 100%; about 50 to about 100%; about 75 to about 100% N-substituted glycines. In some embodiments, the peptoid region comprises 100% N-substituted glycines. In some embodiments, the peptoid region is greater than about 50% (e.g., about 50-100%) of the total length of the peptoid reagent. In some embodiments, the peptoid region is greater than about 60% (e.g., about 60-100%) of the total length of the peptoid reagent. In some embodiments, the peptoid region is greater than about 75% (e.g., about 75-100%) of the total length of the peptoid reagent. In some embodiments, the peptoid region is greater than about 90% (e.g., about 90-100%) of the total length of the peptoid reagent. In some embodiments, the peptoid region is 100% of the total length of the peptoid reagent.

In some embodiments, the peptoid region comprises at least 3 N-substituted glycines. In some embodiments, the peptoid region comprises at least 4 N-substituted glycines. In some embodiments, the peptoid region comprises at least 5 N-substituted glycines. In some embodiments, the peptoid region comprises at least 6 N-substituted glycines. In some embodiments, the peptoid region comprises 3 to about 30; about 5 to about 30 N-substituted glycines; and optionally one or more amino acids. In some embodiments, the peptoid region is about 5 to about 50, 5 to about 30, 5 to about 15, 5 to about 10, 5 to about 9, 5 to about 8, or 5 to about 7 subunits in length. In some embodiments, the peptoid region is about 3, 4, 5, 6, 7, 8, 9, or 10 subunits in length. In some embodiments, the peptoid region is 6 subunits in length. In some embodiments, all of the N-substituted glycines in the peptoid region are contiguous. In some embodiments, all of the subunits of the peptoid region are N-substituted glycines.

In further embodiments, the peptoid reagent comprises a peptoid region of 4 to 12, 4 to 10, 4 to 9, 4, to 8, 5 to 7, or 6 contiguous N-substituted glycines.

According to some embodiments, the peptoid region can be polyionic at physiologically relevant pH. By the term "polyionic" is meant that the peptoid region comprises two or more residues that are charged at physiologically relevant pH. In some embodiments, the peptoid region is polycationic or polyanionic at physiologically relevant pH. In further embodiments, the peptoid region has a net charge of at least 3+ or at least 4+ at physiologically relevant pH. In yet further embodiments, the peptoid region has a net charge of 2+ to 6+, 3+ to 5+, or 4+ at physiologically relevant pH.

Non-limiting examples of N-substituted glycine residues that are charged include N-(5-aminopentyl)glycine, N-(4-aminobutyl)glycine, N-(3-aminopropyl)glycine, N-(2-aminoethyl)glycine, N-(5-guanidinopentyl)glycine, N-(4-guanidinobutyl)glycine, N-(3-guanidinopropyl)glycine, and N-(2-guanidinoethyl)glycine.

In some embodiments, the peptoid region comprises at least 3 or at least 4 N-substituted glycines that are positively charged at physiologically relevant pH. In some embodiments, the peptoid region comprises from 2 to 6, 3 to 5, or 4 amino N-substituted glycines that are positively charged at physiologically relevant pH.

In some embodiments, the peptoid region comprises residues having the formula —(NR—CH$_2$—CO)— where at least 3, at least 4, 2 to 6, 3 to 5, or 4 of the residues are charged at physiologically relevant pH.

In some embodiments, the charged residues of the peptoid region have the formula —(NR—CH$_2$—CO)— wherein R is independently selected from amino(C$_1$-C$_6$)alkyl, ammonium (C$_1$-C$_6$)alkyl, guanidino, guanidino(C$_1$-C$_6$)alkyl, amidino, amidino(C$_1$-C$_6$)alkyl, N-containing heterocyclyl, and N-containing heterocyclyl(C$_1$-C$_6$)alkyl, wherein each R moiety is optionally substituted with 1-3 substituents independently selected from halogen, C$_1$-C$_3$ methoxy, and C$_1$-C$_3$ alkyl. In some embodiments, R is amino(C$_1$-C$_6$)alkyl such as aminobutyl.

In some embodiments, the peptoid reagent has a net charge of at least 3+ or at least 4+ at physiologically relevant pH. In yet further embodiments, the peptoid reagent has a net charge of 2+ to 6+, 3+ to 5+, or 4+ at physiologically relevant pH.

The peptoid region of the peptoid reagent comprises at least one peptoid subregion, which refers to a sequence of contiguous N-substituted glycines of 2, 3, 4, 5, 6, 7, 8, 9, 10, 11 or 12 or more residues. In some embodiments, the peptoid region comprises at least one peptoid subregion independently selected from:
 (a) -AABA-;
 (b) -AABAB
 (c) -ABACC-;
 (d) -AAAAA-;
 (e) -ABCBA-;
 (f) -AABCA-; or
 (g) -ABABA-.

A, B, and C each represent different N-substituted glycines. For example, each A occurring in the subregion refers to a particular N-substituted glycine, and each B occurring in the subregion refers to another particular N-substituted glycine, but A and B are different from each other. Accordingly, C is an N-substituted glycine that is different from either A or B. The subregion sequence is meant to be read from left to right in the amino to carboxy direction. In some embodiments, when A is a hydrophobic residue, then B is a hydrophilic residue, and vice versa. In some embodiments, the peptoid subregion is homogenous, i.e., comprises only one type of N-substituted glycine. In some embodiments, when A is an aliphatic residue, B is a cyclic residue. In some embodiments, when B is an aliphatic residue, A is a cyclic residue. In some embodiments, both A and B are aliphatic. In some embodiments, A and B are aliphatic and C is cyclic. In some embodiments, all the N-substituted glycines are aliphatic such as for subregion -AABA-, e.g., —(N-(2-methoxyethyl) glycine)$_2$-N-(4-aminobutyl)glycine-(N-(2-methoxyethyl) glycine)—, where A is N-(2-methoxyethyl)glycine and B is N-(4-aminobutyl)glycine.

In some embodiments, the peptoid region comprises a tripeptoid, i.e., three contiguous N-substituted glycines. Example tripeptoid peptoid subregions include —-(N-(2-(4-hydroxyphenyl)ethyl)glycine)$_2$-N-(4-guanidinobutyl)glycine-, —N-(4-aminobutyl)glycine-(V)$_2$—, where V is N-benzylglycine or N-(2-methoxyethyl)glycine, —N-benzylglycine-W—N-benzylglycine-, where W is N-(4-aminobutyl)glycine or N-(2-methoxyethyl)glycine, and —N-(4-aminoethyl)glycine-(N-(2-(4-methoxyphenyl)ethyl) glycine)$_2$-. In some embodiments, the tripeptoid subregion comprises at least one aliphatic and one cyclic residue, e.g., (A)$_2$—B, B$_2$-A, or B-A-B where A is an aliphatic residue and B is a cyclic residue.

In some embodiments, the peptoid subregion is a dipeptoid such as a N-(4-aminobutyl)glycine-(S)—N-(1-phenylethyl) glycine dipeptoid.

In some embodiments, the peptoid reagent comprises a sequence selected from SEQ ID NO: 229, 230, 231, 232, 233, 234, 235, 236, 237, 238, 239, 240, or 241, shown hereinbelow. In some embodiments, the peptoid reagent comprises a sequence selected from SEQ ID NO: 229, 230, 232, 233, 234, 235, 237, 238, 239, or 240. In some embodiments, the peptoid reagent comprises a sequence selected from SEQ ID NO: 229, 230, 235, 237, 238, 239, or 240. In some embodiments, the peptoid reagent comprises a sequence selected from SEQ ID NO: 230, 237, 238, 239, or 240. In some embodiments the invention comprises peptoid reagent I, II, VII, IX, X, XIa, XIb, XIIa, or XIIb. In some embodiments the invention comprises peptoid reagent II, IX, X, XIa, XIb, XIIa, or XIIb.

Peptoid reagents of the invention can be engineered in concept by replacing amino acids of a peptide fragment of a conformational disease protein with N-substituted glycines. Preferably, the parent peptide fragment is capable of binding to a conformational disease protein. Example parent peptide fragments include those having sequences of SEQ ID Nos. 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, and 228.

In some embodiments, at least one non-proline residue of the peptide fragment is replaced by an N-substituted glycine to form the peptoid reagent. In some embodiments, at least three amino acid residues of the peptide fragment are each replaced by N-substituted glycines to form the peptoid reagent. In some embodiments, at least five amino acid residues are replaced by N-substituted glycines.

In some such embodiments, the conformational disease protein is a prion protein. For example, the peptide fragment can be derived from any of those regions corresponding to residues 23-43 or 85-156 (e.g., 23-30, 86-111, 89-112, 97-107, 113- 135, and 136-156) numbered according to the mouse prion sequence shown in SEQ ID NO: 2 of co-owned patent applications U.S. Ser. No. 10/917,646, filed Aug. 13, 2004, U.S. Ser. No. 11/056,950, filed Feb. 11, 2005, and International Application PCT/US2004/026363, filed Aug. 13, 2004, all entitled "Prion-Specific Peptide Reagents", each of which are incorporated herein in its entirety.

In some embodiments, the peptide fragment is selected from any one of SEQ ID Nos. 14, 50, 51, 52, 12, 72, 68 or 115 through 219. In some embodiments, the peptide fragment is selected from any one of SEQ ID Nos. 14, 50, 51, 52, or 161 through 219. In some embodiments, the peptide fragment is selected from any one of SEQ ID Nos. 12, 72, 68 or 115 through 160. In some embodiments, the peptide fragment is selected from any one of SEQ ID Nos. 14, 50, or 68.

As a starting point, the amino acid residues in the peptide fragment can be replaced with N-substituted glycines according to a replacement scheme wherein hydrophobic amino acid residues are replaced with hydrophobic N-substituted glycines and hydrophilic amino acid residues are replaced with hydrophilic N-substituted glycines. In some embodiments, amino acid monomers of peptides can be replaced with N-substituted glycines according to the following replacement scheme to form a modified peptide:

(a) Ala, Gly, Ile, Leu, Pro, and Val can be replaced by N-(alkyl)glycine, N-(aralkyl)glycine, or N-(heteroarylalkyl)glycine;
(b) Asp, Asn, Cys, Gln, Glu, Met, Ser, and Thr can be replaced by N-(hydroxyalkyl)glycine, N-(alkoxy)glycine, N-(aminoalkyl)glycine, or N-(guanidinoalkyl)glycine;
(c) Phe, Trp, and Tyr can be replaced by N-(aralkyl)glycine, N-(heteroarylalkyl)glycine, N-(hydroxyaralkyl) glycine, or N-(alkoxyaralkyl)glycine; and
(d) Arg, His, and Lys can be replaced by N-(aminoalkyl) glycine or N-(guanidinoalkyl)glycine.

The modified peptide can be tested for binding to the pathogenic form of a prion protein according to methods described herein. Additional replacements, according to the above scheme, of amino acid monomers with N-substituted glycines can be made and retested until suitable binding is obtained (i.e., peptoid reagents that interact preferentially with the pathogenic form of the prion).

Methods for making peptoids are disclosed in U.S. Pat. Nos. 5,811,387 and 5,831,005, each of which is incorporated herein by reference in its entirety, as well as methods disclosed herein.

A peptoid reagent of the invention comprises monomers, multimers, cyclized molecules, branched molecules, linkers and the like. Multimers (i.e., dimers, trimers and the like) of any of the sequences described herein or biologically functional equivalents thereof are also contemplated. The multimer can be a homomultimer, i.e., composed of identical monomers, e.g., each monomer is the same peptoid sequence such as SEQ ID NO: 229, hereinbelow. Alternatively, the multimer can be a heteromultimer, i.e., all the monomers comprising the multimer are not identical.

Multimers can be formed by the direct attachment of the monomers to each other or to substrate, including, for example, multiple antigenic peptides (MAPS) (e.g., symmetric MAPS), peptides attached to polymer scaffolds, e.g., a PEG scaffold and/or peptides linked in tandem with or without spacer units. Alternatively, a linker can be added to the monomers to join them to form a multimer. Non-limiting examples of multimers using linkers include, for example, tandem repeats using glycine linkers, MAPS attached via a linker to a substrate and/or linearly linked peptides attached via linkers to a scaffold. Linker moieties may involve using bifunctional spacer units (either homobifunctional or heterobifunctional) as are known to one of skill in the art.

In some embodiments, the peptoid reagent interacts with the conformational disease protein of a prion-related disease, where the pathogenic form of the conformational disease protein is $PrP^{Sc}$, and the nonpathogenic form of the conformational disease protein is $PrP^{C}$. In some embodiments, the peptoid reagent is specific for $PrP^{Sc}$ from more than one species, for example, the peptoid reagent can be specific for prion protein from two or more of human, cow, sheep, deer, elk, goat, mouse, or hamster. In some embodiments, the peptoid reagent is specific for $PrP^{Sc}$ from a single species.

In some embodiments, the peptoid reagent interacts with the pathogenic form of the conformational disease protein with an affinity of at least about 2 fold; 5 fold; 10 fold; 20 fold; 50 fold; 100 fold; 200 fold; 500 fold; or 1000 fold greater than that for the nonpathogenic form of the conformational disease protein. In some embodiments, the affinity is at least about 10 fold greater than that for the nonpathogenic form of the conformational disease protein. In some embodiments, the affinity is at least 100 fold greater.

The invention further provides a complex comprising one or more peptoid reagent as described herein and a prion protein. In some embodiments, the complex comprises a peptoid reagent described herein and a pathogenic prion. In some embodiments, the pathogenic prion is $PrP^{Sc}$. In some embodiments, the complex comprises the pathogenic prion and/or a peptoid reagent, prion-binding reagent or ligand, which optionally is labeled. As used herein, the term "complex" means an association between prion, pathogenic or non-pathogenic, and a peptoid reagent and/or a prion-binding reagent. Thus, a complex is not necessarily an association between a prion and a peptoid reagent, and can be an association between a prion and a prion-binding reagent. The molecules in the complex will be bound together by sufficient intermolecular forces, e.g., ionic, hydrophobic, hydrogen bonding, van der Waals, etc., to enable the complex to function as a single unit for the purposes of the methods and compositions described herein Compositions The present invention further provides a composition comprising a peptoid reagent of the invention, as described herein. In some embodiments, the composition comprises a peptoid reagent and a sample such as a biological sample. The biological sample is a sample prepared from a living or once-living organism. Non-limiting examples of biological samples are organs (e.g., brain, liver, and kidney), cells, whole blood, blood fractions, blood components, plasma, platelets, serum, cerebrospinal fluid (CSF), brain tissue, nervous system tissue, muscle tissue, muscle and fatty tissue (e.g., flesh), bone marrow, urine, tears, non-nervous system tissue, foods that are sourced from a living or once-living organism such as beef, pork, or veal, and any other organic matter such as plant materials. The biological sample can be obtained during a health related procedure such as a blood donation or screening, biopsy, autopsy, or necropsy, or during a process or procedure during food preparation such as animal selection and slaughter and quality assurance testing of finish product.

The invention also provides a composition comprising a solid support and at least one peptoid reagent of the invention. The solid support can be, for example, nitrocellulose, polystyrene, polypropylene, latex, polyvinyl fluoride, diazotized paper, nylon membranes, activated beads and/or magnetically responsive beads, or polyvinylchloride; polypropylene, polystyrene latex, polycarbonate, nylon, dextran, chitin, sand, silica, pumice, agarose, cellulose, glass, metal, polyacrylamide, silicon, rubber, or polysaccharides; diazotized paper; or any materials used for solid phase synthesis, affinity separations, purifications, hybridization reactions, immunoassays and other such applications. The support can be a particulate or can be in the form of a continuous surface and includes membranes, mesh, plates, pellets, slides, disks, capillaries, hollow fibers, needles, pins, chips, solid fibers, gels (e.g., silica gels) and beads, (e.g., pore-glass beads, silica gels, polystyrene beads optionally cross-linked with divinylbenzene, grafted co-poly beads, polyacrylamide beads, latex beads, dimethylacrylamide beads optionally cross-linked with N-N'-bis-acryloylethylenediamine, iron oxide magnetic beads, and glass particles coated with a hydrophobic polymer). In some such embodiments, the solid support is selected from the group consisting of nitrocellulose, polystyrene latex, polyvinyl fluoride, diazotized paper, nylon membranes, activated beads, and magnetically responsive beads. The peptoid reagent is attached to the solid support by any suitable method. Many such methods are well-known in the art and are described herein. Whatever method is chosen, the attachment of peptoid reagent to solid support should be stable enough to prevent any significant loss of peptoid reagent from the solid support in the practice of any of the methods of detection described herein.

In some embodiments, the composition comprising the peptoid reagent is a pharmaceutical composition, i.e., pharmaceutically acceptable and pharmacologically acceptable. In some embodiments, the composition further comprises at least one pharmaceutically acceptable carrier or excipient. The pharmaceutical carrier can be a solid or liquid. A solid carrier can include one or more substances that may also act as a flavoring agent, sweetening agent, lubricant, solubilizer, suspending agent, filler, glidant, compression aid, binder, or tablet-disintegrating agent; it can also be an encapsulating material. In powders, the carrier comprises a finely divided solid that is in admixture with the finely divided peptoid reagent. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art.

An excipient is an ingredient that provides bulk, imparts satisfactory processing and compression characteristics, helps control the dissolution rate, and/or otherwise gives additional desirable physical characteristics to the core material. Excipients, for example, are diluents, binders, lubricants and disintegrants well known to those of ordinary skill in the art, as described, for example, in the *Handbook of Pharmaceutical Excipients*, American Pharmaceutical Association, Washington, D.C. and The Pharmaceutical Society of Great Britain, London, England (1986), herein incorporated by reference in its entirety. Suitable excipients include, for example, cellulosic material, such as, Hypromellose, HPC, HEC, carboxymethylcellulose, microcrystalline cellulose, ethyl cellulose, methyl cellulose, and their derivatives and salts; other organic compounds, such as PEG, talc, lactose and other sugars such as sucrose, glucose, fructose, maltose, and maltodextrin, acacia, dextrin, alginic acid, ethylcellulose resin, gelatin, guar gum, methylcellulose, pregelatinized starch, sodium alginate, starch, zein, polyvinylpyrrolidone, vinylpyrrolidine-vinyl acetate copolymer, vinyl acetate-crotonic acid copolymer and ethyl acrylate-methacrylate acid copolymer; plasticizers such as propylene glycol, glycerin, trimethylolpropane, PEG polymers, dibutyl sebacate, acetylated monoglycerides, diethylphthalate, triacetin, glyceryltriacetate, acetyltrietyhyl citrate and triethyl citrate; and lubricants, such as talc, magnesium stearate, calcium stearate, stearic acid, hydrogenated vegetable oils, magnesium lauryl sulfate, sodium benzoate, a mixture of sodium benzoate and sodium acetate, sodium chloride, leucine, and Carbowax® 4000.

A pharmaceutical composition of the invention can also be administered in conjunction with other molecules, for example, antigens and immunoregulatory agents such as immunoglobulins, cytokines, lymphokines, and chemokines, including but not limited to interleukin 2 (IL-2), modified IL-2 (cysl25-serl25), granulocyte macrophage colony-stimulating factor (GM-CSF), interleukin 12 (IL-12), alpha- or gamma-interferon, chemokine IP-10, and β chemokines such as RANTES, MIP1-α, and MIP1-β. When administered in conjunction, the composition can be administered simultaneously or sequentially with the other molecule; and if simultaneously, either as a single dosage unit such as a mixture comprising the composition and other molecule, or as separate and distinct dosage units, each unit comprising either the composition or the other molecule.

Pharmaceutical compositions as described herein can comprise a therapeutically effective amount of the peptoid reagent. As used herein, "therapeutically effective amount" means an amount that will induce a protective and/or therapeutic response in the uninfected, infected, exposed or unexposed animal such as a mammal, e.g., human or non-human, to which it is administered. A therapeutically effective amount will vary depending on the animal being treated, the age and general condition of the animal being treated, the capacity of the animal's immune system to synthesize antibodies, the degree of protection desired, the severity of the condition being treated, the particular composition selected and its mode of administration, among other factors. An ordinarily skilled medical provider can determine the therapeutically effective amount, as well as, the appropriate dose and frequency of administration(s) to achieve an optimum clinical result. For example, the composition of the invention can be administered in a single dose, or as part of an administration regime such as multiple doses, and can be administered daily, weekly, monthly, annually, semi-annually, biannually, and the like. A pharmaceutical composition can be administered by various modes, for example, but without limitation, intramuscularly, intramucosally, subcutaneously, intradermally, transdermally, transcutaneously, intravaginally, intraperitoneally, intrarectally, orally, nasally, rectally, ocularly, intestinally, and/or intravenously. A composition can be adapted for administration; e.g., for oral administration, it can be in the form of tablets or capsules, optionally enteric-coated, liquid, or controlled-release; and for intranasal administration, it can be in the form of a nasal spray, nasal drops, gel or powder. The dosage regime may include a first dose and a second dose. The first dose such as a priming dose and a second dose such as a booster can be administered mucosally, parenterally, or a combination thereof. Although examples of routes of administration are provided, the appropriate route of administration, and dosage, are generally determined on a case-by-case basis by the attending physician. Such determinations are routine to one of ordinary skill in the art (See e.g., *Harrison's Principles of Internal Medicine* (1998), Fauci et al., eds. 14$^{th}$ ed. New York: McGraw Hill.)

Detection

The present invention further provides methods for detecting the presence of prion proteins, particularly pathogenic prion proteins. The detection methods rely on the property of the peptoid reagents of the invention to interact preferentially with pathogenic prion forms. The detection methods can be used, for example, with methods for detecting a conformational disease protein, especially a pathogenic prion protein, in a sample, methods for diagnosing a prion-related disease (e.g., in human or non-human animals), methods for ensuring a substantially PrP$^{SC}$-free blood supply, blood products supply, or food supply, methods for analyzing organ and tissue samples for transplantation, methods for monitoring the decontamination of surgical tools and equipment, as well as any other situation where knowledge of the presence or absence of the pathogenic prion is important.

Thus, the present invention relates to a method for detection of the presence of a pathogenic prion in a sample, which comprises contacting the sample with a first peptoid reagent of the invention under conditions that allow binding of the peptoid reagent to the pathogenic prion, if present, to form a complex, and detecting the formation of the complex, the formation of the complex being indicative of the presence of the pathogenic prion. Typical conditions that allow binding of the peptoid reagent to the pathogenic prion are described in the examples herein. Other suitable binding conditions can be readily determined by one of ordinary skill in the art.

The method of detection of pathogenic prion in a sample also can comprise contacting the sample with a first peptoid reagent of the invention under conditions that allow binding of the first peptoid reagent to the pathogenic prion, if present, to form a first complex, contacting the first complex with a second peptoid reagent of the invention, optionally detectably labeled, under conditions that allow binding of the second peptoid reagent to the pathogenic prion of the first complex to form a second complex, and detecting formation of the second complex, the formation of the second complex being indicative of the presence of the pathogenic prion. The second complex can comprise the second peptoid reagent and the pathogenic prion, and optionally, the first peptoid reagent.

In a further embodiment, the method comprises contacting the sample with a first peptoid reagent of the invention under conditions that allow binding of the first peptoid reagent to the pathogenic prion, if present, to form a first complex, removing any unbound sample, contacting the first complex with a second peptoid reagent of the invention, optionally detectably labeled, under conditions that allow binding of the second peptoid reagent to the pathogenic prion of the first complex to form a second complex, and detecting formation of the second complex, the formation of the second complex being indicative of the presence of the pathogenic prion. The first peptoid reagent optionally comprises a solid support which aids in separation of the first complex from the unbound sample.

Further, the detection method of the invention can comprise contacting the sample with a first peptoid reagent of the invention under conditions that allow binding of the first peptoid reagent to the pathogenic prion, if present, to form a first complex, removing unbound sample, dissociating the pathogenic prion from the first complex thereby providing dissociated pathogenic prion, contacting the dissociated pathogenic prion with a second peptoid reagent of the invention, optionally detectably labeled, under conditions that allow binding of the second peptoid reagent to the dissociated pathogenic prion to form a second complex, and detecting the formation of the second complex, the formation of the second complex being indicative of the presence of the pathogenic prion. Dissociation of the first complex can be achieved by any conventional method for disrupting protein binding interactions, e.g., addition of a salt or chaotropic agent, increase in temperature, addition of a detergent or denaturant and mechanical disruption, and may also comprise treatment at a high or low pH as described herein.

The method of detection of pathogenic prion in a sample also can comprise contacting the sample with a first peptoid reagent of the invention under conditions that allow binding of the first peptoid reagent to the pathogenic prion, if present, to form a first complex, contacting the first complex with a prion-binding reagent (described herein), optionally detectably labeled, under conditions that allow binding of the prion-binding reagent to the pathogenic prion of the first complex to form a second complex, and detecting formation of the second complex, the formation of the second complex being indicative of the presence of the pathogenic prion. The second complex can comprise the prion-binding reagent and the pathogenic prion, and optionally, the first peptoid reagent.

In a further embodiment, the method comprises contacting the sample with a first peptoid reagent of the invention under conditions that allow binding of the first peptoid reagent to the pathogenic prion, if present, to form a first complex, removing any unbound sample, contacting the first complex with a prion-binding reagent, optionally detectably labeled, under conditions that allow binding of the prion-binding reagent to the pathogenic prion of the first complex to form a second complex, and detecting formation of the second complex, the formation of the second complex being indicative of the presence of the pathogenic prion. The first peptoid reagent optionally comprises a solid support which aids in separation of the first complex from the unbound sample.

Further, the detection method of the invention can comprise contacting the sample with a first peptoid reagent of the invention under conditions that allow binding of the first peptoid reagent to the pathogenic prion, if present, to form a first complex, removing unbound sample, dissociating the pathogenic prion from the first complex thereby providing dissociated pathogenic prion, contacting the dissociated pathogenic prion with a prion-binding reagent, optionally detectably labeled, under conditions that allow binding of the prion-binding reagent to the dissociated pathogenic prion to form a second complex, and detecting the formation of the second complex, the formation of the second complex being indicative of the presence of the pathogenic prion.

In a further embodiment, the detection method of the invention can comprise contacting the sample with a first peptoid reagent of the invention under conditions that allow binding of the first peptoid reagent to the pathogenic prion, if present, to form a first complex, removing unbound sample, dissociating the pathogenic prion from the first complex thereby providing dissociated pathogenic prion, contacting the dissociated pathogenic prion with a prion-binding reagent under conditions that allow binding of the prion-binding reagent to the dissociated pathogenic prion to form a second complex, and detecting the formation of the second complex using a second prion-binding reagent, optionally detectably labeled, the formation of the second complex being indicative of the presence of the pathogenic prion.

The dissociated pathogenic prion is preferably denatured during or subsequent to the dissociation from the first complex and before the formation of the second complex. Typically, the agents that effect dissociation of the pathogenic prion from the complex (e.g., chaotropic agents, heat, high or low pH) will promote denaturation of the pathogenic prion protein; however, if desirable, dissociation of the pathogenic prion from the complex can be accomplished without denaturing the protein, for example using low concentration (e.g., 0.4 to 1.0 M) of guanidinium hydrochloride or guanidinium isothiocyanate. See, WO2006076497 (International Application PCT/US2006/001090) for additional conditions for dissociating the pathogenic prion from the complex without denaturing the prion protein.

In another embodiment, the detection method comprises contacting the sample with a prion-binding reagent under conditions that allow binding of the prion-binding reagent to the pathogenic prion, if present, to form a first complex, removing unbound sample, contacting the complex with a peptoid reagent of the invention, optionally detectably labeled, under conditions that allow binding of the peptoid reagent to the pathogenic prion of the first complex to form a second complex, and detecting the formation of the second complex, the formation of the second complex being indicative of the presence of the pathogenic prion. The prion-binding reagent is optionally provided on a solid support.

In some embodiments, the dissociating step comprises contacting the bound pathogenic prion protein with a salt or a chaotropic agent such as, for example, guanidium thiocyanate (GdnSCN) or guanidinium hydrochloride (GdnHCl). Example suitable concentrations of GdnSCN or GdnHCl are between about 3M and about 6M.

In some embodiments, the dissociating step comprises exposing the bound pathogenic prion protein to high or low pH, whereby the dissociated pathogenic prion protein is denatured. For example, the pH can be above 12 or below 2. In some embodiments, the pH is between 12.5 and 13.0. A high pH can achieved by the addition of NaOH to make a concentration of 0.05 N to 0.15 N. Exposure to high or low pH can be carried out for no more than 15 minutes or no more than 10 minutes. In some embodiments, the high or low pH is neutralized to between 7.0 and 7.5 such as by the addition of phosphoric acid or a sodium salt thereof.

A "prion-binding reagent" is a reagent that binds to a prion protein in some conformation, e.g., the prion-binding reagent may bind to one or more of a denatured form of the prion protein, the $PrP^C$ form (non-pathogenic isoform), or the $PrP^{SC}$ (pathogenic isoform). Some such prion-binding reagents will bind to more than one of these prion protein forms. Prion-binding reagents have been described and include, for example, anti-prion antibodies (described, inter alia, in Peretz et al. 1997 *J. Mol. Biol.* 273: 614; Peretz et al. 2001 *Nature* 412: 739; Williamson et al. 1998 *J. Virol.* 72: 9413; Polymenidou et al. The Lancet 2005 4:805; U.S. Pat. No. 4,806,627; U.S. Pat. No. 6,765,088; and U.S. Pat. No. 6,537548), motif-grafted hybrid polypeptides (see, W003/085086), certain cationic or anionic polymers (see, WO03/073106), certain peptides that are "propagation catalysts" (see, WO02/097444), prion specific peptide reagents (see, for example, WO2006/076687 and US20060035242) and plasminogen. In all of the methods utilizing a prion-binding reagent, preferred prion-binding reagents are anti-prion antibodies Further still, the detection method can comprise providing a solid support comprising a peptoid reagent of the invention, combining the solid support with a detectably labeled ligand, wherein the peptoid reagent of the support has a weaker binding affinity for the ligand than for the pathogenic prion, to form a first complex, combining the sample with the first complex under conditions that allow binding of the pathogenic prion, if present in the sample, to the peptoid reagent of the first complex, thereby replacing the detectably labeled ligand of the first complex and forming a second complex comprising the peptoid reagent and the pathogenic prion, and detecting the formation of the second complex, the formation of the second complex being indicative of the presence of the pathogenic prion.

For use in the methods for detecting the presence of a pathogenic prion in a sample, the sample can be anything known to, or suspected of, containing a pathogenic prion protein. In some embodiments, the sample is suspected of containing a pathogenic prion, e.g., $PrP^{SC}$. In some embodiments, the sample is a biological sample (i.e., a sample prepared from a living or once-living organism), or a non-biological sample. In some embodiments, the sample is a biological sample. Non-limiting examples of biological samples are organs (e.g., brain, liver, and kidney), cells, whole blood, blood fractions, blood components, plasma, platelets, serum, cerebrospinal fluid (CSF), brain tissue, nervous system tissue, muscle tissue, muscle and fatty tissue (e.g., flesh), bone marrow, urine, tears, non-nervous system tissue, foods that are sourced from a living or once-living organism, and any other organic matter such as plant materials. In some embodiments, the biological sample comprises whole blood, blood fractions, blood components, plasma, platelets, or serum. In some embodiments, the biological sample is obtained from a biopsy, autopsy or necropsy. In some embodiments, the sample is non-biological. Non-limiting examples of non-biological samples include pharmaceuticals, cosmetics and personal care products, and foods that are not sourced from a living or once-living organism, and the like. The sample may be pretreated in ways that are conventional (e.g., heating, grinding, sonication, exposure to certain digestive enzymes) in order to ensure contact between the pathogenic prion protein that may be present in the sample and the peptoid reagent.

The detection methods of the invention can utilize any of the peptoid reagents described herein. In some embodiments, the detection method of the present invention utilizes a peptoid reagent that interacts with a conformational disease protein such as a prion protein, preferentially with a pathogenic form as compared to a nonpathogenic form of the conformational disease protein, having a formula of:

wherein:

each Q is independently an amino acid or an N-substituted glycine, and -(Q)$_n$- defines a peptide region;

$X^a$ is H, (C$_1$-C$_6$)alkyl, cycloalkyl, aryl, aralkyl, heteroaryl, heteroarylalkyl, heterocycloalkyl, (C$_1$-C$_6$)acyl, amino (C$_{1-6}$)acyl, an amino acid, an amino protecting group, or a polypeptide of 2 to about 100 amino acids, wherein $X^a$ is optionally substituted by a conjugate moiety that is optionally attached through a linker moiety;

$X^b$ is H, $(C_1-C_6)$alkyl, aryl, aralkyl, heteroaryl, heteroarylalkyl, heterocycloalkyl, amino, alkylamino, dialkylamino, hydroxyl, $(C_1-C_6)$alkoxy, aryloxy, aralkoxy, a carboxy protecting group, an amino acid, or a polypeptide of 2 to about 100 amino acids, wherein $X^b$ is optionally substituted by a conjugate moiety that is optionally attached through a linker moiety; and n is 3 to about 30; where at least about 50% of the peptoid region -$(Q)_n$- comprises N-substituted glycines.

In some such embodiments, n is about 4 to about 30, preferably about 5 to about 30, and the peptoid region -$(Q)_n$- comprises at least one subregion independently selected from:
- (a) -AABA-;
- (b) -AABAB-
- (c) -ABACC-;
- (d) -AAAAA-;
- (e) -ABCBA-;
- (f) -AABCA-; or
- (g) -ABABA-;

where A, B, and C are each different N-substituted glycines.

In some embodiments of the method of detection, the peptoid reagent comprises an amino-terminal region, a carboxy-terminal region, and at least one peptoid region between the amino-terminal region and the carboxy-terminal region, where the peptoid region comprises about 3 to about 30 N-substituted glycines and optionally one or more amino acids. In some such embodiments, the peptoid region comprises a peptoid subregion selected from:
- (a) -AABA-;
- (b) -AABAB-
- (c) -ABACC-;
- (d) -AAAAA-;
- (e) -ABCBA-;
- (f) -AABCA-; and
- (g) -ABABA-;

where A, B, and C are each different N-substituted glycines.

In some embodiments of the detection method of the present invention, the peptoid reagent comprises a peptoid analog of a 3 to 30 amino acid peptide fragment of the conformational disease protein, where the peptide fragment is selected from the group of sequences consisting of SEQ ID Nos. 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, and 228 where:
- (a) at least one non-proline residue of the peptide fragment is replaced by an N-substituted glycine to form the peptoid analog; or
- (b) at least five amino acid residues of the peptide fragment are each replaced by an N-substituted glycine to form the peptoid analog.

In some embodiments of the above method, the replacement of any one or more amino acid residue of the peptide fragment with an N-substituted glycine corresponds to the following replacement scheme:
- i) Ala, Gly, Ile, Leu, Pro, and Val are replaced by N-(alkyl)glycine, N-(aralkyl)glycine, or N-(heteroarylalkyl)glycine;
- ii) Asp, Asn, Cys, Gln, Glu, Met, Ser, and Thr are replaced by N-(hydroxyalkyl)glycine, N-(alkoxy)glycine, N-(aminoalkyl)glycine, or N-(guanidinoalkyl)glycine;
- iii) Phe, Trp, and Tyr are replaced by N-(aralkyl)glycine, N-(heteroarylalkyl)glycine, N-(hydroxyaralkyl)glycine, or N-(alkoxyaralkyl)glycine; and
- iv) Arg, His, and Lys are replaced by N-(aminoalkyl)glycine or N-(guanidinoalkyl)glycine.

In some such embodiments, the peptoid reagent comprises a peptoid analog of a 5 to 30 amino acid peptide fragment of the conformational disease protein as described above.

In some embodiments of the method for detecting the presence of a pathogenic prion in a sample, the peptoid reagent comprises a sequence as described herein, for example, having a sequence selected from the group consisting of SEQ ID NOs: 229, 230, 231, 232, 233, 234, 235, 236, 237, 238, 239, 240, and 241. In some embodiments, the peptoid reagent comprises a sequence selected from SEQ ID NO: 229, 230, 232, 233, 234, 235, 237, 238, 239, or 240. In some embodiments, the peptoid reagent comprises a sequence selected from SEQ ID NO: 229, 230, 235, 237, 238, 239, or 240. In some embodiments, the peptoid reagent comprises a sequence selected from SEQ ID NO: 230, 237, 238, 239, or 240. In some embodiments the method of the invention utilizes one or more of peptoid reagent I, II, VII, IX, X, XIa, XIb, XIIa, or XIIb. In some embodiments the method of the invention utilizes one or more of peptoid reagent II, IX, X, XIa, XIb, XIIa, or XIIb. In some embodiments, the peptoid reagent used in the method comprises a sequence selected from SEQ ID NOs: 229, 236, 231, 232, 233, 234 or 235. In some embodiments, the peptoid reagent comprises a sequence selected from SEQ ID NOs: 230, 237, 238, 239, or 240. In some such embodiments, the peptoid reagent comprises SEQ ID NO: 230, 237 or 240. In some such embodiments, the peptoid reagent comprises SEQ ID NO: 240.

In some embodiments, the method for detecting the presence of a pathogenic prion in a sample comprises contacting the sample with a first peptoid reagent of the invention under conditions that allow binding of the first peptoid reagent to the pathogenic prion, if present, to form a complex comprising the first peptoid reagent and the pathogenic prion protein, and detecting the presence of the pathogenic prion, if any, in the sample by its binding to the first peptoid reagent. The binding of the pathogenic prion to the first peptoid reagent can be detected by detecting the formation of the complex, the formation of the complex being indicative of the presence of the pathogenic prion. In general, in preferred embodiments of the method, the complex comprising the first peptoid reagent and the pathogenic prion protein is separated from the rest of the sample (that is, the unbound sample) prior to detection. The formation of the complex can be detected by detecting the pathogenic prion in the complex or by dissociating the complex (after separation from the unbound sample) and detecting the dissociated pathogenic prion. The dissociated pathogenic prion may or may not be in the pathogenic conformation. In some embodiments, the dissociated pathogenic prion is in a denatured prion conformation. The dissociated pathogenic prion can be detected in ways that are known in the art, e.g., by binding an anti-prion antibody that is specific for the appropriate prion isoform, and that are described further herein. Antibodies that recognize different prion isoforms have been described in the art (See, for example, U.S. Pat. Nos. 5,846,533; 6,765,088; 6,261,790; 4,806,627; 6,165,784; 6,528,269; EP891552, EP909388; Polymenidou et al. The Lancet 2005 4:805).

In a preferred embodiment of the above method, the pathogenic prion is dissociated from the complex with the peptoid reagent using a chaotropic agent, or by using high or low pH treatment as described herein.

Further, the method for detecting a pathogenic prion in a sample by first forming a complex with the prion-specific peptoid reagent can be followed by detection of the complex with an analytical method. The analytical method can comprise a method such as UV/Visible spectroscopy, FTIR, nuclear magnetic resonance spectroscopy, Raman spectroscopy, mass spectrometry, HPLC, capillary electrophoresis, surface plasmon resonance spectroscopy, Micro-Electro-Mechanical Systems (MEMS), or any other method known in the art.

In some embodiments, the peptoid reagent or the prion-binding reagent comprises a detectable label. Detectable labels suitable for use in the invention include, for example, any molecule capable of detection, such as defined hereinabove. In some embodiments, the label comprises an enzyme, radioisotope, toxin or fluorophore. Additionally, the detectable label may include an oligonucleotide tag, which can be detected by a method of nucleic acid detection including, e.g., polymerase chain reaction (PCR), transcription-mediated amplification (TMA), branched DNA (b-DNA), nucleic acid sequence-based amplification (NASBA), and the like. Preferred detectable labels include enzymes, especially alkaline phosphatase (AP), horseradish peroxidase (HRP), and fluorescent compounds. As is well known in the art, the enzymes are utilized in combination with a detectable substrate, e.g., a chromogenic substrate or a fluorogenic substrate, to generate a detectable signal.

In some embodiments of the detection methods of the invention, one or more peptoid reagent is attached to a solid support. A solid support, for purposes of the invention, can be any material that is an insoluble matrix and can have a rigid or semi-rigid surface to which a molecule of interest (e.g., peptoid reagents of the invention, prion proteins, antibodies, etc.) can be linked or attached. Exemplary solid supports include, but without limitation, those previously described hereinabove. Peptoid reagents, as described herein, can be attached to the support covalently, or by absorption, coupling or use of binding pairs. For example, the peptoid reagents can be readily coupled to the solid support using techniques well-known in the art. Immobilization to the support may be enhanced by first coupling the peptoid reagent to a protein such as when the protein has better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. The peptoid reagents also can be attached to the solid support through the interaction of a binding pair of molecules. One member of the binding pair is coupled to the solid support and the other member of the binding pair is attached to the peptoid reagent (before, during, or after synthesis). For example the support can comprise avidin or streptavidin and the peptoid reagent can comprise biotin. In addition to biotin-avidin and biotin-streptavidin, other suitable binding pairs for attaching the peptoid to the support include, without limitation, antigen-antibody, hapten-antibody, mimetope-antibody, receptor-hormone, receptor-ligand, agonist-antagonist, lectin-carbohydrate, Protein A-antibody Fc. Such binding pairs are well known (see, e.g., U.S. Pat. Nos. 6,551,843 and 6,586,193) and one of ordinary skill in the art would be competent to select suitable binding pairs and adapt them for use with the present invention. Alternatively, the peptoid reagents can be covalently attached to the solid support using conjugation chemistries that are well known in the art. Thiol containing peptoid reagents are directly attached to solid supports, e.g., carboxylated magnetic beads, using standard methods known in the art (See, e.g., Chrisey, L. A., Lee, G. U. and O'Ferrall, C. E. (1996). Covalent attachment of synthetic DNA to self-assembled monolayer films. *Nucleic Acids Research* 24(15), 3031-3039; Kitagawa, T., Shimozono, T., Aikawa, T., Yoshida, T. and Nishimura, H. (1980). Preparation and characterization of hetero-bifunctional cross-linking reagents for protein modifications. *Chem. Pharm. Bull.* 29(4), 1130-1135). Carboxylated magnetic beads are first coupled to a heterobifunctional cross-linker that contains a maleimide functionality (BMPH from Pierce Biotechnology Inc.) using carbodiimide chemistry. The thiolated peptide or peptoid is then covalently coupled to the maleimide functionality of the BMPH coated beads. When used in the embodiments of the detection methods of the invention, the solid support aids in the separation of the complex comprising the peptoid reagent of the invention and the pathogenic prion protein from the unbound sample. Particularly convenient magnetic beads for thiol coupling are Dynabeads® M-270 Carboxylic Acid from Dynal. The peptoid reagent may also comprise a linker, for example, one or more aminohexanoic acid moieties.

In some embodiments of the method for detecting the presence of a pathogenic prion in a sample, the method comprises contacting the sample with a first peptoid reagent of the invention under conditions that allow binding of the first peptoid reagent to the pathogenic prion, if present, to form a first complex, then contacting the first complex with a detectably labeled second peptoid reagent of the invention under conditions that allow binding of the second peptoid reagent to the pathogenic prion of the first complex to form a second complex, and then detecting the binding of the pathogenic prion to the second peptoid reagent. In some embodiments, binding of the pathogenic prion protein to the second peptoid reagent can be detected by detecting the formation of the second complex, the formation of the second complex being indicative of the presence of pathogenic prion. In some embodiments, the peptoid reagents are different. In some embodiments, the first and the second peptoid reagents are the same. In some embodiments, the first peptoid reagent comprises biotin. In further embodiments, the first peptoid reagent is attached to a solid support.

In some embodiments of the detection methods of the invention, the method comprises contacting the sample with a first peptoid reagent of the invention under conditions that allow binding of the first peptoid reagent to the pathogenic prion, if present, to form a first complex; removing unbound sample, which may include, e.g., nonpathogenic prion present in the sample; dissociating the pathogenic prion from the first complex, thereby providing dissociated pathogenic prion; contacting the dissociated pathogenic prion with a detectably labeled second peptoid reagent of the invention under conditions that allow binding of the second peptoid reagent to the dissociated pathogenic prion to form a second complex; and detecting the formation of the second complex, the formation of the second complex being indicative of the presence of pathogenic prion. In this embodiment, the dissociated pathogenic prion retains the pathogenic conformation.

In general, "dissociated pathogenic prion" or "dissociated prion" may include prion protein that retains the pathogenic conformation, as well as pathogenic prion protein that has been denatured, which denatured prion may not have either the pathogenic conformation or the normal cellular conformation, and may not be infectious.

Alternatively, when the peptoid reagents of the invention are used to directly capture the pathogenic prion protein to form a first complex and the first complex is separated from the unbound sample materials, as described above, a prion-binding reagent, which is optionally detectably-labeled, can be used to detect the pathogenic prion, either while the pathogenic prion is bound in the first complex or after the dissociation of the prion protein from the first complex. As mentioned previously herein, a prion-binding reagent is a reagent that binds to a prion protein in some conformation, e.g., the prion-binding reagent may bind to one or more of a denatured form of the prion protein, the $PrP^C$ form (non-pathogenic isoform), or the $PrP^{SC}$ (pathogenic isoform). Some such prion-binding reagents will bind to more than one of these prion protein forms. Prion-binding reagents have been described and include, for example, anti-prion antibodies (described, inter alia, in Peretz et al. 1997 *J. Mol. Biol.* 273: 614; Peretz et al. 2001 *Nature* 412: 739; Williamson et al. 1998 *J. Virol.* 72: 9413; Polymenidou et al. The Lancet 2005 4:805; U.S. Pat. Nos. 4,806,627; 6,765,088; and 6,537548), motif-grafted hybrid polypeptides (see, WO03/085086), certain cationic or anionic polymers (see, WO03/073106), certain peptides that are "propagation catalysts" (see, WO02/097444), prion specific peptide reagents (see, for example, WO2006/076687 and US20060035242) and plasminogen. If the particular prion-binding reagent used binds to a denatured form of the prion, it will be apparent that the pathogenic prion protein of the first complex should be denatured prior to detection with the prion-binding reagent. Prion binding reagents, particularly anti-prion antibodies, may be selective for prion proteins from particular animal species. Thus, it will be apparent that prion binding reagents will be chosen that have suitable binding properties in terms of the specificity for prion conformation and species specificity.

The peptoid reagent of the invention can thus be used either as a "capture" reagent for pathogenic prions in a sample or as a "detection" reagent for the captured pathogenic prion, or both as capture and as detection reagent. When the peptoid reagent is used for capture of the pathogenic prion, the captured prion can be removed from the rest of the sample (by virtue of the complex formed with the peptoid reagent) and the prion can be detected by conventional means (eg, ELISA, Western blot, immunoprecipitation, etc), either while still complexed to the peptoid reagent or after dissociation of the complex. The captured prion can alternatively be detected using a second peptoid reagent that is detectably labeled.

ELISA

A particularly preferred method for detecting a pathogenic prion in a sample combines the use of the peptoid reagents of the invention with an improved ELISA technique. The assay combines the power of the peptoid reagents to discriminate between the pathogenic and the non-pathogenic form of the prion proteins with an improved ELISA technique. Because the peptoid reagents interact preferentially with the pathogenic prion proteins, these reagents are used to separate and concentrate any pathogenic prion present in the sample. Unlike methods that utilize digestion with proteinase K to discriminate between the pathogenic and non-pathogenic isoforms, which typically results in some N-terminal digestion even of the pathogenic isoform, use of the peptoid reagents in the method of the invention results in the separation of full-length pathogenic prion proteins. Thus, anti-prion antibodies that recognize epitopes at the N-terminal end of the prion protein, e.g., epitopes in the region from residues 23-90, can be used for detection, as well as anti-prion antibodies that recognize epitopes from other regions of the prion protein. The N-terminal region of the prion protein from most species contains a repeated sequence (4 copies of octarepeat GQPHGGGS/W or 5 copies in bovine PrP). Antibodies binding within this region may exhibit increased avidity resulting in an increased sensitivity for the assay.

Once the pathogenic prion protein is separated from the non-pathogenic isoform (which is present in many biological samples) using the peptoid reagents as described above, the pathogenic prion protein can be dissociated from the peptoid reagent and detected in a number of ELISA formats, described herein. The pathogenic prion is typically denatured in the process of dissociation from the peptoid reagent, although not necessarily so. Denaturation of the captured $PrP^{SC}$ before performing the ELISA is preferable, as the majority of high affinity anti-prion antibodies bind the denatured form of PrP and many anti-prion antibodies that bind to the denatured PrP are known and commercially available. The dissociation and denaturation of the pathogenic prion can be accomplished using high concentrations of chaotropic agents, e.g., 3M to 6M of a guanidinium salt such as guanidinium thiocyanate or guanidinium HCl. The chaotropic agent must be removed or diluted before the ELISA is carried out because it will interfere with the binding of the anti-prion antibodies used in the ELISA. This results in additional washing steps or generation of large sample volumes, both of which are undesirable for rapid, high-throughput assays.

The present inventors have discovered that in some embodiments a preferable alternative to the use of a chaotropic agent for denaturation of the pathogenic prion protein, and dissociation from the peptoid reagent, is the use of high or low pH. The pathogenic prion protein is readily dissociated from the peptoid reagent and denatured by adding components that increase the pH to above 12 (e.g., NaOH) or to below 2 (e.g., $H_3PO_4$). Moreover, the pH can be easily readjusted to neutral by addition of small volumes of suitable acid or base, thus allowing the use directly in the ELISA without any additional washes and without increasing the sample volumes significantly.

The invention thus provides a method for detecting the presence of a pathogenic prion in a sample comprising: contacting the sample suspected of containing a pathogenic prion with a peptoid reagent that interacts preferentially with the pathogenic form of the prion protein under conditions that allow the binding of the peptoid reagent to the pathogenic prion protein, if present; removing unbound sample material; dissociating the pathogenic prion from the peptoid reagent; and detecting the presence of the dissociated pathogenic prion using a prion-binding reagent. It will be apparent that if the particular prion-binding reagent used binds to a denatured form of the prion that the "captured" pathogenic prion protein should be denatured prior to detection with the prion-binding reagent. Preferably, the prion-binding reagent is an anti-prion antibody.

Antibodies, modified antibodies and other reagents, that bind to prions, particularly to $PrP^C$ or to the denatured PrP, have been described and some of these are available commercially (see, e.g., anti-prion antibodies described in Peretz et al. 1997 J. Mol. Biol. 273: 614; Peretz et al. 2001 Nature 412: 739; Williamson et al. 1998 J. Virol. 72:9413; Polymenidou et al. 2005 Lancet 4:805; U.S. Pat. No. 6,765,088. Some of these and others are available commercially from, inter alia, InPro Biotechnology, South San Francisco, Calif., Cayman Chemicals, Ann Arbor Mich.; Prionics AG, Zurich; also see, WO 03/085086 for description of modified antibodies). Suitable antibodies for use in the method include without limitation 3F4 (U.S. Pat. No. 4,806,627), D18 (Peretz et al. J. Mol Biol. 1997 273:614), D13 (Peretz 1997, supra), 6H4 (Liu et al. J. Histochem. Cytochem. 2003 51:1065), MAB5242 (Chemicon), 7D9 (Kascsak et al. 1987 J. Virol. 61:3688), BDI115 (Biodesign International), SAF32, SAF53, SAF83, SAF84 (SAF antibodies available from SPI Bio, France), 19B10 (WO2004/4033628), 7VC (WO2004/4033628), 12F10 (SPI Bio), PRI308 (SPI Bio), 34C9 (Prionics AG), Fab HuM—P (Peretz et al. Nature 2001 412:739), POM 1 through POM 19 (Polymenidou et al. 2005, supra) Fab HuM—R1 (Peretz 1997, supra), and Fab HuM—R72 (Peretz 1997, supra). Other anti-prion antibodies can readily be generated by methods that are well-known in the art. Preferred anti-prion antibodies will be ones that bind to a denatured form of the pathogenic prion. Particularly preferred anti-prion antibodies will be ones that recognize epitopes at the N-terminal region of the prion protein. Some anti-prion antibodies are specific for prion protein from one or a limited number of animal species, others are capable of binding prion proteins from many animal species. It will be apparent to choose suitable anti-prion antibodies based upon the samples to be analyzed and the purpose of the testing.

In preferred embodiments, the peptoid reagent is provided on a solid support. The peptoid reagent can be provided on a solid support prior to contacting the sample or the peptoid reagent can be adapted for binding to the solid support after contacting the sample and binding to any pathogenic prion therein (e.g., by using a biotinylated peptoid reagent and a solid support comprising an avidin or streptavidin).

The invention thus additionally provides a method for detecting the presence of a pathogenic prion in a sample comprising:

(a) providing a first peptoid reagent on a first solid support;
(b) contacting the first solid support with a sample under conditions that allow pathogenic prion proteins, when present in the sample, to bind to the peptoid reagent to form a first complex;
(c) removing unbound sample material;
(d) dissociating the pathogenic prion proteins from the first complex; and
(e) detecting the dissociated pathogenic prions using a prion-binding reagent.

The peptoid reagent can be any of those described herein, preferably, the peptoid reagent is derived from a sequence selected from the group consisting of SEQ ID NO:229-241. The prion binding-reagent is further described herein. Preferably the prion-binding reagent is an anti-prion antibody. The first solid support is preferably a magnetic bead, more preferably a polystyrene/iron oxide bead.

Methods of attaching a peptoid reagent on a solid support are conventional in the art and are described elsewhere herein and include well-known methods of attaching proteins and peptides to various solid surfaces. The sample is contacted with the solid support comprising the peptoid reagent under conditions that allow the binding of any pathogenic prion proteins in the sample to bind to the peptoid reagent, forming a first complex. Such binding conditions are readily determined by one of ordinary skill in the art and are further described herein. Typically, the method is carried out in the wells of a microtiter plate or in small volume plastic tubes, but any convenient container will be suitable. The sample is generally a liquid sample or suspension and may be added to the reaction container before or after the peptoid reagent. Once the first complex is established, unbound sample material (that is, any components of the sample that have not bound to the peptoid reagent, including any unbound pathogenic prion protein) can be removed by separating the solid support from the reaction solution (containing the unbound sample materials) for example, by centrifugation, precipitation, filtration, magnetic force, etc. The solid support with the first complex may optionally be subjected to one or more washing steps to remove any residual sample materials before carrying out the next steps of the method.

Following the removal of unbound sample materials and any optional washes, the bound pathogenic prion proteins are dissociated from the first complex. This dissociation can be accomplished in a number of ways. In one embodiment, a chaotropic agent, preferably a guanidinium compound, e.g., guanidinium thiocyanate or guanidinium hydrochloride, is added to a concentration of between 3M and 6M. Addition of the chaotropic agent in these concentrations causes the pathogenic prion protein to dissociate from the peptoid reagent and also causes the pathogenic prion protein to denature.

In another embodiment, the dissociation is accomplished by either raising the pH to 12 or above ("high pH") or lowering the pH to 2 or below ("low pH"). Exposure of the first complex to either high or low pH results in the dissociation of the pathogenic prion protein from the peptoid reagent and causes the pathogenic prion protein to denature. In this embodiment, exposure of the first complex to high pH is preferred. A pH of between 12.0 and 13.0 is generally sufficient; preferably, a pH of between 12.5 and 13.0 is used; more preferably, a pH of 12.7 to 12.9; most preferably a pH of 12.9. Alternatively, exposure of the first complex to a low pH can be used to dissociate and denature the pathogenic prion protein from the peptoid reagent. For this alternative, a pH of between 1.0 and 2.0 is sufficient. Exposure of the first complex to either a high pH or a low pH is carried out for only a short time e.g. 60 minutes, preferably for no more than 15 minutes, more preferably for no more than 10 minutes. Longer exposures than this can result in significant deterioration of the structure of the pathogenic prion protein such that epitopes recognized by anti-prion antibodies used in the detection steps are destroyed. After exposure for sufficient time to dissociate the pathogenic prion protein, the pH can be readily readjusted to neutral (that is, pH of between about 7.0 and 7.5) by addition of either an acidic reagent (if high pH dissociation conditions are used) or a basic reagent (if low pH dissociation conditions are used). One of ordinary skill in the art can readily determine appropriate protocols and examples are described herein.

In general, to effect a high pH dissociation condition, addition of NaOH to a concentration of about 0.05 N to about 0.2 N is sufficient. Preferably, NaOH is added to a concentration of between 0.05 N to 0.15 N; more preferably, 0.1 N NaOH is used. Once the dissociation of the pathogenic prion from the peptoid reagent is accomplished, the pH can be readjusted to neutral (that is, between about 7.0 and 7.5) by addition of suitable amounts of an acidic solution, e.g., phosphoric acid; sodium phosphate monobasic.

In general, to effect a low pH dissociation condition, addition of $H_3PO_4$ to a concentration of about 0.2 M to about 0.7 M is sufficient. Preferably, $H_3PO_4$ is added to a concentration of between 0.3 M and 0.6 M; more preferably, 0.5 M $H_3PO_4$ is used. Once the dissociation of the pathogenic prion from the peptoid reagent is accomplished, the pH can be readjusted to neutral (that is, between about 7.0 and 7.5) by addition of suitable amounts of a basic solution, e.g., NaOH or KOH.

The dissociated pathogenic prion protein is then separated from the solid support comprising the peptoid reagent. This separation can be accomplished in similar fashion to the removal of the unbound sample materials described above except that the portion containing the unbound materials (now the dissociated pathogenic prion protein) is retained and the solid support material portion is discarded.

The dissociated pathogenic prion protein can be detected using prion-binding reagents. A number of such prion-binding agents are known and described herein. Preferred prion-binding reagents for detection of the dissociated pathogenic prion protein are anti-prion antibodies. A number of anti-prion antibodies have been described and many are commercially available, for example, Fab D18 (Peretz et al. (2001) *Nature* 412:739-743), 3F4 (available from Sigma Chemical St Louis Mo.; also, See, U.S. Pat. No. 4,806,627), SAF-32 (Cayman Chemical, Ann Arbor Mich.), 6H4 (Prionic AG, Switzerland; also, See U.S. Pat. No. 6,765,088), POMs 1 through 19 (Polymenidou et al. The Lancet 2005 4:805) and others described above and well-known in the art. The dissociated pathogenic prion proteins can be detected in an ELISA type assay, either as a direct ELISA or an antibody Sandwich ELISA type assay, which are described more fully below. Although the term "ELISA" is used to describe the detection with anti-prion antibodies, the assay is not limited to ones in which the antibodies are "enzyme-linked." The detection antibodies can be labeled with any of the detectable labels described herein and well-known in the immunoassay art.

In one embodiment of the method, the dissociated pathogenic prion protein is passively coated onto the surface of a second solid support. Methods for such passive coating are well known and typically are carried out in 100 mM NaHCO$_3$ at pH 8 for several hours at about 37° C. or overnight at 4° C. Other coating buffers are well-known (e.g, 50 mM carbonate pH 9.6, 10 mM Tris pH 8, or 10 mM PBS pH 7.2) The second solid support can be any of the solid supports described herein or well-known in the art; preferably the second solid support is a microtiter plate, e.g., a 96-well polystyrene plate. Where the dissociation has been carried out using a high concentration of chaotropic agent, the concentration of the chaotropic agent will be reduced by dilution by at least about 2-fold prior to coating on the second solid support. Where the dissociation has been carried out using a high or low pH, followed by neutralization, the dissociated pathogenic prion protein can be used for coating without any further dilution.

Once the dissociated pathogenic prion protein is coated onto the second solid support, the support can be washed to remove any components that are not adhered to the solid support. Anti-prion antibodies are added under conditions that allow for binding of the antibodies to the prion protein coated on the second solid support. If the dissociated pathogenic prion protein has been denatured prior to coating on the second solid support, the antibodies used will be ones that bind to the denatured form of the prion protein. Such antibodies include ones that are well known (such as those described above) as well as antibodies that are generated by well known methods, e.g., by using rPrP, PrP$^C$ or fragments thereof, to elicit an immune reaction in mice, rabbits, rats, etc. (See, U.S. Pat. Nos. 4,806,627; 6,165,784; 6,528,269; 6,379,905; 6,261,790; 6,765,088; 5,846,533; EP891552B1 and EP 909388B1). Anti-prion antibodies that recognize epitopes at the N-terminal end of the prion protein are particularly preferred, for example, antibodies that recognize epitopes within the region of residues 23-90.

Thus, the invention in one embodiment provides a method for detecting the presence of a pathogenic prion in a sample comprising:

(a) providing a first peptoid reagent on a first solid support;
(b) contacting the first peptoid reagent with a sample under conditions that allow pathogenic prion proteins, when present in the sample, to bind to the peptoid reagent to form a first complex;
(c) removing unbound sample material;
(d) dissociating the pathogenic prion proteins from the first complex;
(e) separating the dissociated pathogenic prion proteins from the first solid support;
(f) contacting the dissociated pathogenic prion proteins with a second solid support under conditions that allow the dissociated prion protein to adhere to the second solid support; and
(g) detecting the adhered pathogenic prions on the second solid support using a prion-binding reagent.

In this embodiment, the first solid support is preferably a magnetic bead; the second solid support is preferably a microtiter plate; the prion-binding reagent is preferably an anti-prion antibody, particularly 3F4, 6H4, SAF32 or one or more of the POM antibodies described in Polymenidou, supra. The prion-binding reagent is detectably labeled.

In another embodiment of the method, the dissociated pathogenic prion proteins are detected using an antibody sandwich type ELISA. In this embodiment, the dissociated prion protein is "recaptured" on a second solid support comprising a first anti-prion antibody. The second solid support with the recaptured prion protein, is optionally washed to remove any unbound materials, and then contacted with a second anti-prion antibody under conditions that allow the second anti-prion antibody to bind to the recaptured prion protein. The first and second anti-prion antibodies will typically be different antibodies and will preferably recognize different epitopes on the prion protein. For example, the first anti-prion antibody will recognize an epitope at the N-terminal end of the prion protein and the second anti-prion antibody will recognize an epitope at other than the N-terminal, or vice versa. The first antibody can be, for example, SAF32 which recognizes an epitope in the octarepeat region (residues 23-90) and the second antibody can be 3F4, which recognizes an epitope at residues 109-112; alternatively, the first antibody can be 3F4 and the second antibody can be SAF32. Other combinations of first and second antibody can be readily selected. In this embodiment, the second anti-prion antibody, but not the first anti-prion antibody, will be detectably labeled. When the dissociation of the pathogenic prion protein from the peptoid reagent is carried out using a chaotropic agent, the chaotropic agent must be removed or diluted by at least 15-fold prior to carrying out the detection assay. When the dissociation is effected using a high or low pH and neutralization, the dissociated prion can be used without further dilution. When the dissociated pathogenic prion protein is denatured prior to carrying out the detection, the first and second antibodies will both bind to the denatured prion protein.

The invention thus provides a method for detecting the presence of a pathogenic prion in a sample comprising:

(a) providing a first peptoid reagent as described herein on a first solid support;
(b) contacting the first peptoid reagent with a sample under conditions that allow pathogenic prion proteins, when present in the sample, to bind to the peptoid reagent to form a first complex;
(c) removing unbound sample material;
(d) dissociating the pathogenic prion proteins from the first complex, whereby the pathogenic prion protein is denatured;

(e) separating the dissociated denatured pathogenic prion proteins from the first solid support;

(f) contacting the dissociated denatured pathogenic prion proteins with a second solid support, wherein the second solid support comprises a first anti-prion antibody, under conditions that allow the dissociated prion protein to bind to the first anti-prion antibody; and (g) detecting the bound prion proteins on the second solid support with a second anti-prion antibody.

In this embodiment, the first solid support is preferably a magnetic bead; the second solid support is preferably a microtiter plate or a magnetic bead; the first and second anti-prion antibodies are preferably different antibodies; the first and second antibodies preferably bind to denatured prion protein; preferably, at least one of the first or second anti-prion antibodies recognizes an epitope at the N-terminal region of the prion protein. In some embodiments, the second anti-prion antibody is detectably labeled; in further embodiments, the second anti-prion antibody is enzyme labeled.

Any of the detection methods for a pathogenic prion described hereinabove can be used in a method to diagnose a prion-related disease.

Diagnosis and Treatment

The invention further provides methods of treating or preventing a prion-related disease that comprise administering to an animal one or more peptoid reagents, or compositions thereof, as described herein. The invention also provides methods for determining a level of prion-related disease infection in an animal, which can be used to make a diagnosis and assess the need for treatment or prevention. If treatment or prevention is necessary, it may or may not be for the prion-related disease. That is, if it is determined that no prion infection is present, treatment or prevention can be necessary for a non-prion-related disease, disorder, condition or symptom. Such a treatment can be, for example, a conventional medicament. The invention also provides methods of identifying the location of the prion-related infection.

The term "treatment" or "treating," as used herein, means curing, ameliorating or reversing the progress of a disease or disorder, or ameliorating or reversing one or more symptoms or side effects of such disease or disorder.

The term "administering," as used herein, means directly administering the peptoid reagent or composition thereof, which will provide an effectively therapeutic amount of the peptoid reagent in the receiving animal.

As used herein, the phrase "therapeutically effective amount" refers to the amount of active peptoid reagent, or composition, that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the method comprises obtaining a sample from the animal; detecting a presence of a pathogenic prion according to any of the detection methods of the invention; and determining the level of prion disease infection from the presence or absence of the pathogenic prion detected.

In some embodiments, a method of determining a location of a prion-related disease infection in an animal is provided, where the method comprises administering to the animal peptoid reagent of the invention, or composition thereof, where the peptoid reagent is linked to an imaging agent; and detecting the imaging agent, thereby localizing the prion-related disease infection in the animal.

In some embodiments of a method of treating or preventing a prion-related disease in an animal, the method comprises determining the presence of one or more pathogenic prions in the animal according to a detection method of the invention; then, administering one or more peptoid reagents of the invention, or compositions comprising the same, to the animal following a determination that a one or more pathogenic prions are present; or administering one or more conventional medicaments to the animal following a determination that a one or more pathogenic prions are not present. In some embodiments, the method comprises administering one or more conventional medicaments to the animal following the determination that a prion-related disease infection is present. In some embodiments, the sample for testing comprises organ matter, cells, whole blood, a blood fraction, a blood component, plasma, a platelet, serum, cerebrospinal fluid (CSF), brain tissue, nervous system tissue, muscle tissue, muscle and fatty tissue, bone marrow, urine, tears, or non-nervous system tissue.

In some embodiments of the method of treating or preventing prion-related disease in an animal, the method comprises administering to the animal a first dose comprising a peptoid reagent of the invention, or composition comprising the same, and administering to the animal a second dose comprising a peptoid reagent of the invention, or composition comprising the same, in an amount sufficient to induce an immune response in the animal. An "immune response," as used herein, is the development in the animal of a humoral and/or a cellular immunological response to a peptoid reagent such as when the peptoid reagent is present in a vaccine. Thus, the immune response generally results in the development in the animal of a secretory, cellular and/or antibody-mediated immune response. Usually, such a response includes, but is not limited to, one or more of the following effects: the production of antibodies from any of the immunological classes, such as immunoglobulins A, D, E, G or M, the proliferation of B and T lymphocytes, the provision of activation, growth and differentiation signals to immunological cells, and expansion of helper T cells, suppressor T cells, and/or cytotoxic T cells. The amount of antibodies produced will vary depending on several factors including the animal involved, the number of doses of the composition administered, the presence of an adjuvant, etc.

Some peptoid reagent compositions of the invention further comprise an adjuvant. In some such embodiments of the method of treating or preventing prion-related disease in an animal, the first dose and/or the second dose comprises at least one adjuvant. In some such embodiments, both the first and second doses comprise an adjuvant. Non-limiting examples of adjuvants useful in the doses and compositions of the invention include those in WO05/016127, herein incorporated in its entirety.

In some embodiments of the method of treating or preventing prion-related disease in an animal, the animal has been diagnosed as infected with a pathogenic prion. In some embodiments, the animal has been in close proximity to a second animal that has been diagnosed as infected with a pathogenic prion. "Close proximity" refers to the animal being in the same herd or community of animals, on the same farm, ranch or the like, or being transported, processed, etc., with the diagnosed animal. In some embodiments, the animal is a family member of a second animal that has been diagnosed as infected with a pathogenic prion. In some embodiments, the animal exhibits symptoms associated with a prion-related disease. In some embodiments, the animal is at risk for a prion-related disease. An "at risk" animal can be one that has a predisposition, genetically or otherwise, e.g., environmentally, towards developing, contracting, receiving, being exposed to or the like, a prion-related disease. An environmental predisposition includes, for example, an animal in a herd or community that is living in an area, geographically or physically, where there has been exposure to a prion-related disease. In some embodiments, the at risk animal is an offspring of an animal infected or suspected of being infected with a pathogenic prion. In some embodiments, the at risk animal has ingested biological materials derived from a second animal, where the second animal is infected with or at risk for a prion-related disease.

A composition that comprises the first dose can be the same or different than that of the second dose. In some embodiments, the composition of the second dose is the same as that of the first dose. In some embodiments, the compositions of the first and second doses are different. In some embodiments, the method further comprises administering a conventional medicament. In some embodiments, the conventional medicament comprises antibodies, oligonucleotides, organic compounds, or peptidomimetic. In some embodiments, the conventional medicament is an antigen or immunoregulatory agent such as immunoglobulins, cytokines, lymphokines, and chemokines, including but not limited to interleukin 2 (IL-2), modified IL-2 (cysl25-serl25), granulocyte macrophage colony-stimulating factor (GM-CSF), interleukin 12 (IL-12), alpha- or gamma-interferon, chemokine IP-10, and β chemokines such as RANTES, MIP1-α, and MIP1-β.

The animal in any of the treatment and prevention methods of the invention comprises humans or non-humans. For non-human animals, the animal can be wild, i.e., undomesticated, e.g., deer, elk, moose, antelope, bear, mountain goat, llama, bison, horses, mules and jackasses, big game cats such as panthers mountain lions, cougar, tigers, lions and cheetahs, and smaller mammals, e.g., rabbits, prairie dogs, raccoons, skunk, and the like, or birds; or domesticated, including, for example, domesticated pets, e.g., cats, dogs, ferrets, rabbits, rats, or mice, farm animals and livestock, e.g., cows, cattle, sheep, pigs, goats, horses, mules and jackasses, or birds, e.g., chickens, hens, ducks, geese, turkeys, and other gallinaceous birds, and laboratory animals, e.g., non-human primates such as apes, monkeys and lumers, and rodents such as mice, rats, hamsters and guinea pigs. Animals suitable for use with the invention can be of any age, including both adult and newborn. In some embodiments, the animal is a mammal. In some embodiments, the mammal is a human. In some embodiments, the mammal is a non-human. In some embodiments, the composition is administered as described hereinabove. In some embodiments, the mammal comprises a cat, dog, ferret, rabbit, rat, mouse, cow, steer, sheep, lamb, pig, goat, horse, mule, jackass, deer, elk, bear, bison, cougar, mountain lion, ape, monkey, lumer, hamster or guinea pig. In some embodiments, the mammal comprises cow, steer, deer, sheep, lamb, pig, or goat. In some embodiments, the composition is administered intramuscularly, intramucosally, intranasally, subcutaneously, intradermally, transdermally, intravaginally, intrarectally, orally or intravenously.

Isolation, Reduction & Elimination

The present invention also provides methods for isolating a pathogenic prion from a sample or reducing the amount of a pathogenic prion in a sample.

The method of isolating a pathogenic prion from a sample comprises providing a solid support comprising a peptoid reagent of the invention; contacting the solid support with the sample under conditions that allow binding of the pathogenic prion, if present in the sample, to the peptoid reagent to form a complex, and then removing unbound sample, thereby providing isolated pathogenic prion. In some embodiments, the method further comprises dissociating the pathogenic prion from the complex.

The method for reducing the amount of the pathogenic prion in a sample comprises providing a solid support comprising a peptoid reagent of the invention; then, contacting the solid support with the sample under conditions that allow binding of the pathogenic prion, if present in the sample, to the peptoid reagent of the support; and recovering unbound sample, thereby providing sample with a reduced amount of the pathogenic prion. In some embodiments, the amount of the pathogenic prion is reduced below a detectable level. In some embodiments, the amount of the pathogenic prion is reduced by about 80 to 100, about 85 to 100, about 90 to 100 or about 95 to 100%.

The invention further provides a method of preparing a blood supply that is substantially free of a pathogenic prion, where the blood supply comprises collected blood samples such as those from a blood bank or those collected from a patient before surgery, e.g., a self-sourced transfusion during surgery. The blood supply can include, for example and without limitation, whole blood, plasma, platelets or serum. In some embodiments, the method comprises detecting the presence or absence of pathogenic prion in a plurality of samples according to a detection method of the invention, and combining the samples in which the pathogenic prion is not detected, thereby providing the blood supply that is substantially free of the pathogenic prion. In some embodiments, the detection method of the invention comprises allowing a peptoid reagent to bind to the pathogenic prion, if present, to form a complex, and detecting the presence of the pathogenic prion in the sample by its binding to the peptoid reagent. In some embodiments, the binding of the pathogenic prion to the peptoid reagent can be detected by detecting the formation of the complex, the formation of the complex being indicative of the presence of the pathogenic prion. In some embodiments, the complex comprising the peptoid reagent and the pathogenic prion protein is separated from the rest of the sample (that is, the unbound sample) prior to detection. In some embodiments, the formation of the complex can be detected by detecting the pathogenic prion in the complex or by dissociating the complex (after separation from the unbound sample) and detecting the dissociated pathogenic prion.

The invention also provides a method of preparing a food supply such as a meat supply (e.g., muscle and fatty tissue (i.e., flesh) of cattle, sheep or pig, e.g., beef, lamb, mutton or pork used for human or animal consumption) that is substantially free of pathogenic prions. In some embodiments, the method comprises detecting the presence or absence of pathogenic prion in a plurality of samples according to a detection method of the invention, and combining the samples in which the pathogenic prion is not detected, thereby providing the food supply that is substantially free of the pathogenic prion. In some embodiments, the food supply is collected from a live or once-live organism that will enter the food supply or from food intended to enter the food supply. In some embodiments, the detection method of the invention comprises allowing a peptoid reagent to bind to the pathogenic prion, if present, to form a complex, and detecting the presence of the pathogenic prion in the sample by its binding to the peptoid reagent. In some embodiments, the binding of the pathogenic prion to the peptoid reagent can be detected by detecting the formation of the complex, the formation of the complex being indicative of the presence of the pathogenic prion. In some embodiments, the complex comprising the peptoid reagent and the pathogenic prion protein is separated from the rest of the sample (that is, the unbound sample) prior to detection. In some embodiments, the formation of the complex can be detected by detecting the pathogenic prion in the complex or by dissociating the complex (after separation from the unbound sample) and detecting the dissociated pathogenic prion.

Designing

Further provided by the invention is a method of designing a peptoid reagent of the invention. As a starting point, the peptoid reagent can be designed based on the sequences of certain peptide fragments of a prion protein (eg, peptide fragments having SEQ ID NOs 12-228) by making replacements of amino acid residues in the sequence of the peptide fragment with N-substituted glycines, synthesis of the modified peptide using methods described in U.S. Pat. Nos. 5,811,387, 5,831,005, 5,877,278, 5,977,301 and 6,033,631, as well as Simon et al. (1992) *Proc. Natl. Acad. Sci. USA* 89: 9367, which publications are incorporated herein by reference in their entirety, testing of the modified peptide for binding to pathogenic prion proteins by the methods described herein. Additional replacements can be made according to the replacement scheme below until a suitable peptoid reagent is achieved.

Further, the designing of the peptoid reagent can comprise aspects of the *Solid-phase Submonomer Synthesis Protocol for Peptoids* described in Example 5, below.

In some embodiments, the method of making a peptoid reagent of the invention comprises:
  a) providing a peptide fragment of a prion protein; replacing a first amino acid of a peptide fragment with an N-substituted glycine by the following replacement scheme:
    i) Ala, Gly, Ile, Leu, Pro, and Val are replaced by N-(alkyl)glycine, N-(aralkyl)glycine, or N-(heteroarylalkyl)glycine;
    ii) Asp, Asn, Cys, Gln, Glu, Met, Ser, and Thr are replaced by N-(hydroxyalkyl)glycine, N-(alkoxy)glycine, N-(aminoalkyl)glycine, or N-(guanidinoalkyl)glycine;
    iii) Phe, Trp, and Tyr are replaced by N-(aralkyl)glycine, N-(heteroarylalkyl)glycine, N-(hydroxyaralkyl)glycine, or N-(alkoxyaralkyl)glycine; and
    iv) Arg, His, and Lys are replaced by N-(aminoalkyl)glycine or N-(guanidinoalkyl)glycine;
  b) replacing a second amino acid of the peptide fragment with an N-substituted glycine according to Step a);
  c) replacing a third amino acid of the peptide fragment with an N-substituted glycine according to Step a); and
  d) optionally, repeating step c) 1-27 times, thereby, providing a designed peptoid reagent comprising 3 to 30 N-substituted glycines; and, synthesizing the designed peptoid reagent.

In some embodiments of the above method, the peptide fragment comprises a peptide having a sequence selected from the group consisting of SEQ ID NOs. 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, and 228.

In some embodiments of the above method, the peptide fragment comprises a peptide having a sequence selected from the group consisting of SEQ ID NOs. 66, 67, 68, 72, 81, 96, 97, 98, 107, 108, 109, 14, 35, 36, 37, 40, 50, 51, 77, 89, 100, 101, 110, 56, 57, 65, 82, 84, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 278, 279, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, and 228.

In some embodiments of the above method, the peptide fragment comprises a peptide having a sequence selected from the group consisting of SEQ ID NOs. 12, 14, 50, 51, 52, 68, 72, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219.

In some embodiments of the above method, the peptide fragment comprises a peptide having a sequence selected from the group consisting of SEQ ID NOs. 14, 50, 51, 52, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219.

In some embodiments of the above method, the peptide fragment comprises a peptide having a sequence selected from the group consisting of SEQ ID NOs. 12, 68, 72, 115, 116, 117, 118, 119, 120, 121, 122, 123, 124, 125, 126, 127, 128, 129, 130, 131, 132, 133, 134, 135, 135, 137, 138, 139, 140, 141, 142, 143, 144, 145, 146, 147, 148, 149, 150, 151, 152, 153, 154, 155, 156, 157, 158, 159, and 160.

In some embodiments of the designing method for the peptoid reagent, the peptide fragment comprises a peptide having a sequence selected from the group consisting of SEQ ID NOs. 12, 14, 50, 51, 52, 67, 68, 72 and 109. In some embodiments, the peptide fragment comprises a peptide having a sequence of SEQ ID NO: 14 or 68.

In some embodiments, the method further comprises adding to the peptoid reagent a conjugate moiety selected from an effector molecule, a substrate, or a label, each optionally attached to the peptoid reagent through a linker moiety. In some embodiments, the conjugate moiety comprises biotin. In some embodiments, the conjugate moiety comprises a mercapto group.

Other Uses

The invention also provides a solid support comprising at least one peptoid reagent of the invention. The solid support can be as previously described hereinabove. The invention further provides a kit for detecting the presence of a pathogenic prion in a sample. In some embodiments, the kit comprises a peptoid reagent of the invention. In some embodiments, the kit comprises a solid support comprising a peptoid reagent of the invention. In some embodiments, the kit comprises a solid support comprising a peptoid reagent of the invention, and a reagent. The reagent can be, for example and without limitation, a detection reagent such as a detectably labeled-antibody, chromophore, chromogen, a prion-binding reagent such as anti-prion antibodies, motif-grafted hybrid polypeptides, cationic or anionic polymers, propagation catalysts and plasminogen or a buffer. In some embodiments, the kit comprises two or more peptoid reagents of the invention. In some kit embodiments, positive and/or negative controls are optionally included.

In order that the invention disclosed herein can be more efficiently understood, examples are provided below. It should be understood that these examples are for illustrative purposes only and are not to be construed as limiting the invention in any manner.

EXAMPLES

Example 1

Peptoid Region Sequences

Table 1 lists example peptoid regions (amino to carboxy directed) suitable for preparing peptoid reagents of the present invention. Table 2 provides a key to the abbreviations used in Table 1. Table 3 provides the relevant structures of each of the sequences. Peptoid reagents containing the sequences of Table 1 were tested for preferential binding to PrP$^{Sc}$, according to the assays described herein. Preparations of the specific reagents are described hereinbelow.

TABLE 1

Representative peptoid regions for peptoid reagents of the invention.

| Peptoid Region Sequence | SEQ ID NO: |
|---|---|
| Nab-Nab-Nab-Nab-Nab | 229 |
| Nab-Nab-Ngb-Nspe-Nab-Nspe | 230 |
| Nae-Nmpe-Nmpe-Nae-Nmpe-Nmpe-Nae-Nmpe-Nmpe | 231 |
| Nme-Ntrp-Nme-Nab-Nspe-Nhye-Nab-Nspe-Nhye-Nme | 232 |
| Nspe-Nab-Nspe-Nab-Nspe-Nspe-Nab-Nspe-Nab-Nspe-Nspe | 233 |
| Nbn-Nab-Nbn-Nab-Nbn-Nbn-Nab-Nbn-Nab-Nbn-Nbn | 234 |
| Nme-Nab-Nme-Nab-Nnm-Nme-Nab-Nnm-Nab-Nme-Nme | 235 |
| Nme-Nab-Nme-Nab-Nme-Nme-Nab-Nme-Nab-Nme-Nme | 236 |
| Nab-Nab-Nab-Nspe-Nab-Nspe | 237 |
| Nab-Nspe-Nab-Nab-Nspe-Nab | 238 |
| Nab-Nab-Nab-Nspe-Nab-Nspe | 239 |
| Nab-Nab-Nab-Nbn-Nab-Nbn | 240 |
| Nme-Nbn-Nme-Nbn-Nme-Nbn | 241 |

TABLE 2

Abbreviations key to Table 1.

| Peptoid Residue Abbreviation | Amino Acid Substitute |
|---|---|
| Ntyr | N-(2-(4-hydroxyphenyl)ethyl)glycine |
| Nhph | N-(4-hydroxyphenyl)glycine |
| Nspe | (S)-N-(1-phenylethyl)glycine |
| Nme | N-(2-methoxyethyl)glycine |
| Ncpm | N-(cyclopropylmethyl)glycine |
| Ntrp | N-(2-3'-indolylethyl)glycine |
| Nab | N-(4-aminobutyl)glycine |
| Nmpe | N-(2-(4-methoxyphenyl)ethyl)glycine |
| Ndmb | N-(3,5-dimethoxybenzyl)glycine |
| Nbn | N-benzylglycine |
| Nhye | N-(2-hydroxyethyl)glycine |
| Nip | N-isopropylglycine |
| Nnm | N-((8'-naphthyl)methyl)glycine |
| Ngb | N-(4-guanidinobutyl)glycine |
| Nae | N-(4-aminoethyl)glycine |

TABLE 3

Relevant structures of peptoid regions of Table 1.

| SEQ ID NO: | Structure |
|---|---|
| 229 | 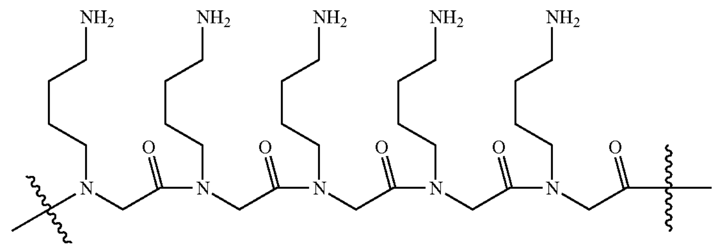 |
| 230 | 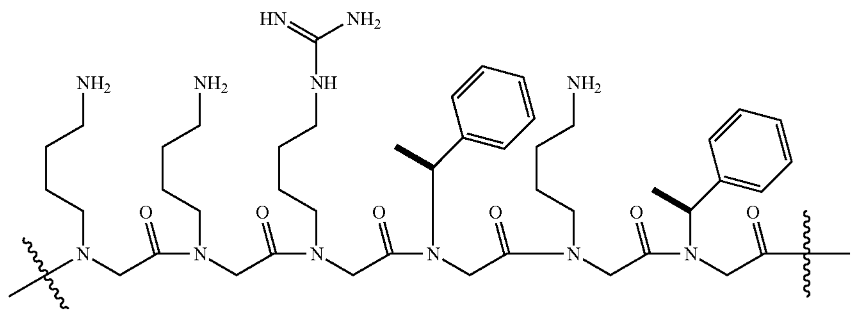 |
| 231 | 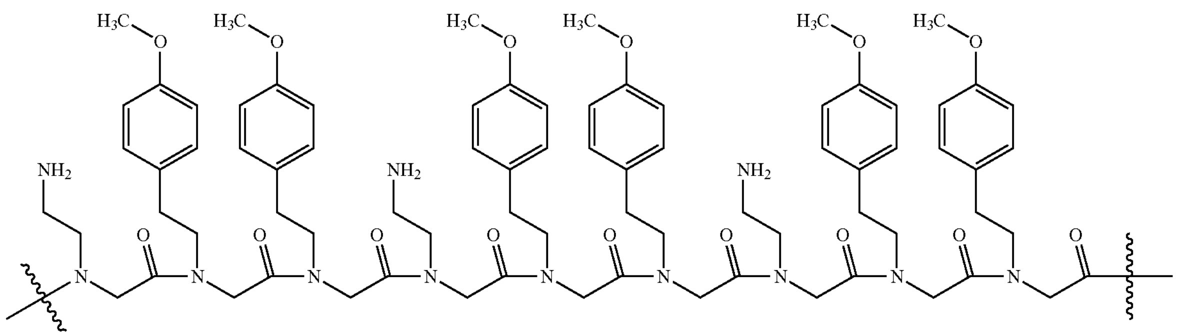 |

TABLE 3-continued
Relevant structures of peptoid regions of Table 1.
| SEQ ID NO: | Structure |
|---|---|
| 232 | 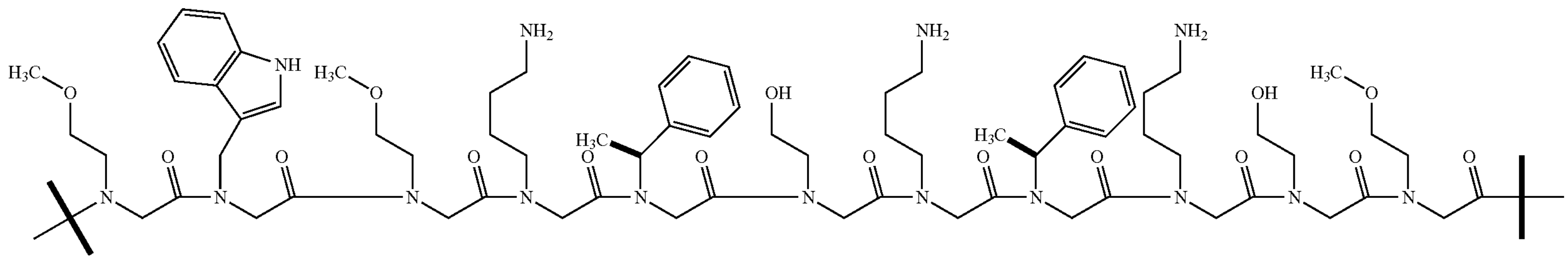 |
| 233 | 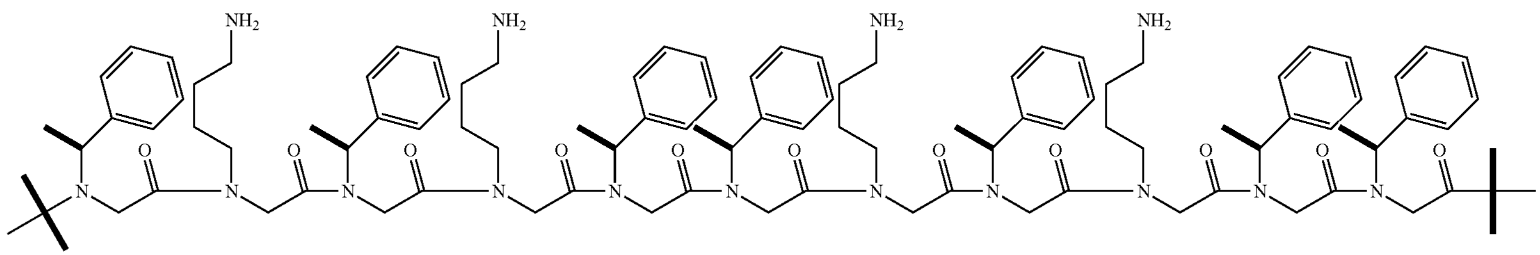 |
| 234 | 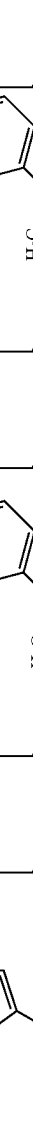 |

TABLE 3-continued

Relevant structures of peptoid regions of Table 1.

| SEQ ID NO: | Structure |
|---|---|
| 235 | 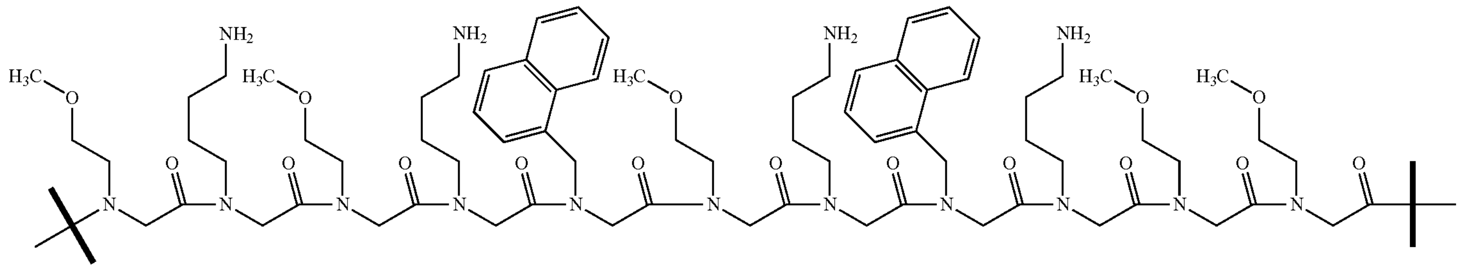 |
| 236 | 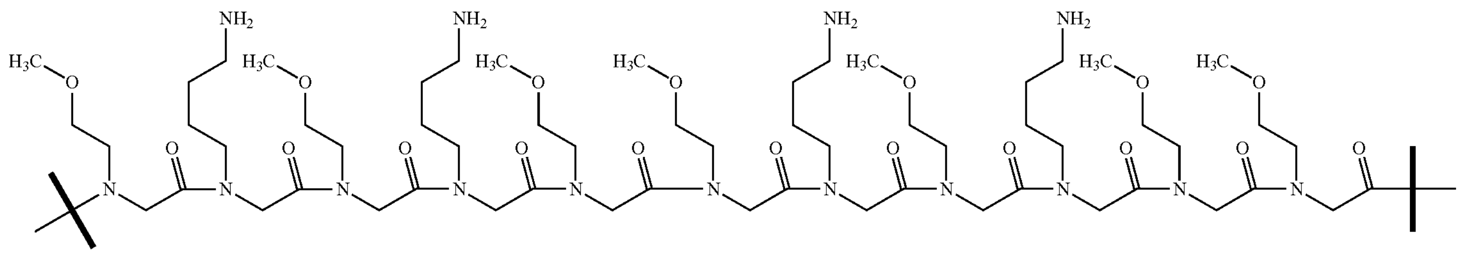 |
| 237 | 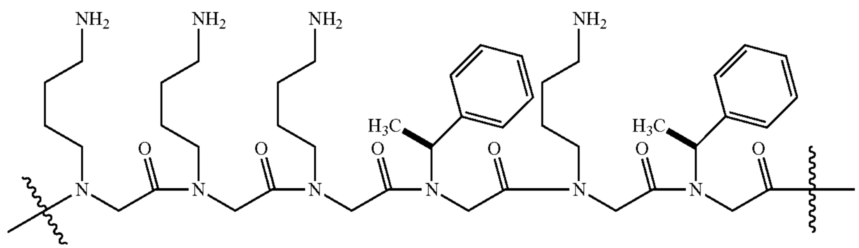 |

TABLE 3-continued

Relevant structures of peptoid regions of Table 1.

| SEQ ID NO: | Structure |
|---|---|
| 238 | 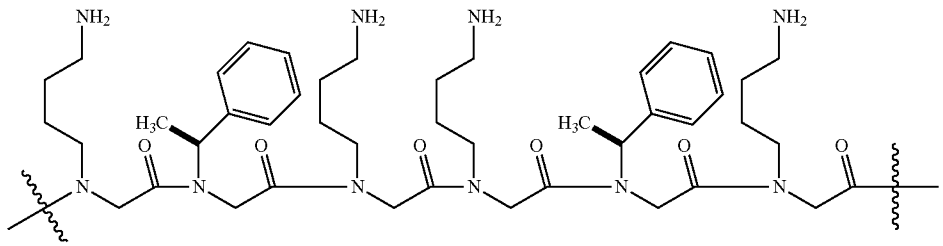 |
| 239 | 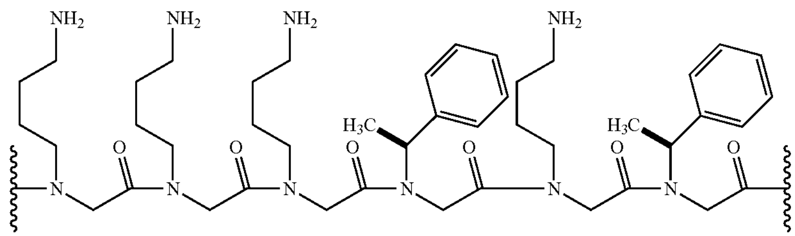 |
| 240 | 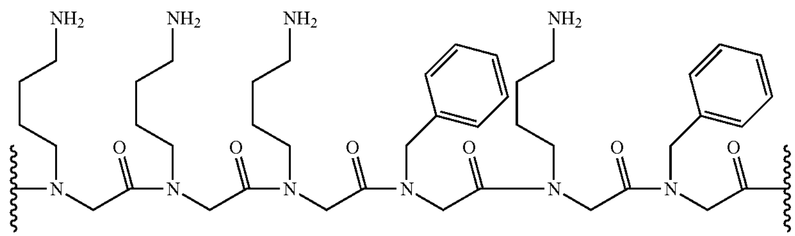 |
| 241 | 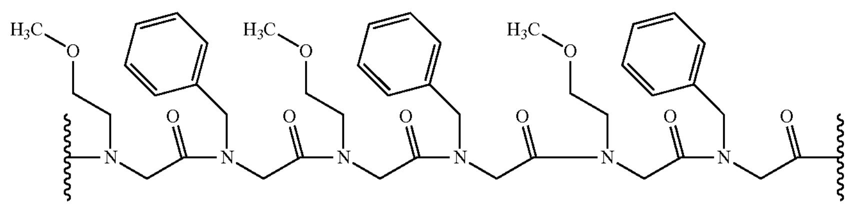 |

Example 2

Peptoid Reagents

The following peptoid reagents were prepared using synthetic methods for preparation of peptoid molecules containing N-substituted glycine residues such as the procedures disclosed in U.S. Pat. Nos. 5,811,387, 5,831,005, 5,877,278, 5,977,301 and 6,033,631, as well as Simon et al. (1992) *Proc. Natl. Acad. Sci. USA* 89: 9367, each of which is incorporated herein by reference in its entirety, and using the protocol described in Example 5. Each of the below reagents was tested for binding affinity for a prion protein according to the assays described herein.

Peptoid Reagent I

The below peptoid reagent comprises SEQ ID NO: 229.

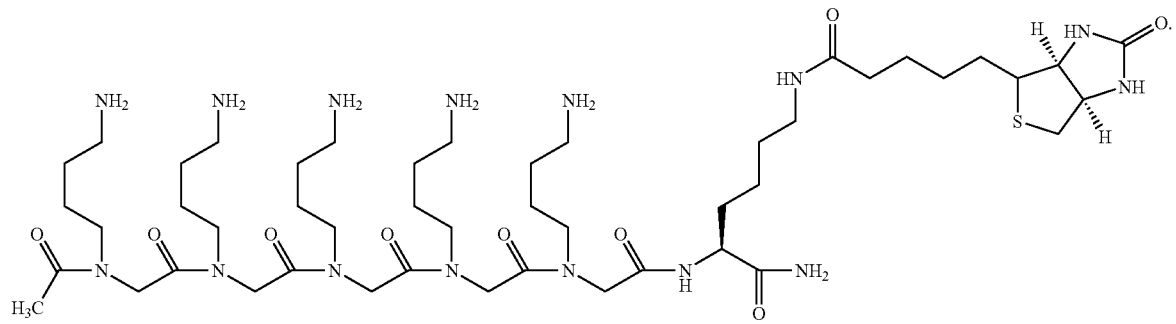

Calculated Mass: 1054.42; Observed Mass: 1054.2. All observed mass measurements were measured on a Waters (Milford, Mass.) Micromass ZQ LC/MS System.

Peptoid Reagent II

The below peptoid reagent comprises SEQ ID NO: 230.

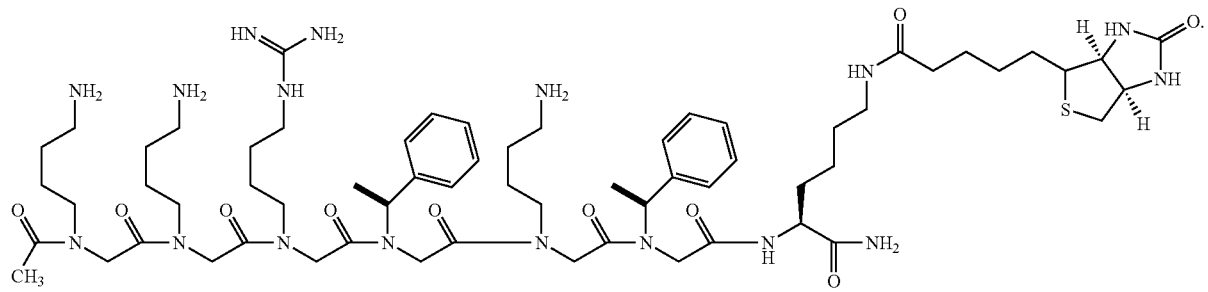

Calculated Mass: 1290.70; Observed Mass: 1290.8.

Peptoid Reagent III
The below peptoid reagent comprises SEQ ID NO: 231.
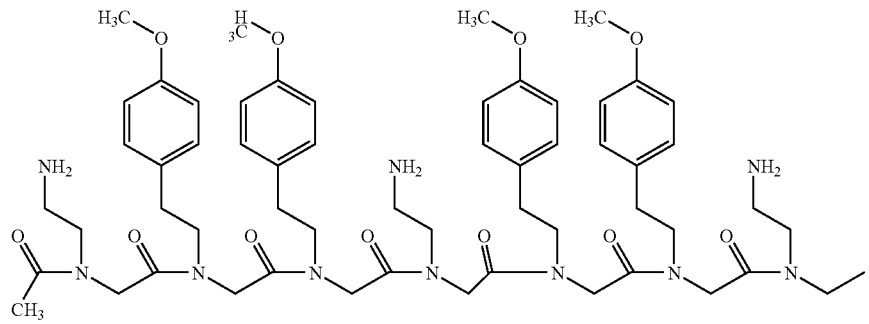
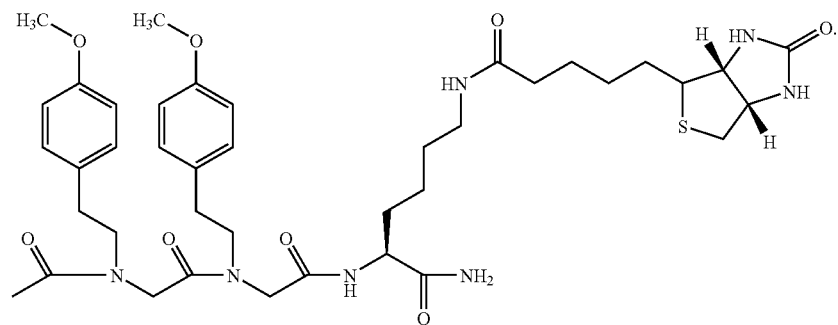
Calculated Mass: 1861.30; Observed Mass: 1861.6.
Peptoid Reagent IV
The below peptoid reagent comprises SEQ ID NO: 232.
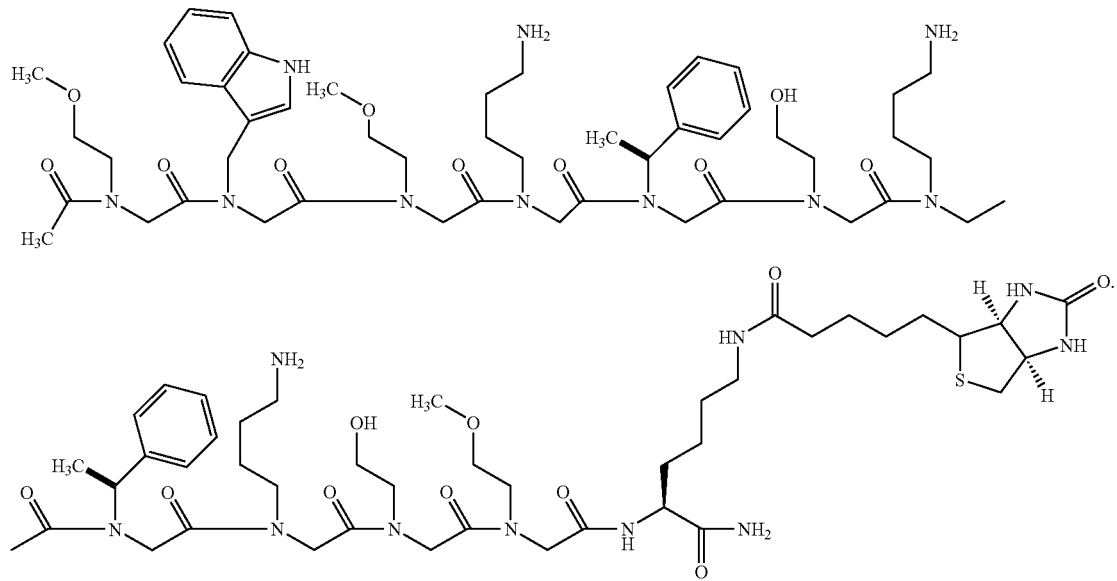

Peptoid Reagent V
　The below peptoid reagent comprises SEQ ID NO: 233.
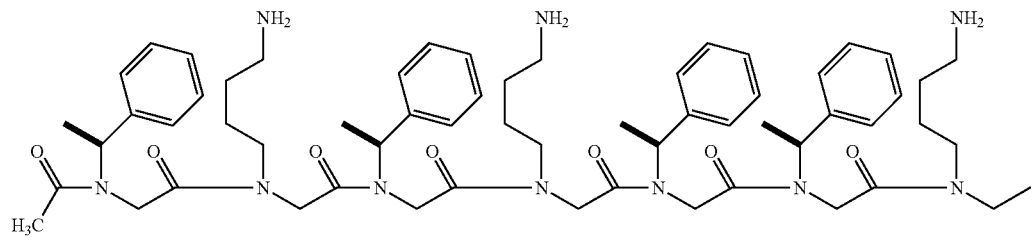
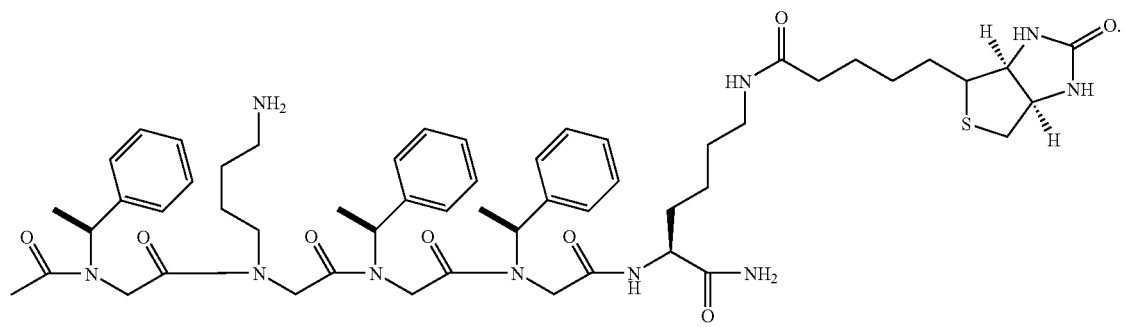
Peptoid Reagent VI
　The below peptoid reagent comprises SEQ ID NO: 234.
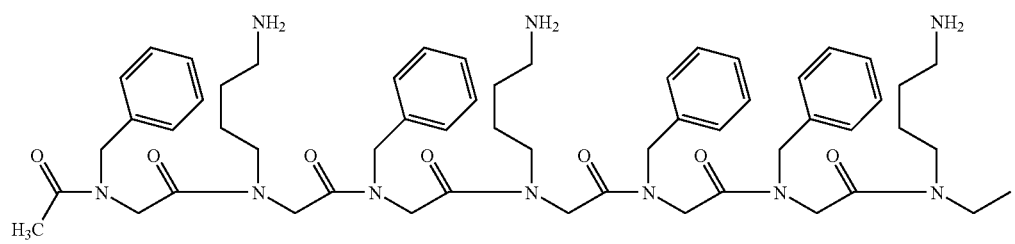
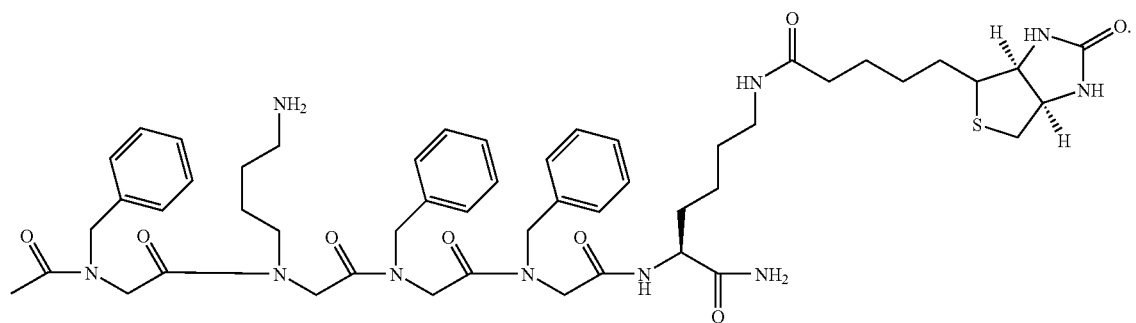

Calculated Mass: 1956.49; Observed Mass: 1956.2.
Peptoid Reagent VII
The below peptoid reagent comprises SEQ ID NO: 235.
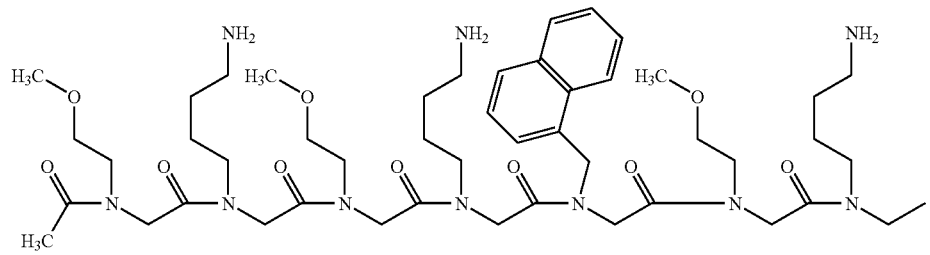
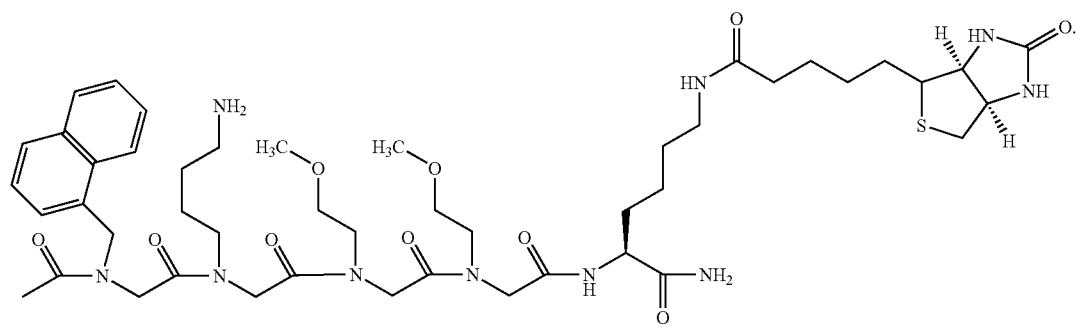
Calculated Mass: 1896.39; Observed Mass: 1896.4.
Peptoid Reagent VIII
The below peptoid reagent comprises SEQ ID NO: 236.
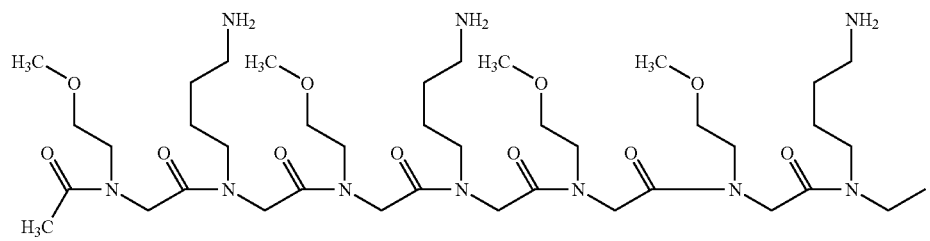
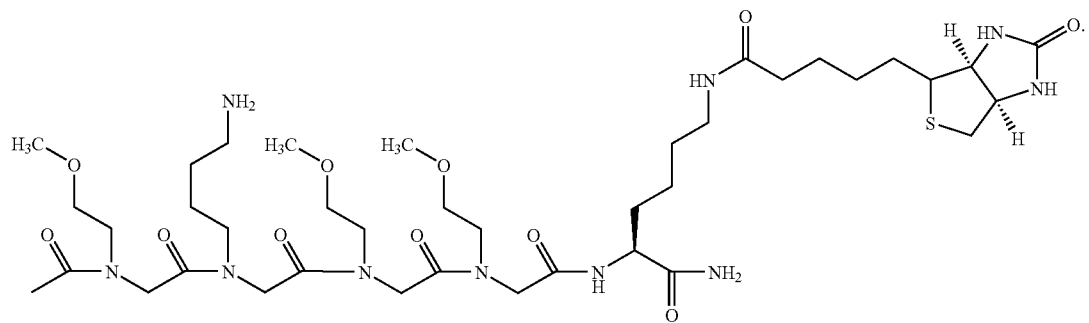
Calculated Mass: 1732.18; Observed Mass: 1732.4.

Peptoid Reagent IX
The below peptoid reagent comprises SEQ ID NO: 237.
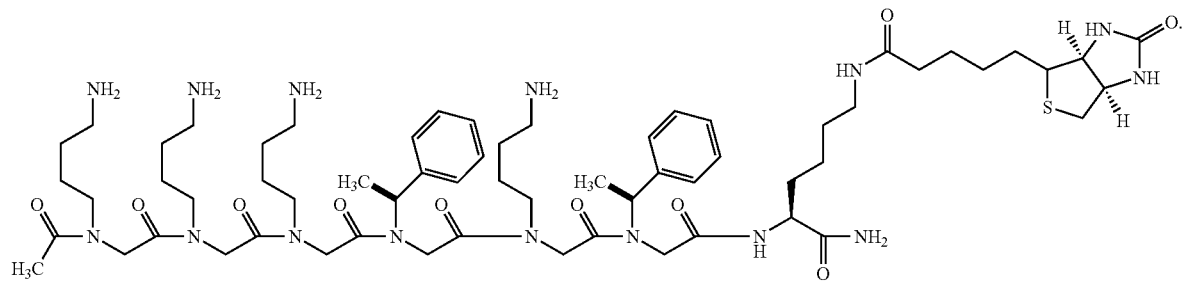
Calculated Mass: 1248.65; Observed Mass: 1248.4.
Peptoid Reagent X
The below peptoid reagent comprises SEQ ID NO: 238.
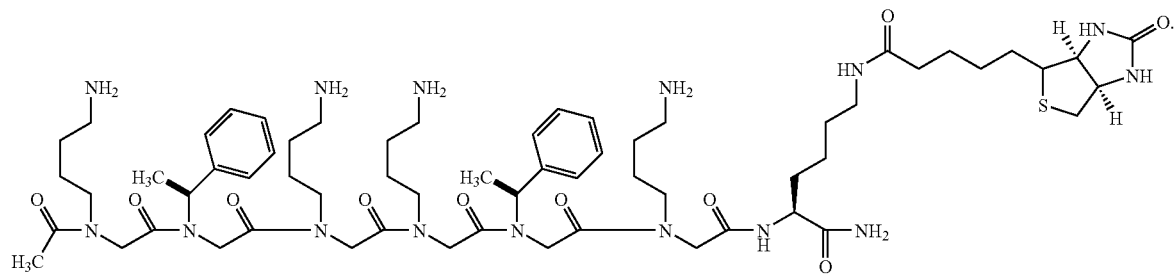
Calculated Mass: 1248.65; Observed Mass: 1248.4.
Peptoid Reagent XIa and XIb
The below peptoid reagents, XIa and XIb, comprise SEQ ID NO: 239.
XIa
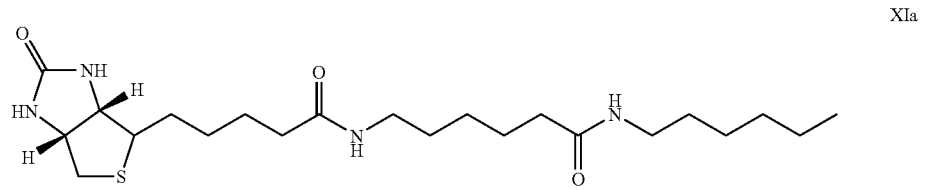
XIb
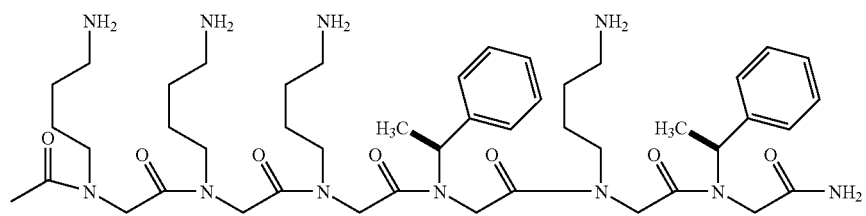

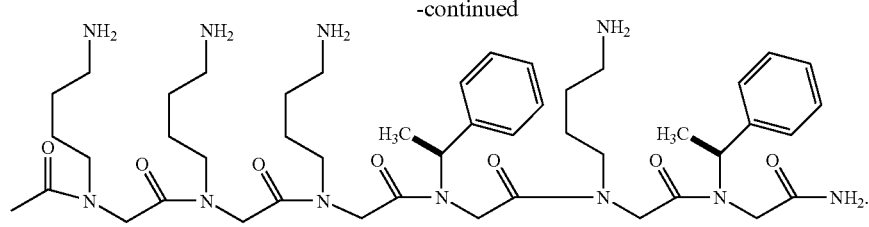
XIa: Calculated Mass: 1304.76; Observed Mass: 1304.6.
XIb: Calculated Mass: 1166.59; Observed Mass: 1166.2.
Peptoid Reagent XIIa and XIIb
The below peptoid reagents of formula XIIa and XIIb comprise SEQ ID NO: 240.
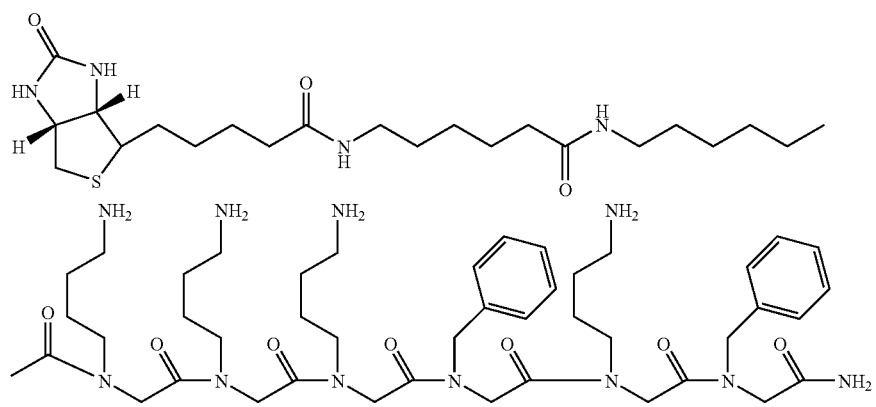
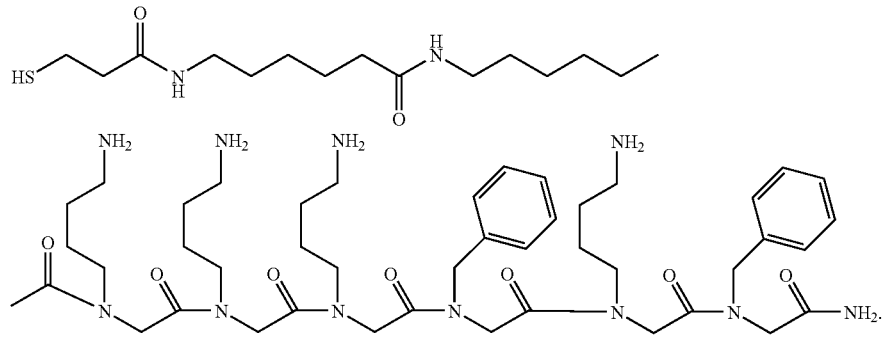
XIIa: Calculated Mass: 1276.71; Observed Mass: 1276.6.
Peptoid Reagent XIII
The below peptoid reagent comprises SEQ ID NO: 241.
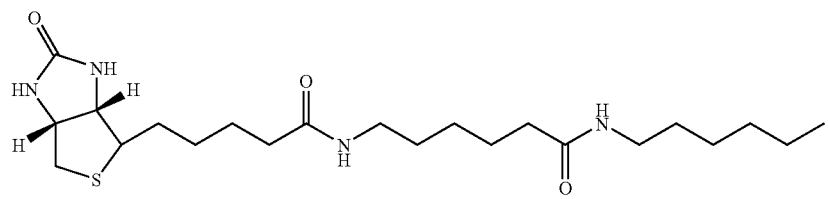

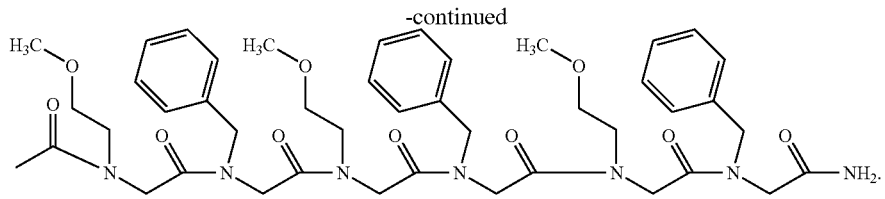

Calculated Mass: 1256.58; Observed Mass: 1256.6.

Example 3

Binding Assays

Pull-Down Assay

Peptoid reagents of Example 2 were tested for their ability to specifically bind to pathogenic prion proteins using a magnetic bead pull down assay. For this assay, peptoid reagents were attached to magnetic beads in one of two ways: 1) the peptoid reagents were labeled with biotin, which allowed attachment to streptavidin coated magnetic beads or 2) peptoids were covalently linked to magnetic beads through a thiol propionic acid. The mode of attachment of the peptoid reagent to the beads had little effect on the binding activity of the peptoid reagent; however, when the peptoid reagents were covalently attached to the beads, less background interference from plasma samples used as diluent was observed. The magnetic beads were obtained from Dynal (Brown Deer, Wis.). Typically, ten microliters (10 μl) of Streptavidin M-280 Dynabeads® (cat # 112.05) were used for single pull-down reaction using biotinylated peptoid reagent.

Human brain homogenates (10% w/v in 0.25 M Sucrose) from deceased CJD patients and from healthy (i.e., non-CJD) deceased individual were obtained from the National Institute for Biological Standards and Controls (NIBSC), Blanche Lane South Mimms, Pottersbar, United Kingdom. For most of the experiments described herein, samples from 3 CJD patients (one nvCJD patient and two sCJD patients) were combined and assays were carried out on the combined brain homogenate samples. Aliquots of 200 μl were diluted 1:1, vol:vol, in TBS buffer (50 mM Tris-HCl pH 7.5 and 37.5 mM NaCl) containing 1% Triton X100, and 1% Tween-20 and the samples sonicated for several repeats of several seconds each. Brain homogenate aliquots were kept in −70° C.

To evaluate peptoid reagent binding to PrP$^{Sc}$, CJD brain homogenates were spiked into human plasma of a healthy individual. In general two negative control samples were used: 1) normal human plasma and 2) normal human plasma spiked with normal (non-CJD) human brain homogenate. The standard assay concentration of human plasma varied from 0 up to 80% of the total sample volume.

In a typical protocol, for one pull-down test (final 100 μl in one well of microtiter 96-well plate), 10 μl of Streptavidin M-280 Dynabeads® (cat # 112.05) is used. The appropriate amount of beads are washed once before use with TBS containing 1% Tween-20 and 1% Triton X-100 (TBSTT). Beads pellets are resuspended into 10 times of the original volume, i.e., 100 μl with TBSTT. Thereafter, 0.1 μl of biotinylated peptoid reagent stock (10 mM in H$_2$O) is added to the beads solution, mix in RT, 750 rpm (Eppendorf, Thermomixer R) for 1 hr or 30 min 750 rpm at 37° C. Supernatants containing unbound peptoids are discarded and beads are washed three times using TBS and Tween-20 0.05% (TBST) using a magnet apparatus that holds the beads to the bottom of the tube. At this stage, peptoid reagent-coated streptavidin magnetic beads are obtained. Next, peptoid-coated magnetic beads (representing the original μl starting volume) are mixed with various concentrations of CJD 10% brain homogenate in the presence of plasma (final concentration of 0-80%), 1×TBS, 1% Triton X100, and 1% Tween-20 at a final volume of 100 μl. A typical reaction volume is 100 μl in well of 96-well plate. The plate is shaken at 750 rpm (Eppendorf, Thermomixer R) for 1 hr at 37° C. Beads are washed to remove non-bound protein, four times with TBS solution containing 0.05% Tween-20, using plate washer ELx405 Magna (Bio-Tek Instruments, Inc., Winooski, Vt.). This microtiter plate washer is specifically designed for applications using magnetic bead technology. A second carrier positions the magnet plate close to the microplate bottom, securing magnetic beads during the critical aspiration cycles.

ELISA

Following the final wash of the Pull-Down assay, PrP$^{Sc}$ is eluted from the beads, denatured and detected with monoclonal (mAb) anti-prion antibodies in ELISA (enzyme-linked immunosorbent assay) format. In one assay format (an indirect ELISA), the detection of anti-prion mAb, which is proportional to the amount bound to PrP$^{Sc}$, is achieved with secondary polyclonal antibody that recognize the primary monoclonal. The secondary antibody is conjugated to the enzyme Alkaline Phosphatase. When incubated with chemiluminescence substrate, the enzyme breaks a chemical compound resulting in emission of light that is measured by a standard microplate chemiluminescence reader. The measured units are defined as relative light units (RLU). In the second format (a direct ELISA), detection is done using monoclonal (mAb) anti-prion antibodies that are conjugated to Alkaline Phosphatase, thus no secondary antibody is needed. The same chemiluminescence substrate (Lumi-Phos Plus from Lumingen, Inc.) is used for both formats. Sandwich ELISA formats can also be used, as described herein. The ELISA can be carried out in any of a number of formats, e.g, on plates, on beads, on magnetic particles. The denatured, eluted prion can be passively coated onto the solid support or can be bound in an antibody-antigen sandwich type arrangement, the anti-prion antibody being coated on the solid support.

Results

Results of ELISA binding assays are summarized below.

The majority of representative peptoid reagents of the invention tested have similar binding efficiency as that of the peptide of SEQ ID NO: 68. In previous studies, the peptide of SEQ ID NO: 68 had good binding efficiency for prion proteins (See e.g., U.S. patent application Ser. No. 11/056,950, filed Feb. 11, 2005) and thus, was used as a benchmark to measure the binding efficiencies of the peptoid reagents of the invention. The data in Table 4 show the signals obtained in pull-down/ELISA assays using various peptoid reagents compared to a peptide reagent (SEQ ID NO:68, described in co-owned applications U.S. Ser. No. 10/917,646, filed Aug.

13, 2004, U.S. Ser. No. 11/056,950, filed Feb. 11, 2005, and International Application PCT/US2004/026363, filed Aug. 13, 2004.) The signals from a 1 ul sample of a 10% CJD brain homogenate or from a 1 ul sample of a 10% normal brain homogenate, both in 70% plasma, are shown. The far right column reports the experimental mean of the peptoid reagent assays as a % of the experimental mean of the peptide SEQ ID NO:68 assay.

TABLE 4

Percent binding of representative peptoid reagents in 70% human plasma compared to peptide of SEQ ID NO: 68.

| Peptide or Peptoid by SEQ ID NO. | Control Mean (1 ul 10% Normal BH) | Exp. Mean (1 ul 10% CJD BH) | Exp. SD* | Exp. Mean (as % of 68) |
|---|---|---|---|---|
| Streptavidin bead (no peptide control) | 16.4 | 21.1 | 3.7 | 5.0 |
| 68 | 19.2 | 852.7 | 72.0 | 100.0 |
| 237 | 20.1 | 1039.4 | 41.0 | 121.9 |
| 239 | 16.9 | 1024.2 | 41.7 | 120.1 |
| 240 (XIIa) | 21.4 | 1044.4 | 60.4 | 122.5 |
| 241 | 15.4 | 28.0 | 1.2 | 3.3 |

*SD = standard deviation.

TABLE 5

Percent binding of representative peptoid reagents in 70% human plasma compared to peptide of SEQ ID NO: 68.

| Peptide or Peptoid by SEQ ID NO. | Control Mean (1 ul 10% Normal BH) | Exp. Mean (1 ul 10% CJD BH) | Exp. SD* | Exp. Mean (as % of 68) |
|---|---|---|---|---|
| Streptavidin bead (no peptide control) | | 11.2 | 1.2 | 2.7 |
| 68 | | 418.4 | 30.1 | 100.1 |
| 230 (II) | 7.02 | 463.5 | 24.8 | 110.8 |
| 237 (IX) | 9.47 | 528.8 | 24.9 | 126.5 |
| 238 (X) | 7.28 | 478.7 | 44.5 | 114.5 |

*SD = standard deviation.

TABLE 6

Percent binding of representative peptoid reagents in 20% human plasma compared to peptide of SEQ ID NO: 68.

| Peptide or Peptoid by SEQ ID NO. | Mean | SD* | Mean (% of 68) |
|---|---|---|---|
| Streptavidin bead (no peptide control) | 2.38 | 0.82 | 2.79 |
| 68 | 84.98 | 13.55 | 100.00 |
| 14 | 4.74 | 1.23 | 5.58 |
| 229 | 88.64 | 7.19 | 104.31 |
| 230 | 106.10 | 5.58 | 124.85 |
| 231 | 1.83 | 0.43 | 2.15 |
| 234 | 8.32 | 1.33 | 9.79 |
| 235 | 8.85 | 1.93 | 10.42 |
| 236 | 1.47 | 0.30 | 1.73 |

*SD = standard deviation.

As shown in Tables 4 and 5, in 70% plasma, many of the representative peptoid reagents tested have a greater binding affinity than that of the benchmark peptide, SEQ ID NO. 68, and often approximately 10 to 25% greater. Tables 4 and 5 also show the specificity of the peptoid reagents for the pathogenic form of the prion protein (only the nonpathogenic form of the prion protein is expected to be present in the normal brain homogenates). Table 6 shows the results of pull-down/ELISA assays with peptoid reagents in CJD brain homogenates diluted into 20% human plasma.

TABLE 7

Percent binding of a representative peptoid reagent bound directly to magnetic beads in 70% human plasma compared to peptide of SEQ ID NO: 68.

| Peptide or Peptoid Covalently bound to Magnetic Beads by SEQ ID NO. | Mean | SD* | Mean (% of 68) |
|---|---|---|---|
| 68 | 137.9 | 21.29 | 100.0 |
| 240 (XIIb) | 174.3 | 10.51 | 126.4 |

*SD = standard deviation.

Peptoid reagent comprising SEQ ID NO:240 (XIIb) was covalently bound to magnetic beads, peptides comprising SEQ ID NO:68 was also covalently bound to magnetic beads. The covalently bound reagents were used in a pull-down/ELISA reaction as described above for the biotinylated peptoid reagents and peptides bound to the SA-beads. Covalent binding of the reagents to the beads did not significantly affect the ability of the beads to preferentially interact with the pathogenic prions.

Specificity of Reagents for Pathogenic Form

As shown in Tables 4 and 5 above, the peptoid reagents can pull down the $PrP^{SC}$ that is present in human brain homogenates from CJD patients but do not pull down any of the $PrP^C$ present in human plasma or in the control normal human brain homogenate. Additional experiments comparing the binding of the peptoid reagents to CJD brain homogenates and normal (i.e., non-CJD) brain homogenates are shown below.

TABLE 8

Binding of peptoid reagents to 2 microliters of 10% normal or CJD brain homogenate in 70% human plasma.

| | Human Brain Homogenate Spiked Plasma Binding | | | |
|---|---|---|---|---|
| Peptide or Peptoid by SEQ ID NO. | Normal Mean | Normal SD | CJD Mean | CJD SD |
| 229(I) | 3.31 | 0.3 | 124.47 | 20.21 |

TABLE 9

Binding of peptoid reagents to 0.1 microliter of 10% CJD brain homogenate or 1 microliter of 10% normal human brain homogenate in 70% human plasma.

| | Human Brain Homogenate Spiked Plasma Binding | | | |
|---|---|---|---|---|
| Peptide or Peptoid by SEQ ID NO. | Normal Mean | Normal SD | CJD Mean | CJD SD |
| 239(XIa) | 16.91 | 1.68 | 147.49 | 32.33 |
| 239(XIb) | 33.28 | 0.65 | 255.51 | 2.91 |
| 240(XIIa) | 21.42 | 0.59 | 187.89 | 12.74 |
| 241(XIII) | 15.43 | 2.6 | 17.36 | 2.57 |

The experiments in Table 10 was carried out on a sample of human vCJD brain homogenate rather than a mixture of vCJD and sCJD BH.

TABLE 10

Binding of Peptoid Reagent 240(XIIb) covalently attached to magnetic beads to normal or vCJD brain homogenate in 70% human plasma.

| Binding of peptoid reagent SEQ ID NO. 240(XIIb) to | Mean | SD |
|---|---|---|
| 7.5 nL human vCJD 10% brain homogenate | 121.1 | 6.7 |
| 2.5 nL human vCJD 10% brain homogenate | 57.3 | 8.2 |
| 0.833 nL human vCJD 10% brain homogenate | 49.2 | 3.4 |
| 15 nL 10% normal human brain homogenate | 13.2 | 2.9 |

TABLE 11

Binding of Peptoid Reagent 240(XIIb) covalently attached to magnetic beads.

| Binding of SEQ ID NO. 240(XIIb) to | Mean | SD |
|---|---|---|
| TBS Buffer | 278.5 | 43.9 |
| TBSTT Buffer | 264.3 | 24.9 |
| TBSTT with 70% Human Plasma | 269.5 | 32.9 |
| TBSTT with 70% Human Plasma containing 20 nL 10% normal human brain homogenate | 306.4 | 41.3 |
| TBSTT with 70% Human Plasma containing 20 nL 10% human CJD brain homogenate | 1390.8 | 76.0 |

In the course of these experiments, it was observed that certain human plasma samples apparently contained some material that interfered with the binding reaction and resulted in lower signals when those plasmas were used as the diluents. Comparison experiments were carried out with peptoid reagents that were covalently attached to the magnetic beads and the same peptoid reagents attached to the magnetic beads via biotin-streptavidin binding (Table 12 vs. Table 13). The covalently coupled peptoid reagents were much less sensitive to variations in the plasma samples used as diluent.

TABLE 12

Pull-down assays using representative biotinylated peptoid reagent bound to streptavidin magnetic beads in various human plasmas.

| Peptoid SEQ ID NO. 240 (XIIa) with Human Plasma | Mean | SD* | Mean (% of Control) |
|---|---|---|---|
| Control Human Plasma | 1109.67 | 80.93 | 100.0 |
| Human Plasma lot KC011886 | 441.40 | 38.74 | 39.78 |
| Human Plasma lot KC011892 | 406.60 | 64.93 | 36.64 |
| Human Plasma lot KC28719 | 720.50 | 102.03 | 64.93 |
| Human Plasma lot KC032907 | 458.50 | 151.48 | 41.32 |

*SD = standard deviation.

TABLE 13

Pull-down assays using representative peptoid reagent bound directly to magnetic beads in various human plasmas.

| Peptoid SEQ ID NO. 240 (XIIb) with Human Plasma | Mean | SD* | Mean (% of Control) |
|---|---|---|---|
| Control Human Plasma | 154.99 | 52.13 | 100.0 |
| Human Plasma lot KC011886 | 205.80 | 12.50 | 132.78 |
| Human Plasma lot KC011892 | 197.63 | 11.57 | 127.51 |
| Human Plasma lot KC28719 | 195.33 | 33.42 | 126.03 |
| Human Plasma lot KC032907 | 193.77 | 30.12 | 125.02 |

*SD = standard deviation.

The assays in Table 12 used 2.5× more CJD brain homogenate than the assays in Table 13. The Control human plasma was the same for each set of experiments and was previously shown not to contain the interfering material. The results show that the covalently coupled peptoid reagent does not show any interference in binding when different plasmas are used as compared to the plasma control (and in fact shows higher signals than control plasma) compared to the biotinylated peptoid attached to the SA-beads which shows much lower signals in a number of different plasmas.

Pull-down/ELISA assays similar to those described above for human sample were carried out on a variety of samples from different animal species including mouse, Syrian hamster and sheep (both brain homogenate and blood samples from scrapie sheep and normal sheep were tested). For each of these species, the pathogenic form of the prion protein from that species was detected in samples from diseased animals but not from non-diseased animals using the peptoid reagent of the invention.

Example 4

Sandwich ELISA

A sandwich ELISA was developed to measure $PrP^C$ present in human plasma samples. To determine the levels of $PrP^C$ present in human plasma, we performed sandwich ELISA using known amounts of recombinant human PrP (rPrP) protein to develop a standard curve (FIG. 1B). The amount of $PrP^C$ in increasing amounts of human plasma was determined using the standard curve with rPrP (FIG. 1A). For the sandwich ELISA, 96-well microtiter plates were coated with the mAb SAF32 (termed "capture" antibody). This antibody binds the octarepeat region of human PrP, residues 23-90, and will bind full lengths $PrP^C$ and denatured $PrP^{Sc}$ residues 23-231. The plate was blocked with casein for 1 h at 37° C. To determine the levels of $PrP^C$ in human plasma, different amounts of plasma were added to the SFA32 coated plates and incubated for 2 h 37° C. with no shaking. Plates were washed and 3F4 antibody (antibody that binds human PrP residues 109-112) conjugated to the enzyme Alkaline Phosphatase ("detection" antibody, 3F4-AP) was added for 1 h at 37° C. The plates were washed and chemiluminescence substrate was added and light units were counted after 30 min incubation at 37° C. To quantitate the amount of $PrP^C$ we incubated the SAF-32 coated plates with increasing concentrations of recombinant human PrP using the same format of sandwich ELISA. Using the standard curve of rPrP we measured the concentration of $PrP^C$ in this batch of human plasma to be about 488 pg/70 μl.

Using this same Sandwich ELISA, we evaluated the specificity of our peptoid reagents to pull-down $PrP^{Sc C}$ or $PrP^C$ from a human plasma sample. Peptoid reagent XIIb was covalently conjugated to magnetic beads (Dynabeads M-270

Carboxylic Acid) as described. The peptoid reagent coupled beads were mixed for 1 hour in 100 ul assay that contains 70 ul of human plasma, 1% Tween-20, 1% Triton X-100 and TBS. To investigate the specific pull down of PrPSc we repeated the experiment with plasma spiked with 0.05 μl of 10% brain homogenate (BH) prepared from patient diagnosed with vCJD and as a control from normal individual. After washing, the beads were treated with 15 μl 3M GdnSCN to elute and denature PrPSc. To prevent denaturation of capture antibody, GdnSCN was diluted with 210 μl H$_2$O and solution was added to the microtiter plate coated with SAF32, bringing total volume of antigen to 250 μl. We carried out the experiment with 0.05 μl of either 10% normal brain homogenate, or 10% vCJD brain homogenate. The plates were washed and PrP was detected with 3F4-AP using a chemiluminescent AP substrate (LumiphosPlus). We find that although the amount of PrP$^c$ in plasma, when detected directly (that is, without any pull-down), measures about 887 LU, the amount or PrP$^C$ pulled-down with the peptoid reagent beads contributes only background levels of 23 LU. The same is true when 0.05 μl normal BH is spiked into 70 μl plasma. When 0.05 μl vCJD BH was spiked into 70 μl plasma, four fold increase in signal could be detected. Using rPrP as standard curve we find that peptoid reagent beads pulled down 47 pg of PrP$^{Sc}$ when spiked into plasma containing about 488 pg of PrP$^C$, while peptoid bound only 7 pg of PrP$^C$, suggesting minimum of 70 fold enrichment (Table 14).

TABLE 14

Specific pull down of PrP$^{Sc}$ with peptoid reagent beads 3M GdnSCN

|  |  | LU | pg |  |
|---|---|---|---|---|
| No Pulldown | 70 ul plasma (70%) | 887.8 | 487.7 | PrPC |
| Pulldown | 70 ul plasma (70%) | 23.3 | 6.0 | PrPC |
| Pulldown | 70 ul plasma (70%) + 50 nl 10% normal BH | 25.6 | 7.3 | PrPC |
| Pulldown | 70 ul plasma (70%) + 50 nl 10% vCJD BH | 97.1 | 47.1 | PrPSc |

Example 5 pH Denaturation with Sandwich ELISA

As an alternative to the dissociation using chaotropic agents for dissociation and denaturation of the pathogenic prion following the pull-down step, we have developed a procedure that uses either a high pH or a low pH to effect the dissociation/denaturation. The advantage of this procedure is that, unlike the situation with GdnSCN denaturation, the pH denaturation conditions can be easily reversed without significantly increasing the volume in the reaction or introducing additional washing steps.

Pull-downs were carried out as in Example 4 with magnetic beads coupled to peptoid reagent XIIb with samples of 0.1 μl of vCJD 10% brain homogenate spiked in 100 μl solution containing 70% human plasma. After mixing for 1 h at 37 C, beads were washed and treated under various pH conditions as indicated in Table 15. As a control we used 3M GdnSCN or Tris Buffer Saline (TBS) at pH 7.5 to treat the beads. After 10 min incubation at room temperature, solutions were brought to neutral pH of about 7 as indicated in the table.

Supernatant were added to 96-well microtiter plate coated with SAF32 (capture antibody) and incubated for 12 h at 4° C. Alkaline phosphatase-labeled 3F4 antibody was used for detection as described in example 4. The pull-down samples that were treated with 3M GdnSCN for dissociation and denaturation of the beads showed a signal from the vCJD spiked plasma but not the control plasma, as expected. Treatment of the pull-down samples with buffer at pH 7.5 showed no significant signal from either vCJD spiked plasma or control plasma, as expected. The pull-down samples were treated with solutions of various pH as shown. Several of the high pH and low pH treatments were able to dissociate and denature the prion protein from the beads and treatment at pH 13 was as efficient as the 3 M GdnSCN.

Significantly, while the volume of GdnSCN sample (after dilution) was 225 μl, the volume of the pH 13 treated sample was only 75 μl after neutralization.

TABLE 15

| | | | | ELISA data | | | | |
|---|---|---|---|---|---|---|---|---|
| | | | | vCJD + Plasma | | Plasma | | |
| Treatment | pH | Neutralization | Final pH | AVE | SD | AVE | SD | S/N |
| 15 μl GdnSCN 3M | 5.9 | 210 μl H20 | 6.0 | 430.4 | 26.0 | 37.7 | 21.8 | 11 |
| 70 μl TBST | 7.5 | No need | 7.5 | 25.5 | 6.8 | 11.8 | 0.4 | 2 |
| Low pH | | | | | | | | |
| H$_3$PO$_4$ (50 μl) | | NaOH (25 μl) | | | | | | |
| 0.00007M | 4 | 0.0031N | 7 | 27.0 | 8.7 | 26.8 | 7.8 | 1 |
| 0.00075M | 3 | 0.031N | 7 | 26.6 | 3.2 | 25.8 | 3.0 | 1 |
| 0.12M | 2 | 0.31N | 7 | 122.5 | 9.7 | 92.7 | 3.7 | 1 |
| 0.5M | 1 | 3.1N | 7 | 264.0 | 33.5 | 30.4 | 11.6 | 9 |
| High pH | | | | | | | | |
| NaOH (50 μl) | | NaH$_2$PO$_4$ (20 μl) | | | | | | |
| 0.0001M | 10 | 0.0003M | 7 | 34.8 | 34.4 | 197.6 | 83.8 | 0 |
| 0.001M | 11 | 0.003M | 7 | 11.8 | 0.3 | 14.6 | 1.7 | 1 |
| 0.1M | 12 | 0.03M | 7 | 76.1 | 8.1 | 16.1 | 2.1 | 5 |
| 0.1M | 13 | 0.3M | 7 | 458.1 | 9.5 | 15.1 | 2.6 | 30 |

Example 6 pH Denaturation with Direct ELISA

High and low pH dissociation and denaturation were also tested in combination with a direct ELISA format using AP-labeled 3F4 antibody for detection. The process was carried out as in Example 5 up to and including the neutralization step. The PrP in the supernatants was directly coated onto the wells of the microtiter plates in a NaHCO₃ buffer at pH 8.9. The plates were sealed and incubated overnight at 4° C. The next day the plate was washed, blocked with casein and PrP on the plaste was detected with AP-labelled 3F4 using a chemiluminescent substrate. Results are shown in Table 16.

TABLE 16

| Treatment | pH | Neutralization | Final pH | vCJD + Plasma AVE | SD | Plasma AVE | SD | S/N |
|---|---|---|---|---|---|---|---|---|
| 50 µl GdnSCN 3M | 5.9 | 50 µl NaHCO₃ | 8.5 | 60.5 | 5.7 | 5.5 | 1.8 | |
| 100 µl TBST | 7.5 | No need | 7.5 | 2.2 | 0.3 | 2.2 | 0.1 | 1 |
| Low pH Treatment H₃PO₄ (50 µl) | | NaOH (25 µl) | | | | | | |
| 0.00007M | 4 | 0.0031N | 7 | 7.6 | 2.0 | 8.7 | 1.0 | 1 |
| 0.00075M | 3 | 0.031N | 7 | 21.8 | 2.4 | 19.9 | 1.5 | 1 |
| 0.12M | 2 | 0.31N | 7 | 14.6 | 0.5 | 8.0 | 0.3 | 2 |
| 0.5M | 1 | 3.1N | 7 | 57.1 | 6.0 | 11.9 | 1.4 | 5 |
| High pH Treatment NaOH (50 µl) | | NaH₂PO₄ (20 µl) | | | | | | |
| 0.0001M | 10 | 0.0003M | 7 | 2.8 | 0.3 | 3.1 | 0.3 | 1 |
| 0.001M | 11 | 0.003M | 7 | 8.8 | 7.7 | 3.6 | 0.6 | 2 |
| 0.1M | 12 | 0.03M | 7 | 7.3 | 1.6 | 5.1 | 1.0 | 1 |
| 0.1M | 13 | 0.3M | 7 | 36.9 | 2.3 | 5.2 | 1.8 | 7 |

Example 7

Sandwich ELISA on Magnetic Beads

Typically, sandwich ELISA is performed using polystyrene microtiter plates with 96-wells, where the capture antibody is coated onto the plate and subsequent antigen binding, washing, and detection is done in the same well. However, another format which utilizes magnetic beads as the solid phase matrix can be used. In this format, the magnetic beads, which are coated with the capture antibody are mixed first with the antigen, and thereafter the detection antibody is added.

To test whether the pH dissociation and denaturation procedure that we had developed for use with the plate ELISA could be used equally well with the magnetic beads as the solid support, we carried out the following experiments. Pull-down of PrPSc from spiked human plasma samples using magnetic beads coupled to peptoid reagent XIIb was performed as previously described. The pull-down beads were denatured with 50 l of 0.1 N NaOH and neutralized with NaH₂PO₄ (20 µl). The supernatant was transferred to a clean polypropylene well.

To this solution, we added new magnetic beads that had been coated with anti-prion antibodies as the "capture" antibodies. One set of beads was coated with 3F4 antibody, another set of beads was coated with an antibody (C17) that recognizes an epitope in the C-terminal of the prion protein between residues 121 and 231. The antibody-coated beads and the eluant from the pull-down were incubated for 2 h. The beads were washed once and a AP-labeled detection antibody was added. The antibody used for the detection antibody (C2) is one that binds to the octarepeat region of PrP, residues 23-90. The beads and the detection antibody were incubated for another 2 h. The beads were then washed and chemiluminescent AP substrate was added, mixed for 30 min and chemiluminescence was measured with Luminoskan Ascent (Thermo Labsytems).

ELISA using the same capture and detection antibodies in plate format was carried out for comparison. The results are shown in Table 17. In both formats PrP$^{Sc}$ presence in 1 nl of 10% BH vCJD was detected after spiking and pulldown from solution of 70 µl plasma.

TABLE 17

| PLATE | | | | | | | | |
|---|---|---|---|---|---|---|---|---|
| vCJD | 3F4 Plate | | | | C17 Plate | | | |
| (nL BH/ asy) | Avg LU | SD | CV % | S/N | Avg LU | SD | CV % | S/N |
| 10 | 60.07 | 8.69 | 14.47 | 13.2 | 124.18 | 11.49 | 9.25 | 2.7 |
| 5 | 19.34 | 1.11 | 5.73 | 4.3 | 74.71 | 13.19 | 17.66 | 1.6 |
| 1 | 8.90 | 0.72 | 8.08 | 2.0 | 50.75 | 4.70 | 9.27 | 1.1 |
| 0 | 4.55 | 1.30 | 28.61 | 1.0 | 45.56 | 2.40 | 5.26 | 1.0 |

| Beads | | | | | | | | |
|---|---|---|---|---|---|---|---|---|
| vCJD | 3F4 Beads | | | | C17 Beads | | | |
| (nL BH/ asy) | Avg LU | SD | CV % | S/N | Avg LU | SD | CV % | S/N |
| 10 | 2.83 | 0.67 | 23.80 | 1.7 | 41.86 | 10.23 | 24.43 | 3.5 |
| 5 | 2.25 | 0.99 | 44.01 | 1.4 | 26.08 | 1.49 | 5.69 | 2.2 |
| 1 | 3.11 | 0.63 | 20.24 | 1.9 | 16.53 | 1.06 | 6.39 | 1.4 |
| 0 | 1.62 | 0.31 | 18.88 | 1.0 | 11.84 | 0.66 | 5.59 | 1.0 |

Example 8

Useful Peptides for Designing Peptoid Reagents

Non-limiting examples of peptides useful in making the peptoid reagents of the invention are derived from sequences shown in Table 18. The peptides in the table are represented by conventional one letter amino acid codes and are depicted with their amino-terminus at the left and carboxy-terminus at the right. Any of the sequences in the table may optionally include Gly linkers ($G_n$ where n=1, 2, 3, or 4) at the amino- and/or carboxy-terminus. Amino acids in square brackets indicate alternative residues that can be used at that position in different peptides. Round brackets indicate the residue(s) may be present or absent from the peptide reagent. Double round brackets (e.g., SEQ ID NO: 111) followed by a "2" indicate that the sequence includes two copies of the peptide between the double brackets. The residue following the copy number designation (e.g., "K" in SEQ ID NO: 111) indicates the residue from which each copy of the peptide between the double brackets extends. Thus, SEQ ID NO: 111 is a dimer of QWNKPSKPKTN peptide sequences (i.e., SEQ ID NO: 14), each linked by their carboxy-terminus to a lysine (K) residue via the a- and e-amino functional groups of lysine. Sequences including "MAPS" indicate peptides with multiple antigenic sites. The number preceding the term "branches" indicates the number of copies. Thus, SEQ ID NO: 112 contains 4 copies of GGGKKRPKPGGWNTGGG, which is SEQ ID NO: 67 with Gly linkers at each terminus, while SEQ ID NO: 113 contains 8 copies of GGGKKRPKPGGWNTGGG, which again is SEQ ID NO: 67 with Gly linkers at each terminus.

TABLE 18

Example peptide sequences for making peptoid reagents of the invention.

| Peptide sequence | SEQ ID NO |
| --- | --- |
| KKRPK | 12 |
| MANLGCWMLVLFVATWSDLGLC | 13 |
| (GGG)QWNKPSKPKTN | 14 |
| QWNKPSKPKTNMKHV | 15 |
| NQNN[N/T]FVHDCVNIT[I/V]K[Q/E]HTVTTTTKGEN | 16 |
| TFFKGENFTETD | 17 |
| GENFTETD | 18 |
| GENFTETD[V/I]K[M/I]MERVVEQMC[I/V]TQY[E/Q]ESQAYY[Q/D](G)(R)R[G/S][S/A]S | 19 |
| NQNN[N/T]FVHDCVNIT[I/V]K[Q/E]HTVTTTTKGENFTETD[V/I]K[M/I]MERVVEQMC[I/V]TQY[E/Q]ESQAYY[Q/D](G)(R)R[G/S][S/A]S | 20 |
| [A/V/T/M][V/I]LFSSPPVILLISFLIFL[I/M]VG | 21 |
| G[N/S]D[W/Y]EDRYYRENM[H/Y]RYPNQVYYRP[M/V]D[Q/E/R]Y[S/N]NQN[N/T]FVH | 22 |
| N[N/T]FVHDCVNIT[I/V]K[Q/E]HTVTTTTK | 23 |
| VYYR | 24 |
| RYPNQVYYRP[M/V]D[Q/E/R] | 25 |
| KKRPKPGG(G)WNTGGSRYPGQGSPGGNRYPPQGG | 26 |
| WNTGGSRYPGQGSPGGNRYPPQGG(G) | 27 |
| WNTGGSRYPGQGSPGGNRYPPQGG(G)[G/T]WGQPHGG | 28 |
| GGWGQGGGTHSQWNKPSKPKTN | 29 |
| GGTHSQWNKPSKPKTN | 30 |
| WNTGGSRYPGQGSPGGNRYPPQGG(G)[G/T]WGQPHGGGWGQPHGGGWGQPHGG | 31 |
| GQPHGGGW | 32 |
| RPIIHFGSDYEDRYYRENMHR | 33 |
| RPMIHFGNDWEDRYYRENMYR | 34 |
| (GGGG)C(GG)GGWGQGGGTHNQWNKPSKPKTNLKHV(GGGG)C | 35 |
| (GGGG)GGWGQGGGTHNQWNKPSKPKTNLKHV | 36 |
| GGWGQGGGTHNQWNKPSKPKTNLKHV(GGGG) | 37 |
| [M/L]KH[M/V] | 38 |
| KPKTN[M/L]KH[M/V] | 39 |
| C(GG)GGWGQGGGTHNQWNKPSKPKTNLKHV(GGGG)C | 40 |
| SRPIIHFGSDYEDRYYRENMHRYPN | 41 |
| PMIHFGNDWEDRYYRENMYRPVD | 42 |
| AGAAAAGAVVGGLGGYMLGSAM | 43 |
| RPMIHFGNDWEDRYYRENMYR(GGG) | 44 |
| GGGRPMIHFGNDWEDRYYRENMYRGG | 45 |
| (GG)C(GGG)RPMIHFGNDWEDRYYRENMYR(GGG)C | 46 |
| AGAAAAGAVVGGLGG | 47 |
| GGLGG | 48 |
| LGS | 49 |
| QWNKPSKPKTN(GGG) | 50 |
| QWNKPSKPKTN(GGG)QWNKPSKPKTN | 51 |
| QWNKPSKPKTNLKHV(GGG) | 52 |
| GGWGQGGGTHNQWNKPSKPKTN | 53 |
| GGTHNQWNKPSKPKTN | 54 |
| (GGG)AGAAAAGAVVGGLGGYMLGSAM | 55 |
| (GGG)AGAAAAGAVVGGLGG | 56 |
| (KKK)AGAAAAGAVVGGLGGYMLGSAM | 57 |
| YMLGSAM[S/N]R | 58 |
| [S/N]RP[M/I/L][I/L]H | 59 |
| YMLGSAM[S/N]RP[M/I/L][I/L]H | 60 |
| YMLGSAM[S/N]RP[M/I/L][I/L]HFG[N/S]D | 61 |
| [W/Y]EDRYYRENM[H/Y]RYPNQVYYRP[M/V]D[Q/E/R]Y | 62 |

TABLE 18-continued

Example peptide sequences for making peptoid reagents of the invention.

| Peptide sequence | SEQ ID NO |
|---|---|
| [W/Y]EDRYYRENM[H/Y]RYPNQVYYRP[M/V]D[Q/E/R]Y[S/N]NQN[N/T] | 63 |
| D[Q/E/R]Y[S/N]NQN[N/T] | 64 |
| (KKK)AGAAAAGAVVGGLGG | 65 |
| (GGG)KKRPKPGGWNTGGSRYPGQGS | 66 |
| (GGG)KKRPKPGGWNTGG | 67 |
| (GGG)KKRPKPGG | 68 |
| PHGGGWGQHGGSWGQPHGGSWGQ | 69 |
| PHGGGWGQPHGGSWGQ | 70 |
| PHGGGWGQ | 71 |
| (GGG)KKRPKPGGGKKRPKPGG | 72 |
| (GGG)GPKRKGPK | 73 |
| (GGG)WNTGGSRYPGQGS | 74 |
| (GGG)WNKPSKPKT | 75 |
| (GGG)RPMIHFGNDWEDRYYRENMYR(GG)C | 76 |
| QWNKPSKPKTNLKHV(GGG) | 77 |
| (GGG)AGAAAAGAVVGGLGGYMLGSAM | 78 |
| (GGG)NKPSKPK | 79 |
| (GGG)KPSKPK | 80 |
| (GGG)KKRPKPGGGQWNKPSKPKTN | 81 |
| KKKAGAAAAGAVVGGLGGYMLGSAMDDD | 82 |
| DDDAGAAAAGAVVGGLGGYMLGSAM | 83 |
| KKKAGAAAAGAVVGGLGGYMLGSAMKKK | 84 |
| (GGG)KKKKKKKK | 85 |
| DDDAGAAAAGAVVGGLGGYMLGSAMDDD | 86 |
| (GGG)NNKQSPWPTKK | 87 |
| DKDKGGVGALAGAAVAAGGDKDK | 88 |
| (GGG)QANKPSKPKTN | 89 |
| (GGG)QWNKASKPKTN | 90 |
| (GGG)QWNKPSKAKTN | 91 |
| (GGG)QWNAPSKPKTN | 92 |
| (GGG)QWNKPSAPKTN | 93 |
| (GGG)QWNKPSKPATN | 94 |
| (GGG)QWNKASKAKTN | 95 |
| (GGG)KKRAKPGG | 96 |
| (GGG)KKRPKAGG | 97 |
| (GGG)KKRAKAGG | 98 |
| (GGG)QWNKASKPKTN | 99 |
| (GGG)QWAKPSKPKTN | 100 |
| (GGG)QWNKPAKPKTN | 101 |
| (GGG)QWNKPSKPKAN | 102 |
| (GGG)QWNKPSKPKTA | 103 |
| (GGG)AKRPKPGG | 104 |
| (GGG)KARPKPGG | 105 |
| (GGG)KKAPKPGG | 106 |
| (GGG)KKRPAPGG | 107 |
| (GGG)KKAPKAGG | 108 |
| (GGG)KKRPKPGGGWNTGG | 109 |
| QWNKPSKPKTNGGGQWNKPSKPKTNGGGQWNKPSKPKTN | 110 |
| ((QWNKPSKPKTN))2K | 111 |
| 4-branchMAPS-GGGKKRPKPGGWNTGGG | 112 |
| 8-branchMAPS-GGGKKRPKPGGWNTGGG | 113 |
| KKKAGAAAAGAVVGGLGG-CONH2 | 114 |
| DLGLCKKRPKPGGXWNTGG | 115 |
| DLGLCKKRPKPGGXWNTG | 116 |
| DLGLCKKRPKPGGXWNT | 117 |
| DLGLCKKRPKPGGXWN | 118 |
| DLGLCKKRPKPGGXW | 119 |
| DLGLCKKRPKPGGX | 120 |
| LGLCKKRPKPGGXWNTG | 121 |
| LGLCKKRPKPGGXWNT | 122 |
| LGLCKKRPKPGGXWN | 123 |
| LGLCKKRPKPGGXW | 124 |
| LGLCKKRPKPGGX | 125 |
| GLCKKRPKPGGXWNTGG | 126 |
| GLCKKRPKPGGXWNTG | 127 |
| GLCKKRPKPGGXWNT | 128 |
| GLCKKRPKPGGXWN | 129 |
| GLCKKRPKPGGXW | 130 |
| GLCKKRPKPGGX | 131 |
| LCKKRPKPGGXWNTGG | 132 |
| LCKKRPKPGGXWNTG | 133 |
| LCKKRPKPGGXWNT | 134 |

TABLE 18-continued

Example peptide sequences for making peptoid reagents of the invention.

| Peptide sequence | SEQ ID NO |
|---|---|
| LCKKRPKPGGXWN | 135 |
| LCKKRPKPGGXW | 136 |
| LCKKRPKPGGX | 137 |
| CKKRPKPGGXWNTGG | 138 |
| CKKRPKPGGXWNTG | 139 |
| CKKRPKPGGXWNT | 140 |
| CKKRPKPGGXWN | 141 |
| CKKRPKPGGXW | 142 |
| CKKRPKPGGX | 143 |
| KKRPKPGGXWNTGG | 144 |
| KKRPKPGGXWNTG | 145 |
| KKRPKPGGXWNT | 146 |
| KKRPKPGGXWN | 147 |
| KKRPKPGGXW | 148 |
| KKRPKPQGX | 149 |
| DVGLCKKRPKPGGXWNTGG | 150 |
| DVGLCKKRPKPGGXWNTG | 151 |
| DVGLCKKRPKPGGXWNT | 152 |
| DVGLCKKRPKPGGXWN | 153 |
| DVGLCKKRPKPGGXW | 154 |
| DVGLCKKRPKPGGX | 155 |
| VGLCKKRPKPGGXWNTG | 156 |
| VGLCKKRPKPGGXWNT | 157 |
| VGLCKKRPKPGGXWN | 158 |
| VGLCKKRPKPGGXW | 159 |
| VGLCKKRPKPGGX | 160 |
| THSQWNKPSKPKTNMKHM | 161 |
| THSQWNKPSKPKTNMKH | 162 |
| THSQWNKPSKPKTNMK | 163 |
| THSQWNKPSKPKTNM | 164 |
| THSQWNKPSKPKTN | 165 |
| HSQWNKPSKPKTNMKHM | 166 |
| HSQWNKPSKPKTNMKH | 167 |
| HSQWNKPSKPKTNMK | 168 |
| HSQWNKPSKPKTNM | 169 |
| HSQWNKPSKPKTN | 170 |
| SQWNKPSKPKTNMKHM | 171 |
| SQWNKPSKPKTNMKH | 172 |
| SQWNKPSKPKTNMK | 173 |
| SQWNKPSKPKTNM | 174 |
| SQWNKPSKPKTN | 175 |
| QWNKPSKPKTNMKHM | 176 |
| QWNKPSKPKTNMKH | 177 |
| QWNKPSKPKTNMK | 178 |
| QWNKPSKPKTNM | 179 |
| THSQWNKPSKPKTNMXHV | 180 |
| HSQWNKPSKPKTNMKHV | 181 |
| SQWNKPSKPKTNMKHV | 182 |
| QWNKPSKPKTNMKHV | 183 |
| THGQWNKPSKPKTNMXHM | 184 |
| THGQWNKPSKPKTNMKH | 185 |
| THGQWNKPSKPKTNMK | 186 |
| THGQWNKPSKPKTNM | 187 |
| THGQWNKPSKPKTN | 188 |
| HGQWNXPSKPKTNMKHM | 189 |
| HGQWNKPSKPKTNMKH | 190 |
| HGQWNXPSKPKTNMK | 191 |
| HGQWNKPSKPKTNM | 192 |
| HGQWNKPSKPKTN | 193 |
| GQWNKPSKPKTNMKHM | 194 |
| GQWNKPSKPKTNMKH | 195 |
| GQWNKPSKPKTNMK | 196 |
| GQWNKPSKPKTNM | 197 |
| GQWNKPSKPKTN | 198 |
| THGQWNKPSKPKTNMKHV | 199 |
| HGQWNKPSKPKTNMKHV | 200 |
| GQWNKPSKPKTNMKHV | 201 |
| THNQWNKPSKPKTNMKHM | 202 |
| THNQWNKPSKPKTNMKH | 203 |
| THNQWNKPSKPKTNMK | 204 |
| THNQWNKPSKPKTNM | 205 |
| THNQWNKPSKPKTN | 206 |
| HNQWNKPSKPKTNMKHM | 207 |

TABLE 18-continued

Example peptide sequences for making peptoid reagents of the invention.

| Peptide sequence | SEQ ID NO |
| --- | --- |
| HNQWNKPSKPKTNMKH | 208 |
| HNQWNKPSKPKTNMK | 209 |
| HNQWNKPSKPKTNM | 210 |
| HNQWNKPSKPKTN | 211 |
| NQWNKPSKPKTNMKHM | 212 |
| NQWNKPSKPKTNMKH | 213 |
| NQWNKPSKPKTNMK | 214 |
| NQWNKPSKPKTNM | 215 |
| NQWNKPSKPKTN | 216 |
| THNQWNKPSKPKTNMKHV | 217 |
| HNQWNKPSKPKTNMKHV | 218 |
| NQWNKPSKPKTNMKHV | 219 |
| PHGGGWGQPHGGGWGQPHGGGWGQ | 220 |
| GGWGQGGGTHSQWNKPSKPKTNMKHM | 221 |
| QWNKPSKPKTNMKHMGGGQWNKPSKPKTNMKHM | 222 |
| GGWGQGGGTH[N/S]QWNKPSKPKTN[L/M]KH[V/M](GGGG) | 223 |
| PHGGGWGQHG[G/S]SWGQPHGG[G/S]WGQ | 224 |
| QWNKPSKPKTN[L/M]KH[V/M](GGG) | 225 |
| GGGAWNKPSKPKTN | 226 |
| 4-branchMAPS-(GGG)QWNKPSKPKTN(GGG) | 227 |
| 8-branchMAPS-(GGG)KKRPKPGGWNT(GGG) | 228 |

Example 9

Solid-phase Submonomer Synthesis Protocol for Peptoids

General Experimental. Solvents are reagent grade and used without further purification. Bromoacetic acid was obtained from Aldrich (99% grade) and DIC was obtained from Cheminplex International. All reactions and washings are performed at 35° C. unless otherwise noted. Washing of the resin refers to the addition of a wash solvent (usually DMF or DMSO) to the resin, agitating the resin so that a uniform slurry is obtained (typically for about 20 seconds), followed by thorough draining of the solvent from the resin. Solvents are best removed by vacuum filtration through the fritted bottom of the reaction vessel until the resin appears dry (typically about 10 seconds). Resin slurries were agitated via bubbling argon up through the bottom of the fritted vessel. Solvents used to dissolve reagents should be degassed prior to use by sonication under house vacuum for 5 minutes. For wash solvents, it is very convenient to have dispensers containing DMF, DMSO and dichloromethane available with adjustable volumes (1-5 mL).

It is preferred not to stop a synthesis at the dimer stage because dimers can cyclize upon storage over a long period of time to form diketopiperazines. The preferred place to pause a synthesis is after the displacement washes.

Initial Resin Swelling and Fmoc Deprotection. A fritted reaction vessel is charged with 100 mg of Fmoc-Rink amide resin (0.50 mmol/g resin). To the resin is added 2 mL of DMF and this solution is agitated for 5 minutes to swell the resin. A glass rod may be used to break up chunks of resin, if necessary. The DMF is then drained. The Fmoc group is then removed by adding 2 mL of 20% piperidine in DMF to the resin. This is agitated for 1 minute, then drained. Another 2 mL of 20% piperidine in DMF is added to the resin and agitated for 20 minutes, then drained. The resin is then washed with DMF (5×2 mL).

Submonomer Synthesis Cycle. The deblocked amine is then acylated by adding to the resin 1.13 mL of 1.2 M bromoacetic acid in DMF, followed by 200 µL (0.93 equiv.) neat N,N'-diisopropylcarbodiimide (DIC). This solution is agitated for 20 minutes at 35° C., then drained. The resin is then washed with DMF (3×2 mL).

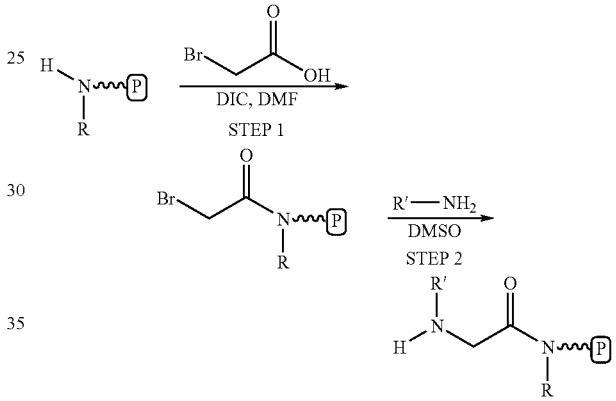

The acylation step is then followed by nucleophilic displacement with a primary amine. To the washed resin is added 0.85 mL of a 1 M solution of the amine in NMP. This solution is agitated for 30 min at 35° C. and then drained. The resin is then washed with DMF (3×2 mL). This completes one reaction cycle.

The acylation/displacement cycle is repeated until the desired oligomer is obtained, for example, from 3 to about 30 times.

Biotin and Thiol Group Conjugation. Optionally, biotin was coupled to the N-terminus by the addition of 2.0 mL of a solution of biotin (0.4 M) and HOBt (0.4 M) in DMSO, followed by the addition of 1.05 equivalents of neat DIC. The reaction mixture was agitated for 1 hour at 35° C., after which the reaction mixture was drained and the resin was washed with DMSO (2×3 mL) followed by DMF (3×2 mL). Optionally, a thiol group was incorporated by the incorporation of cysteine, which was added via an amino acid coupling step: Fmoc-Cys(Trt) (NovaBiochem) was coupled to the N-terminus by the addition of 2.0 mL of a solution of Fmoc-Cys(Trt) (0.4 M) and HOBt (0.4 M) in DMF, followed by the addition of 1.05 equivalents of neat DIC. The reaction mixture was agitated at 35° C. for 1 hour, after which the reaction mixture was drained and the resin was washed with DMF (3×3 mL). The Fmoc group is then removed by adding 2 mL of 20% piperidine in DMF to the resin. This is agitated for 1 minute, then drained. Another 2 mL of 20% piperidine in DMF is added to the resin and agitated for 20 minutes, then drained. The resin is then washed with DMF (5×2 mL).

Cleavage (for 50 µmol resin). After the synthesis reaction and resin washing, the resin is washed with dichloromethane (2×2 mL) and air dried for one minute. The dried resin is placed in a glass scintillation vial containing a teflon micro stir bar, and approximately 5 mL of TFA/triisopropylsilane/water 95/2.5/2.5 (v/v/v) is added. This solution is stirred for 15 minutes. Filter the cleavage mixture for each sample through an 8 mL solid phase extraction (SPE) column fitted with a 20 µm polyethylene frit into a 50 mL polypropylene conical centrifuge tube. The resin is then washed with 1 mL of the 95% TFA and the filtrates are combined. The filtrate is then diluted with an equal volume of water in the centrifuge tube. This solution is then frozen and lyophilized to dryness. The dried product is then taken up in 10 mL of 1:1 acetonitrile/water acid and again lyophilized to dryness.

Oligomer Characterization. Individual peptoid oligomers are analyzed by reverse-phase HPLC on C-18 columns (Vydac, 5 µm, 300 Å, 4.5×250 mm). A linear gradient of 0-80% B in 40 min is used at a flow rate of 1 mL/min (solvent A=0.1% TFA in water, solvent B=0.1% TFA in acetonitrile). Major peaks are collected and submitted to electrospray MS analysis to determine the molecular weights.

Peptoid Purification. Peptoids are purified by reverse-phase HPLC prior to use by the biologists. Typically these compounds are analyzed and purified on C18 columns. Thus, the compounds are dissolved in a small amount of 10% acetonitrile/water and purified on a 50×20 mm ID DuraGel HS C18 column (Peeke Scientific). A linear gradient of 5-65% B in 40 min is used at a flow rate of 30 mL/min (solvent A=0.1% TFA in water, solvent B=0.1% TFA in acetonitrile). The combined product fractions are combined and lyophilized to a white powder.

Example 10

Pulldown Efficiency of Peptoid Reagent XIIb

The capacity of peptoid reagent XIIb covalently bound to beads was tested by the pulldown assay as described below.

vCJD or normal brain homogenate (BH) was spiked into 50% pooled normal human plasma in TBS with 1% Tween20 and 1% Triton-X 100. Control samples were not spiked with either. Then 100 µL of each sample (containing 10 nL or none of 10% BH) were mixed with 3 µL of XIIb-beads (30 mg/mL) and the resulting mixture was incubated at 37° C. for 1 hr with constant shaking at 750 rpm. The beads were next washed four times with TBST containing 0.05% Tween20, and PrP$^{Sc}$ bound to beads was dissociated by addition of 0.1N NaOH. The denatured prion protein was later neutralized by 0.3 M NaH$_2$PO$_4$ and transferred to ELISA plate.

The pull-down efficiency was calculated by comparing the signals from the pulldown samples to those from identical samples that were denatured by guanidinium thiocyanate (GdnSCN) without any pulldown. Prion protein from vCJD or normal brain was denatured by mixing equal volume of 5% BH and 6 M GdnSCN, and incubated at room temperature for 10 min. The sample was then diluted in TBST to the same concentration of pulldown samples, with TBST only as control. 100 µL of each directly denatured sample was later transferred to the same ELISA plate for pulldown samples.

The ELISA plate was coated by capture antibody 3F4 at 2.5 ug/mL in 0.1M NaHCO$_3$. The coating procedure was performed at 4° C. overnight, and then washed three times by TBST. The plate was next blocked by 1% casein in TBS at 37° C. for 1 hr. Prion protein from both pulldown and directly denatured samples were incubated in ELISA plate with 3F4 for 1 hr at 37° C., with constant shaking at 300 rpm, and the plate was washed six times with TBST. Alkaline phosphatase (AP) conjugated detection antibody was diluted to 0.1 µg/mL in 0.1% casein in TBST, and then added to ELISA plate. The plate was later incubated at 37° C. for 1 hr, and washed six times by TBST. The signal was developed using enhanced Lumi-Phos Plus chemiluminescent substrate, and read by a luminometer in relative light units (RLU).

Results are shown in Table 19. Prion protein from brain tissue can be completely denatured by 3 M GdnSCN and detected by its antibody. In this experiment, we compared signal generated by prion protein pulldown using XIIb-beads to signal obtained from directly denatured protein by GdnSCN. Data showed that the background (no BH) for pulldown and directly denatured samples was 9.0 and 7.7 RLU respectively. Directly denatured 10 nL of 10% normal BH had signal of 14.6 RLU, reflecting PrPc level in normal brain. Meanwhile, 10 nL of 10% normal BH detected by pulldown method showed reading of 9.9 RLU, which is similar to its background. This demonstrated the specificity of peptoid XIIb. When 10 nL of 10% vCJD sample was tested by pulldown and direct denature methods, data showed 53.0 and 56.3 RLU, which means the pulldown efficiency of XIIb-beads reached almost 100%.

TABLE 19

| | vCJD BH (RLU) | | | Nomal BH (RLU) | | | No BH (RLU) | | |
|---|---|---|---|---|---|---|---|---|---|
| | ave | sd | % cv | ave | sd | % cv | ave | sd | % cv |
| Pulldown | 53.0 | 6.5 | 12.3 | 9.9 | 0.8 | 8.0 | 9.0 | 1.1 | 12.3 |
| No pulldown | 56.3 | 2.6 | 4.6 | 14.6 | 0.7 | 4.5 | 7.7 | 2.3 | 29.4 |

Example 11

Distinguishing Prion Strains

One can detect the structural differences between prion strains by measuring their different thermodynamic properties of unfolding. Incubation of $PrP^{Sc}$ with increasing concentrations of chemical denaturant can yield a denaturation profile of the prion conformer that is characteristic of each strain. Previous studies used proteinase K (PK) resistance to measure the proportion of $PrP^{Sc}$ that remained folded after treatment with denaturant. Here, it was tested whether peptoid reagent XIIb could also be used to distinguish folded and unfolded $PrP^{Sc}$, thus allowing the measurement of conformational states in PK-sensitive strains where denaturation profiles cannot be measured by conventional methods.

To generate a denaturation profile for a vCJD strain, a vCJD brain homogenate (NIBSC CJD Resource Centre) was incubated with various concentrations of guanidine hydrochloride before the samples were diluted and subjected to pulldown using peptoid reagent XIIb (See Example 3 and XIIb Pulldown description below). Material bound to XIIb was then eluted and detected by sandwich ELISA assay. A graphical representation of $PrP^{Sc}$ pulled down at each concentration of denaturant demonstrated that the concentration of guanidine hydrochloride was inversely proportional with the fraction of folded $PrP^{Sc}$ pulled down by XIIb. The data points formed a single sigmoidal curve suggesting the existence of one $PrP^{Sc}$ conformer in the brain homogenate that unfolds at one major transition (See FIG. 4, open dots). Therefore, it is believed that XIIb recognizes a structural epitope on PrP$^{Sc}$ that is disrupted upon treatment with chemical denaturant. Analysis of a sporadic CJD strain (sCJD, NIBSC CJD Resource Centre) resulted in a similar sigmoidal curve that was shifted to the right of the denaturation profile for vCJD (See FIG. 4, grey dots), illustrating that the structural epitope recognized by XIIb is believed to be more stable in the sCJD strain when compared to the vCJD strain. Analysis of each strain consistently yielded the equivalent pattern, allowing definition of the curve with one characteristic value as a measure of the relative conformational stability of PrP$^{Sc}$: the GdnHCl concentration found at the half-maximal denaturation (GdnHCl$_{1/2}$). The denaturation profile of vCJD had a GdnHCl$_{1/2}$ of 1.6 M GdnHCl. By contrast, an sCJD brain homogenate was more stable to guanidine denaturation, with a GdnHCl$_{1/2}$ of 2.0 M GdnHCl. Therefore, XIIb can be used as a tool to dissect the conformational variability between prion strains.

XIIb Pulldown

Infectious brain homogenate (75-200 nL, 10%) was denatured in guanidine solutions ranging in concentrations from 0-4 M for 1 hr at room temperature. Following denaturation, all samples were adjusted to a final concentration of 0.1 M guanidine hydrochloride in TBSTT, and folded PrP$^{Sc}$ was pulled down with XIIb-beads using standard pulldown procedures. Pulled down material was eluted and measured by sandwich ELISA assay in triplicate with C17 capture antibodies and 3F4-AP detection antibodies.

As those skilled in the art will appreciate, numerous changes and modifications can be made to the preferred embodiments of the invention without departing from the spirit of the invention. It is intended that all such variations fall within the scope of the invention. It is also intended that each of the patents, applications, and printed publications, including books, mentioned in this patent document be hereby incorporated by reference in their entirety.

What is claimed is:

1. A peptoid reagent having a formula of:

$$X^a\text{-}(Q)_n\text{-}X^b$$

wherein: $\text{-}(Q)_n\text{-}$ defines a peptoid region comprising SEQ ID NO: 229, 230, 231, 232, 233, 234, 235, 236, 237, 238, 239, 240, or 241;

$X^a$ is H, $(C_1\text{-}C_6)$alkyl, cycloalkyl, aryl, aralkyl, heteroaryl, heteroarylalkyl, heterocycloalkyl, $(C_1\text{-}C_6)$acyl, amino $(C_{1\text{-}6})$acyl, an amino acid, an amino protecting group, or a polypeptide of 2 to about 100 amino acids, wherein $X^a$ is optionally substituted by a conjugate moiety that is optionally attached through a linker moiety; and $X^b$ is H, $(C_1\text{-}C_6)$alkyl, aryl, aralkyl, heteroaryl, heteroarylalkyl, heterocycloalkyl, amino, alkylamino, dialkylamino, hydroxyl, $(C_1\text{-}C_6)$alkoxy, aryloxy, aralkoxy, a carboxy protecting group, an amino acid, or a polypeptide of 2 to about 100 amino acids, wherein $X^b$ is optionally substituted by a conjugate moiety that is optionally attached through a linker moiety.

2. The peptoid reagent of claim 1 wherein $X^b$ is an amino acid optionally substituted by a conjugate moiety that is optionally attached through a linker moiety.

3. The peptoid reagent of claim 1 wherein the peptoid region $\text{-}(Q)_n\text{-}$ is polyionic at physiologically relevant pH.

4. The peptoid reagent of claim 1 wherein the peptoid region $\text{-}(Q)_n\text{-}$ has a net charge of at least 3+ at physiologically relevant pH.

5. The peptoid reagent of claim 1 wherein the peptoid region $\text{-}(Q)_n\text{-}$ comprises SEQ ID NO: 229, 230, 232, 233, 237, 238, 239, or 240.

6. The peptoid reagent of claim 1 wherein the peptoid region $\text{-}(Q)_n\text{-}$ comprises SEQ ID NO: 230, 237, 238, 239, or 240.

7. The peptoid reagent of claim 1 wherein the peptoid region $\text{-}(Q)_n\text{-}$ comprises SEQ ID NO: 240.

8. The peptoid reagent of claim 1 comprising at least one conjugate moiety.

9. The peptoid reagent of claim 8 wherein the conjugate moiety is attached through a linker moiety.

10. The peptoid reagent of claim 8 wherein the conjugate moiety is a cross-linking agent or a binding agent.

11. The peptoid reagent of claim 8 wherein the conjugate moiety comprises biotin or a mercapto group.

12. A peptoid reagent selected from:
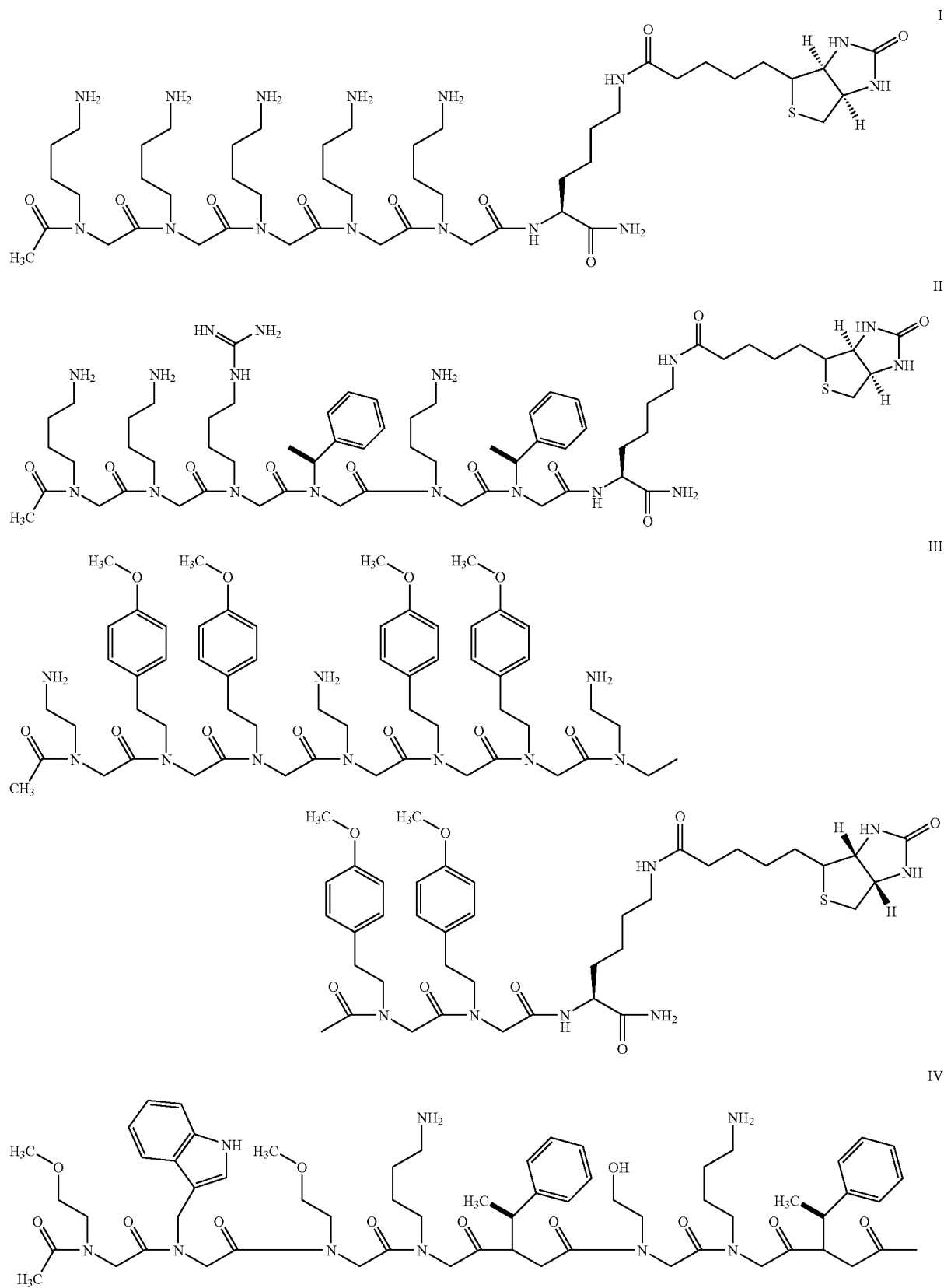

-continued
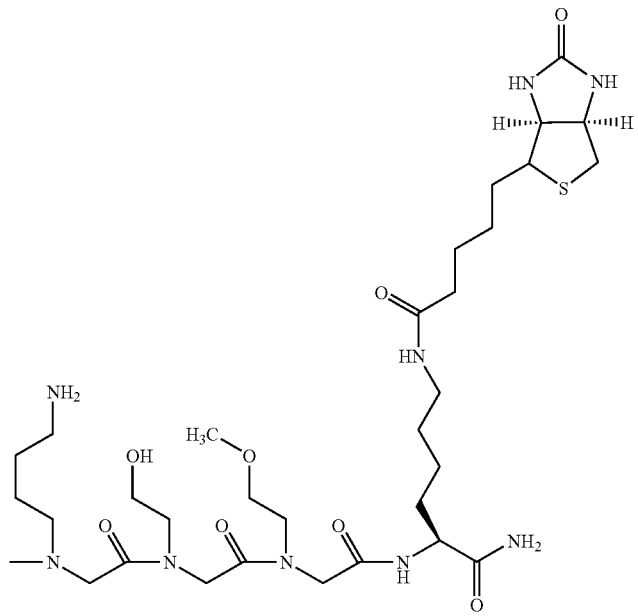
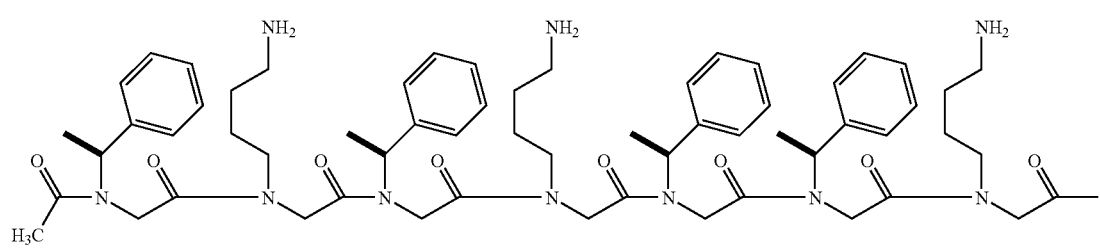
v
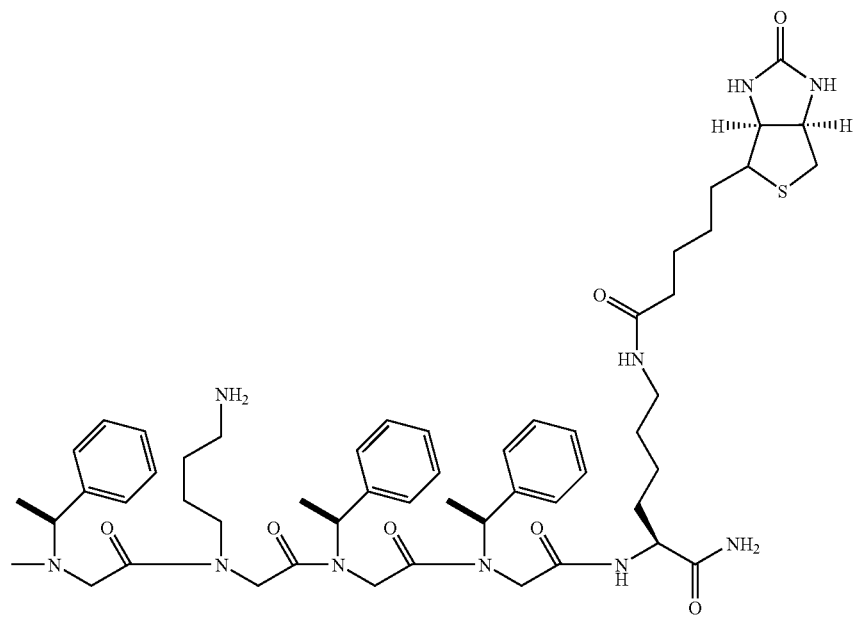

-continued
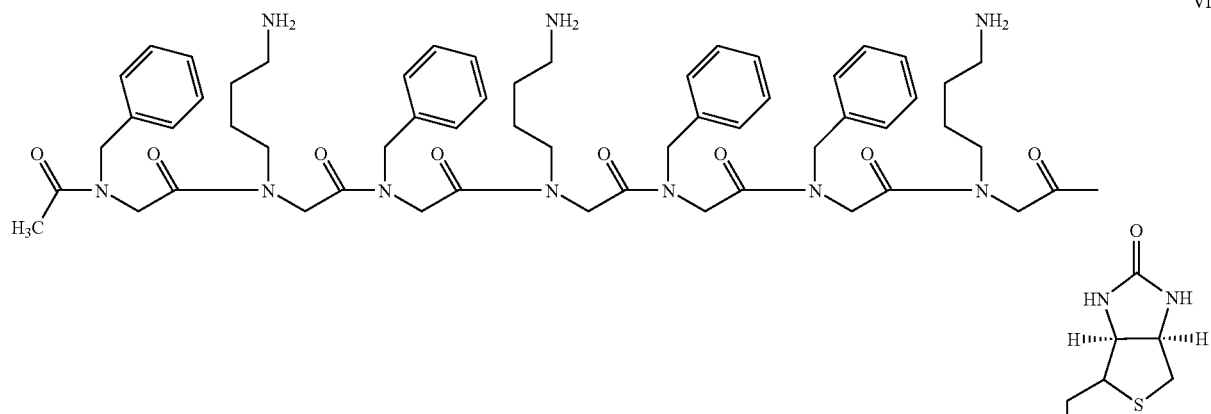
VI
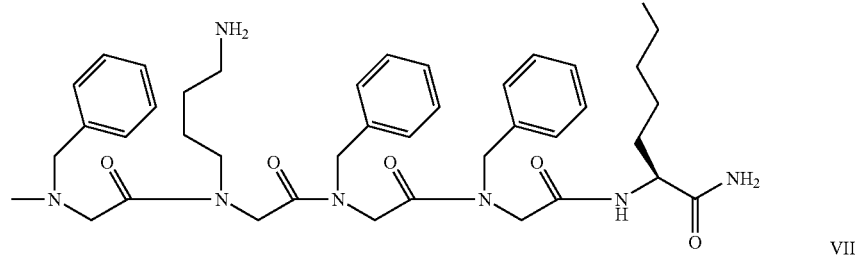
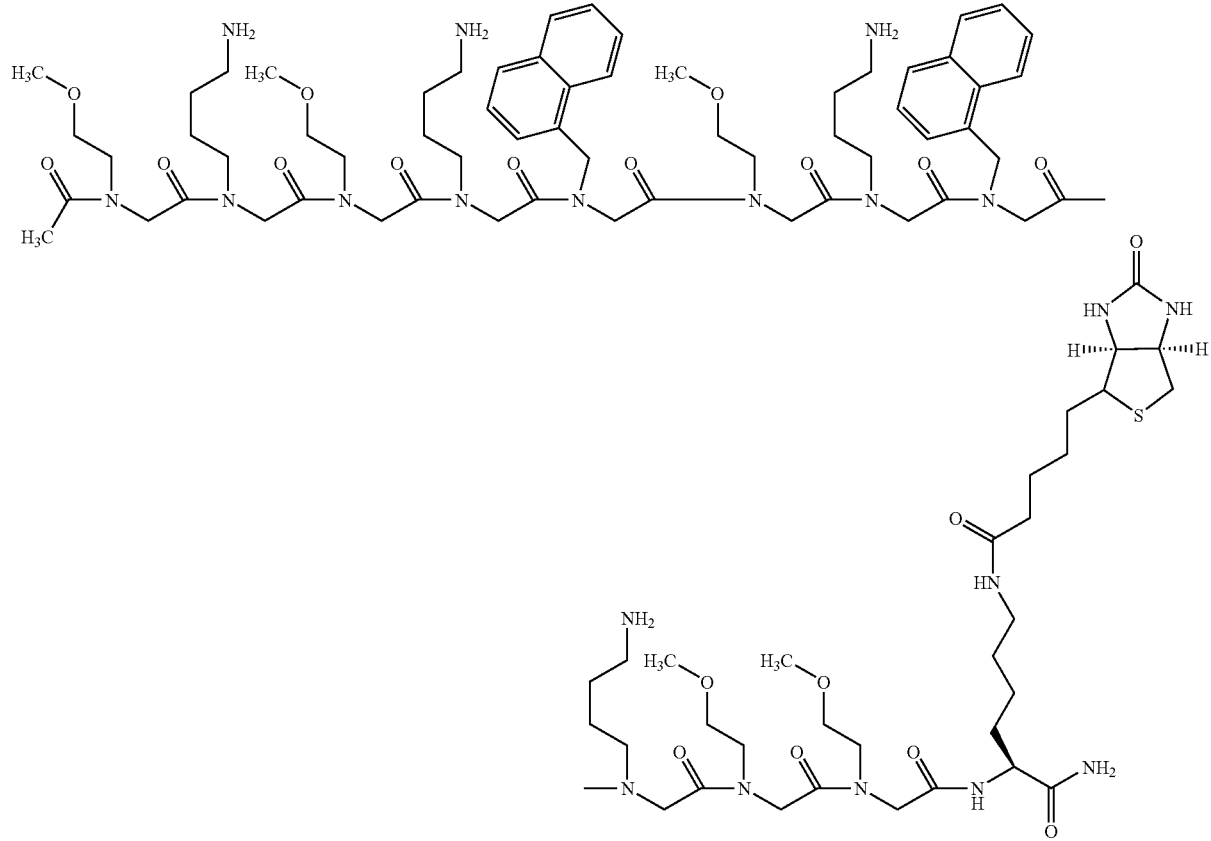
VII

-continued
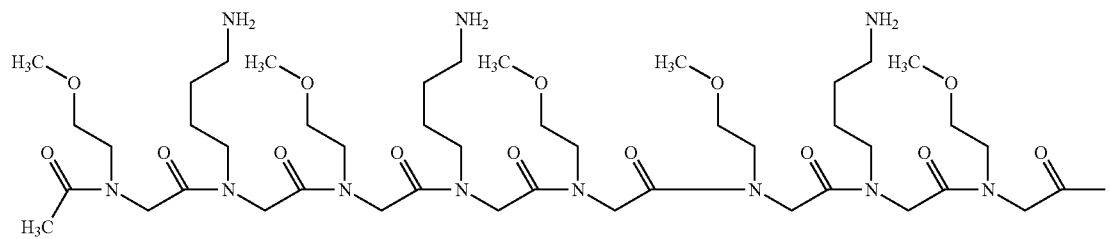
VIII
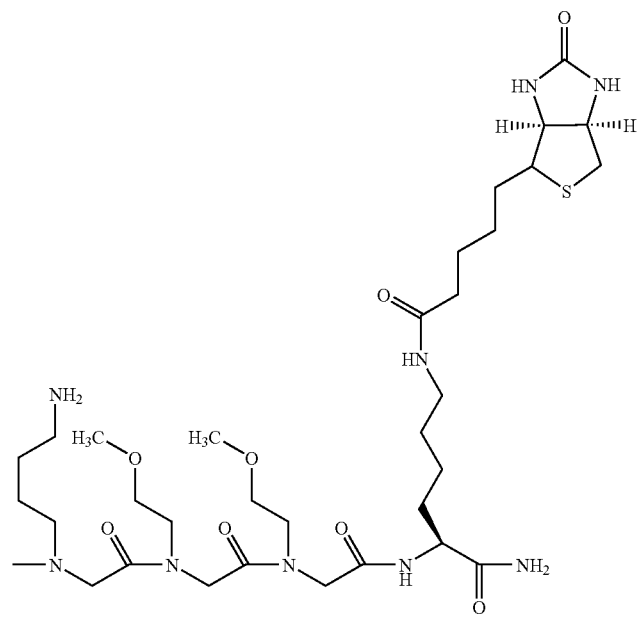
IX
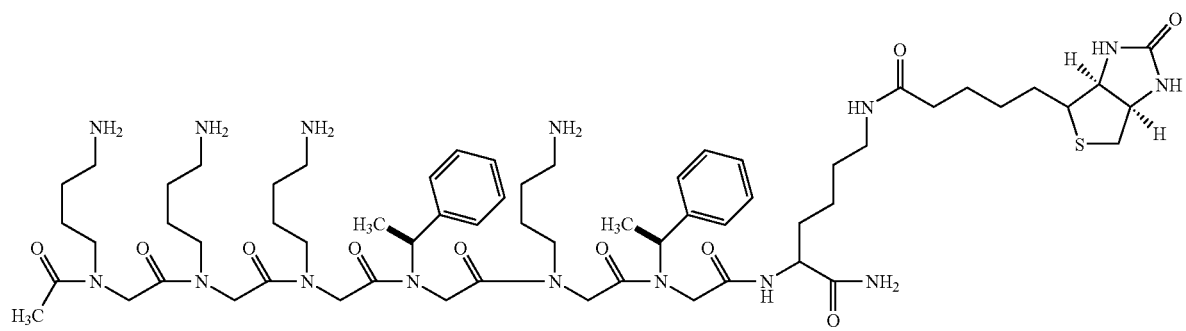
X
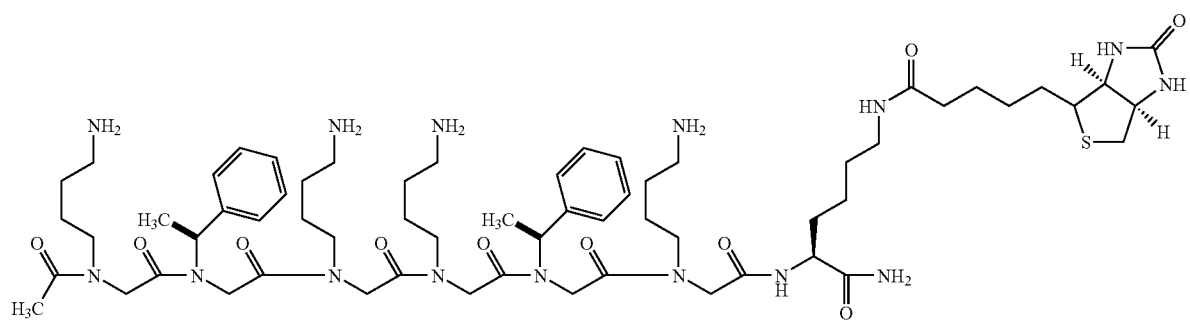

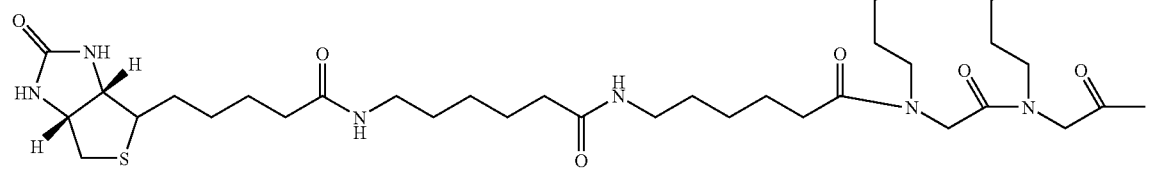
XIa
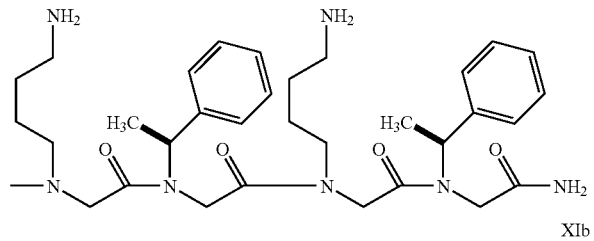
XIb
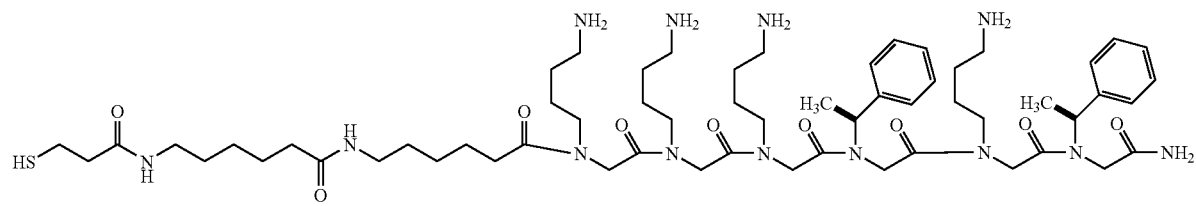
XIIa
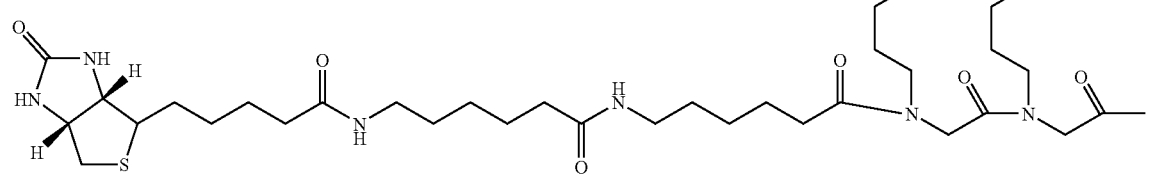
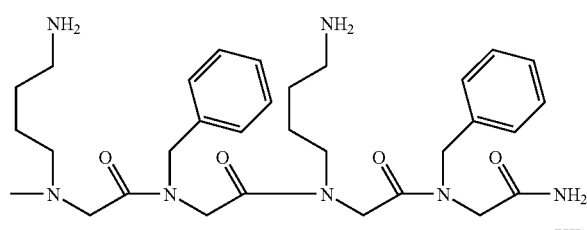
XIIb
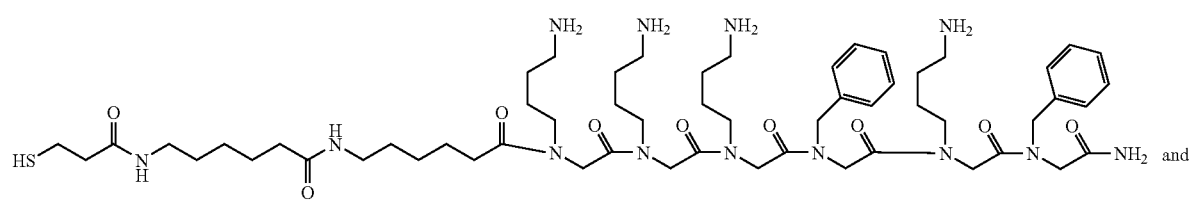 and
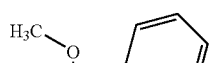
XIII
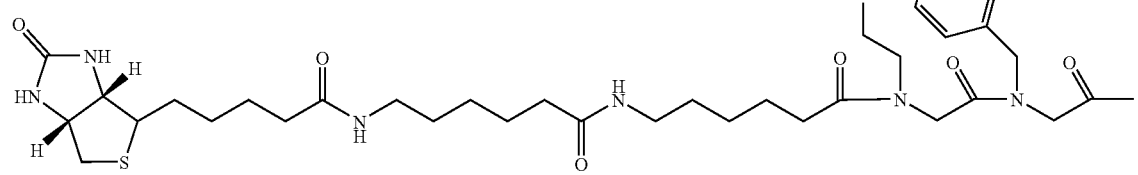

-continued
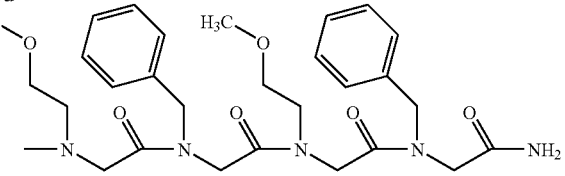
or salts thereof.
13. A peptoid reagent selected from:
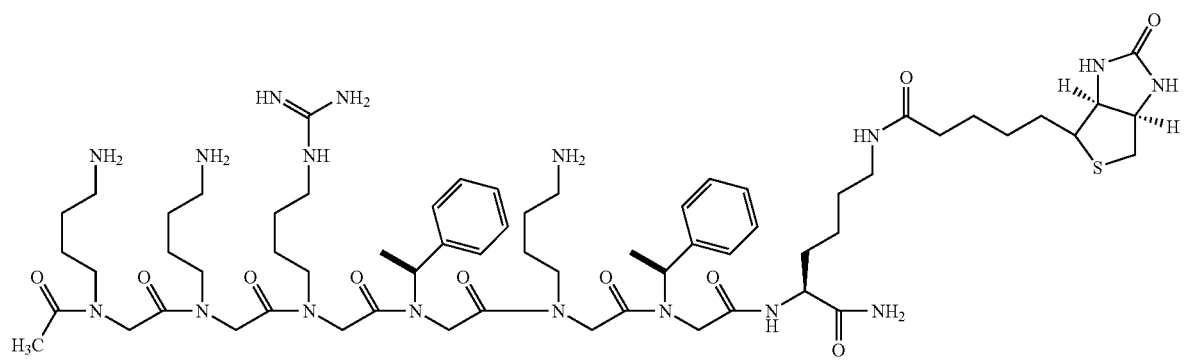
II
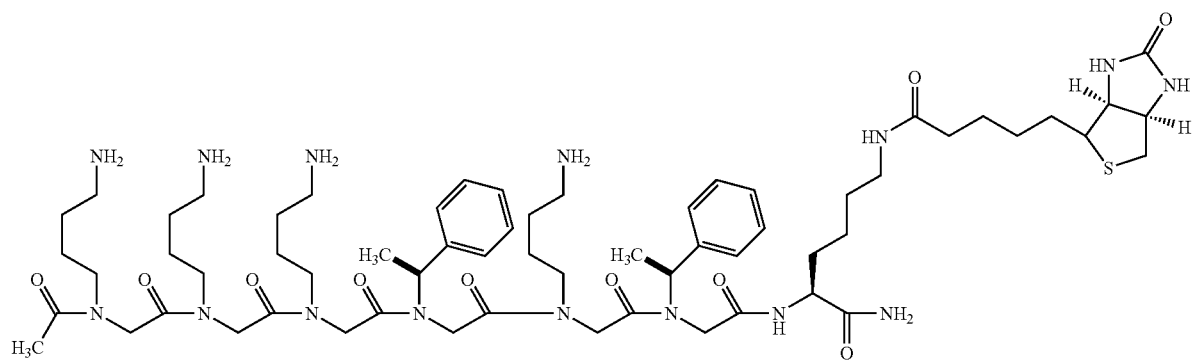
IX
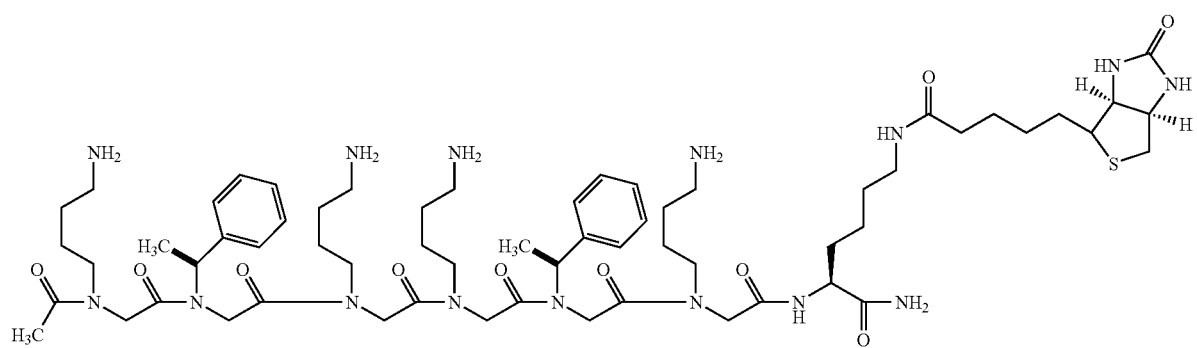
X -continued

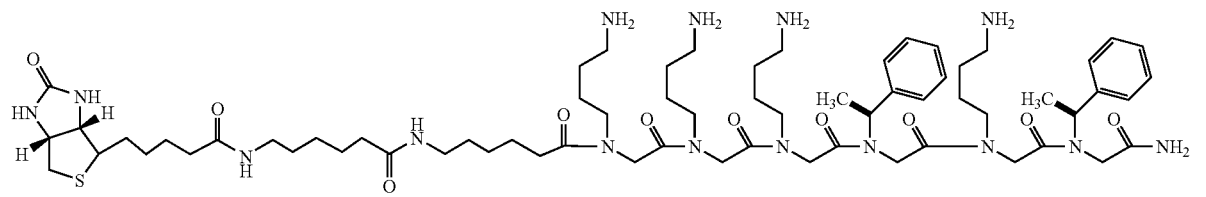
XIa

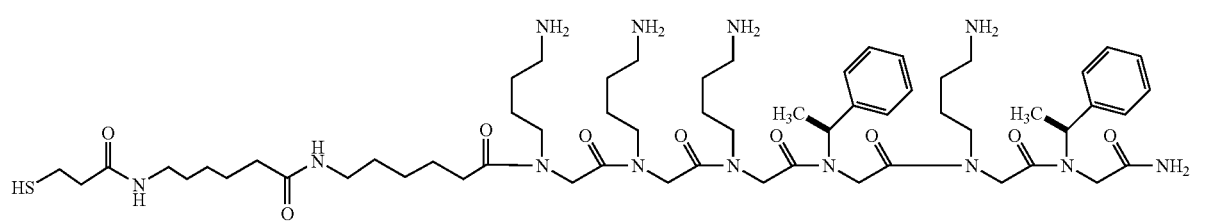
XIb

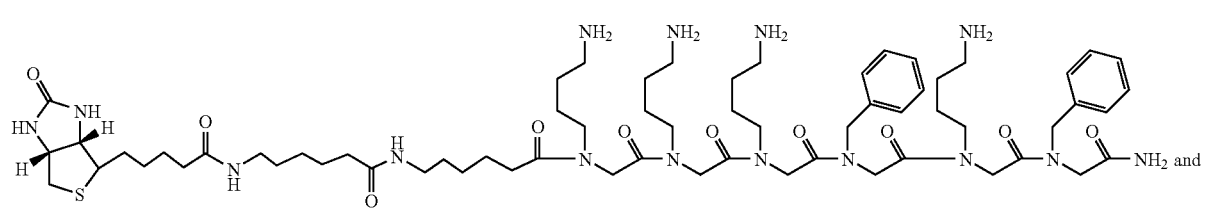
XIIa

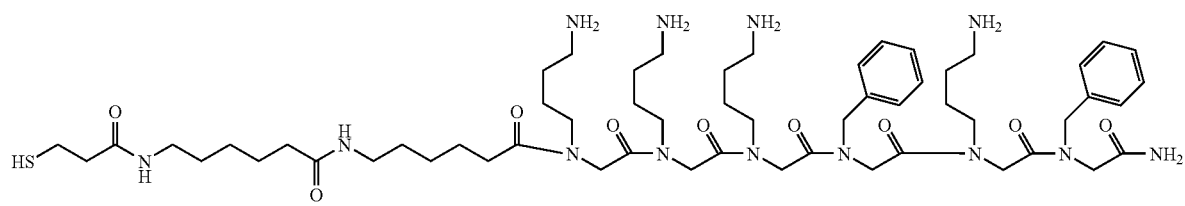
XIIb or salts thereof.

14. A complex comprising the peptoid reagent of claim 1 and a pathogenic prion.

15. A composition comprising the peptoid reagent of claim 1 attached to a solid support.

16. A composition comprising the peptoid reagent of claim 1 and a sample.

17. The composition of claim 16 wherein the sample is a biological sample.

18. A method for detecting the presence of a pathogenic prion in a sample, comprising contacting said sample with a first peptoid reagent according to claim 1 under conditions that allow binding of said peptoid reagent to said pathogenic prion, if present, to form a complex, and detecting the formation of said complex, wherein the formation of the complex is indicative of the presence of said pathogenic prion.

19. A method for detecting the presence of a pathogenic prion in a sample, comprising contacting said sample with a first peptoid reagent according to claim 1 under conditions that allow binding of said first peptoid reagent to said pathogenic prion, if present, to form a first complex, contacting said first complex with a second peptoid reagent of the invention, optionally detectably labeled, under conditions that allow binding of said second peptoid reagent to said pathogenic prion of said first complex to form a second complex, and detecting formation of said second complex, wherein the formation of said second complex is indicative of the presence of the pathogenic prion.

20. A method for detecting the presence of a pathogenic prion in a sample, comprising contacting said sample with a first peptoid reagent according to claim 1 under conditions that allow binding of said first peptoid reagent to said pathogenic prion, if present, to form a first complex, removing unbound sample from said first complex, contacting said first complex with a second peptoid reagent of the invention, optionally detectably labeled, under conditions that allow binding of said second peptoid reagent to said pathogenic prion of said first complex to form a second complex, and detecting formation of said second complex, wherein the formation of said second complex is indicative of the presence of the pathogenic prion.

21. A method for detecting the presence of a pathogenic prion in a sample, comprising contacting the sample with a first peptoid reagent according to claim 1 under conditions that allow binding of said first peptoid reagent to said pathogenic prion, if present, to form a first complex, removing unbound sample from said first complex, dissociating said pathogenic prion from said first complex thereby providing dissociated pathogenic prion, contacting said dissociated pathogenic prion with a second peptoid reagent according to claim 1, optionally detectably labeled, under conditions that allow binding of said second peptoid reagent to said dissociated pathogenic prion to form a second complex, and detecting the formation of said second complex, wherein the formation of said second complex is indicative of the presence of the pathogenic prion.

22. A method for detecting the presence of a pathogenic prion in a sample, comprising contacting said sample with a first peptoid reagent according to claim 1 under conditions that allow binding of said first peptoid reagent to said pathogenic prion, if present, to form a first complex, contacting said first complex with a prion-binding reagent, optionally detectably labeled, under conditions that allow binding of said prion-binding reagent to said pathogenic prion of said first complex to form a second complex, and detecting formation of said second complex, wherein the formation of said second complex is indicative of the presence of the pathogenic prion.

23. The method of claim 22 wherein said prion-binding reagent comprises an anti-prion antibody.

24. A method for detecting the presence of a pathogenic prion in a sample, comprising contacting said sample with a first peptoid reagent according to claim 1 under conditions that allow binding of said first peptoid reagent to said pathogenic prion, if present, to form a first complex, removing unbound sample from said first complex, contacting said first complex with a prion-binding reagent, optionally detectably labeled, under conditions that allow binding of said prion-binding reagent to said pathogenic prion of said first complex to form a second complex, and detecting formation of said second complex, wherein the formation of the second complex is indicative of the presence of the pathogenic prion.

25. The method of claim 24 wherein said prion-binding reagent comprises an anti-prion antibody.

26. A method for detecting the presence of a pathogenic prion in a sample, comprising contacting said sample with a first peptoid reagent according to claim 1 under conditions that allow binding of said first peptoid reagent to said pathogenic prion, if present, to form a first complex, removing unbound sample from said first complex, dissociating said pathogenic prion from said first complex thereby providing dissociated pathogenic prion, contacting said dissociated pathogenic prion with a prion-binding reagent, optionally detectably labeled, under conditions that allow binding of said prion-binding reagent to said dissociated pathogenic prion to form a second complex, and detecting the formation of said second complex, wherein the formation of said second complex is indicative of the presence of said pathogenic prion.

27. The method of claim 26 wherein said prion-binding reagent comprises an anti-prion antibody.

28. A method for detecting the presence of a pathogenic prion in a sample, comprising contacting said sample with a first peptoid reagent according to claim 1 under conditions that allow binding of said first peptoid reagent to said pathogenic prion, if present, to form a first complex, removing unbound sample from said first complex, dissociating said pathogenic prion from said first complex thereby providing dissociated pathogenic prion, contacting said dissociated pathogenic prion with a prion-binding reagent under conditions that allow binding of said prion-binding reagent to said dissociated pathogenic prion to form a second complex, and detecting the formation of said second complex using a second prion-binding reagent, optionally detectably labeled, wherein the formation of said second complex is indicative of the presence of the pathogenic prion.

29. The method of claim 28 wherein said prion-binding reagent comprises an anti-prion antibody.

30. A method for detecting the presence of a pathogenic prion in a sample, comprising contacting said sample with a prion-binding reagent under conditions that allow binding of said prion-binding reagent to the pathogenic prion, if present, to form a first complex, removing unbound sample from said first complex, contacting said first complex with a peptoid reagent of the invention, optionally detectably labeled, under conditions that allow binding of said peptoid reagent to said pathogenic prion of said first complex to form a second complex, and detecting the formation of said second complex, wherein the formation of said second complex is indicative of the presence of said pathogenic prion.

31. The method of claim 30 wherein said prion-binding reagent comprises an anti-prion antibody.

32. A method for detecting the presence of a pathogenic prion in a sample, comprising combining a solid support with a detectably labeled ligand, wherein said solid support comprises a peptoid reagent according to claim 1, under conditions that allow binding of said detectably labeled ligand to said peptoid reagent, wherein said peptoid reagent of said solid support has a weaker binding affinity for said ligand than for said pathogenic prion, to form a first complex, combining said sample with said first complex under conditions that allow binding of said pathogenic prion, if present in the sample, to said peptoid reagent of said first complex, thereby replacing said detectably labeled ligand of said first complex and forming a second complex comprising said peptoid reagent and said pathogenic prion, and detecting the formation of said second complex, wherein the formation of said second complex is indicative of the presence of said pathogenic prion.

33. A method for detecting the presence of a pathogenic prion in a sample, comprising: contacting said sample with a first peptoid reagent according to claim 1 under conditions that allow binding of said first peptoid reagent to said pathogenic prion, if present, to form a complex, removing unbound sample from said complex, dissociating said pathogenic prion from said complex thereby providing dissociated pathogenic prion, contacting said dissociated pathogenic prion with a second solid support under conditions that allow said dissociated pathogenic prion to adhere to said second solid support; and detecting the adhered dissociated pathogenic prion using a prion-binding reagent, optionally detectably labeled, wherein binding of said prion-binding reagent indicates the presence of said pathogenic prion.

34. The method of claim 33 wherein said dissociating is carried out by exposing said complex to high pH or low pH.

35. The method of claim 34 further comprising the step of neutralizing said high pH or said low pH after said dissociating.

36. The method of claim 33 wherein said dissociated pathogenic prion is denatured.

37. The method of claim 34 wherein said prion-binding reagent comprises an anti-prion antibody.

38. A method for detecting the presence of a pathogenic prion in a sample, comprising: contacting said sample with a first peptoid reagent according to claim 1 under conditions that allow binding of said first peptoid reagent to said pathogenic prion, if present, to form a first complex, removing unbound sample from said first complex, dissociating said pathogenic prion from said first complex thereby providing dissociated pathogenic prion, contacting said dissociated pathogenic prion with a second solid support, wherein said second solid support comprises a first anti-prion antibody, under conditions that allow said dissociated pathogenic prion to bind to said first anti-prion antibody to form a second complex; and detecting said dissociated pathogenic prion of said second complex with a second anti-prion antibody, optionally detectably labeled, wherein binding of said second-anti-prion antibody indicates the presence of said pathogenic prion.

39. The method of claim 38 wherein said dissociating is carried out by exposing said first complex to high pH or low pH.

40. The method of claim 39 further comprising the step of neutralizing said high pH or said low pH after said dissociating.

41. The method of claim 38 wherein said dissociated pathogenic prion is denatured.

42. The method of claim 38 wherein said first prion-binding reagent comprises an anti-prion antibody.

43. The method of claim 38 wherein second prion-binding reagent comprises an anti-prion antibody.

44. A method for isolating a pathogenic prion from a sample comprising:
   (a) contacting a solid support comprising a peptoid reagent of claim 1 with said sample under conditions that allow binding of said pathogenic prion, if present in the sample, to said peptoid reagent to form a complex; and
   (b) removing unbound sample from said complex, thereby providing isolated pathogenic prion.

45. A method for reducing the amount of the pathogenic prion in a sample comprising:
   (a) contacting solid support comprising a peptoid reagent of claim 1 with said sample under conditions that allow binding of said pathogenic prion, if present in said sample, to said peptoid reagent of said solid support to form a complex; and
   (b) separating unbound sample from said complex, thereby providing said sample with a reduced amount of the pathogenic prion.

46. The method of claim 45, wherein the amount of the pathogenic prion in the recovered sample is reduced below a detectable level.

47. The method of claim 45, wherein the amount of the pathogenic prion is reduced by about 95 to 100%.

48. A method of preparing a blood supply that is substantially free of a pathogenic prion comprising:
   (a) detecting the presence or absence of pathogenic prion in a plurality of blood samples, wherein said detecting involves binding of said pathogenic prion, if present, to a peptoid reagent of claim 1; and
   (b) combining said samples in which the pathogenic prion is not detected, thereby providing the blood supply that is substantially free of the pathogenic prion.

49. A method of preparing a food supply that is substantially free of a pathogenic prion comprising:
   (a) detecting the presence or absence of pathogenic prion in a plurality of food samples, wherein said detecting involves binding of said pathogenic prion, if present, to a peptoid reagent of claim 1; and
   (b) combining said samples in which the pathogenic prion is not detected, thereby providing said food supply that is substantially free of the pathogenic prion.

50. A peptoid reagent comprising a sequence selected from SEQ ID NO: 229, 230, 231, 232, 233, 234, 235, 236, 237, 238, 239, 240, or 241.

* * * * *

SEQUENCE LISTING

```
<160> NUMBER OF SEQ ID NOS: 241

<210> SEQ ID NO 1
<211> LENGTH: 253
<212> TYPE: PRT
<213> ORGANISM: Homo sapiens

<400> SEQUENCE: 1

Met Ala Asn Leu Gly Cys Trp Met Leu Val Leu Phe Val Ala Thr Trp
 1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
               100                 105                 110

Ala Gly Ala Ala Ala Ala Gly Ala Val Val Gly Gly Leu Gly Gly Tyr
           115                 120                 125

Met Leu Gly Ser Ala Met Ser Arg Pro Ile Ile His Phe Gly Ser Asp
       130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
               165                 170                 175

His Asp Cys Val Asn Ile Thr Ile Lys Gln His Thr Val Thr Thr Thr
           180                 185                 190

Thr Lys Gly Glu Asn Phe Thr Glu Thr Asp Val Lys Met Met Glu Arg
       195                 200                 205

Val Val Glu Gln Met Cys Ile Thr Gln Tyr Glu Arg Glu Ser Gln Ala
   210                 215                 220

Tyr Tyr Gln Arg Gly Ser Ser Met Val Leu Phe Ser Ser Pro Pro Val
```

```
                225                 230                 235                 240
Ile Leu Leu Ile Ser Phe Leu Ile Phe Leu Ile Val Gly
                245                 250

<210> SEQ ID NO 2
<211> LENGTH: 254
<212> TYPE: PRT
<213> ORGANISM: Mus musculus

<400> SEQUENCE: 2

Met Ala Asn Leu Gly Tyr Trp Leu Leu Ala Leu Phe Val Thr Met Trp
  1               5                  10                  15

Thr Asp Val Gly Leu Cys Lys Lys Arg Pro Lys Pro Gly Gly Trp Asn
                 20                  25                  30

Thr Gly Gly Ser Arg Tyr Pro Gly Gln Gly Ser Pro Gly Gly Asn Arg
             35                  40                  45

Tyr Pro Pro Gln Gly Gly Thr Trp Gly Gln Pro His Gly Gly Gly Trp
         50                  55                  60

Gly Gln Pro His Gly Gly Ser Trp Gly Gln Pro His Gly Gly Ser Trp
 65                  70                  75                  80

Gly Gln Pro His Gly Gly Gly Trp Gly Gln Gly Gly Thr His Asn
                 85                  90                  95

Gln Trp Asn Lys Pro Ser Lys Pro Lys Thr Asn Leu Lys His Val Ala
                100                 105                 110

Gly Ala Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
        130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 3
<211> LENGTH: 253
<212> TYPE: PRT
<213> ORGANISM: Homo sapiens

<400> SEQUENCE: 3

Met Ala Asn Leu Gly Cys Trp Met Leu Val Leu Phe Val Ala Thr Trp
  1               5                  10                  15

Ser Asp Leu Gly Leu Cys Lys Lys Arg Pro Lys Pro Gly Gly Trp Asn
                 20                  25                  30

Thr Gly Gly Ser Arg Tyr Pro Gly Gln Gly Ser Pro Gly Gly Asn Arg
             35                  40                  45

Tyr Pro Pro Gln Gly Gly Gly Gly Trp Gly Gln Pro His Gly Gly Gly
```

-continued

```
            50                  55                  60
Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 4
<211> LENGTH: 254
<212> TYPE: PRT
<213> ORGANISM: Mesocricetus auratus

<400> SEQUENCE: 4

Met Ala Asn Leu Ser Tyr Trp Leu Leu Ala Leu Phe Val Ala Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Thr Trp Gly Gln Pro His Gly Gly Gly
 50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Asn Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175
```

```
His Asp Cys Val Asn Ile Thr Ile Lys Gln His Thr Val Thr Thr Thr
                180                 185                 190

Thr Lys Gly Glu Asn Phe Thr Glu Thr Asp Ile Lys Ile Met Glu Arg
        195                 200                 205

Val Val Glu Gln Met Cys Thr Thr Gln Tyr Gln Lys Glu Ser Gln Ala
    210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Met Val Gly
                245                 250

<210> SEQ ID NO 5
<211> LENGTH: 265
<212> TYPE: PRT
<213> ORGANISM: Bos taurus
<220> FEATURE:
<221> NAME/KEY: VARIANT
<222> LOCATION: 46, 155
<223> OTHER INFORMATION: Xaa = Any Amino Acid

<400> SEQUENCE: 5

Met Val Lys Ser His Ile Gly Ser Trp Ile Leu Val Leu Phe Val Ala
 1               5                  10                  15

Met Trp Ser Asp Val Gly Leu Cys Lys Lys Arg Pro Lys Pro Gly Gly
                20                  25                  30

Gly Trp Asn Thr Gly Gly Ser Arg Tyr Pro Gly Gln Gly Xaa Pro Gly
            35                  40                  45

Gly Asn Thr Arg Tyr Pro Pro Gln Gly Gly Gly Trp Gly Gln Pro
    50                  55                  60

His Gly Gly Gly Trp Gly Gln Pro His Gly Gly Gly Trp Gly Gln Pro
65                  70                  75                  80

His Gly Gly Gly Trp Gly Gln Pro His Gly Gly Gly Trp Gly Gln Pro
                85                  90                  95

His Gly Gly Gly Gly Trp Gly Gln Gly Gly Thr His Gly Gln Trp Asn
                100                 105                 110

Lys Pro Ser Lys Pro Lys Thr Asn Met Lys His Val Ala Gly Ala Ala
            115                 120                 125

Ala Ala Gly Ala Val Val Gly Gly Leu Gly Gly Tyr Met Leu Gly Ser
    130                 135                 140

Ala Met Ser Arg Pro Leu Ile His Phe Gly Xaa Asp Tyr Glu Asp Arg
145                 150                 155                 160

Tyr Tyr Arg Glu Asn Met His Arg Tyr Pro Asn Gln Val Tyr Tyr Arg
                165                 170                 175

Pro Val Asp Gln Tyr Ser Asn Gln Asn Asn Phe Val His Asp Cys Val
            180                 185                 190

Asn Ile Thr Val Lys Glu His Thr Val Thr Thr Thr Thr Lys Gly Glu
    195                 200                 205

Asn Phe Thr Glu Thr Asp Ile Lys Met Met Glu Arg Val Val Glu Gln
210                 215                 220

Met Cys Ile Thr Gln Tyr Gln Arg Glu Ser Gln Ala Tyr Tyr Gln Arg
225                 230                 235                 240

Gly Ala Ser Val Ile Leu Phe Ser Ser Pro Pro Val Ile Leu Leu Ile
                245                 250                 255

Ser Phe Leu Ile Phe Leu Ile Val Gly
                260                 265
```

```
<210> SEQ ID NO 6
<211> LENGTH: 256
<212> TYPE: PRT
<213> ORGANISM: Ovis aries

<400> SEQUENCE: 6

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Arg Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 7
<211> LENGTH: 254
<212> TYPE: PRT
<213> ORGANISM: Mus musculus

<400> SEQUENCE: 7

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Gly Thr His Asn
```

-continued

```
                85                  90                  95
Gln Trp Asn Lys Pro Ser Lys Pro Lys Thr Asn Leu Lys His Val Ala
            100                 105                 110
Gly Ala Ala Ala Gly Ala Val Val Gly Gly Leu Gly Gly Tyr Met
        115                 120                 125
Leu Gly Ser Ala Met Ser Arg Pro Met Ile His Phe Gly Asn Asp Trp
    130                 135                 140
Glu Asp Arg Tyr Tyr Arg Glu Asn Met Tyr Arg Tyr Pro Asn Gln Val
145                 150                 155                 160
Tyr Tyr Arg Pro Val Asp Gln Tyr Ser Asn Gln Asn Asn Phe Val His
                165                 170                 175
Asp Cys Val Asn Ile Thr Ile Lys Gln His Thr Val Thr Thr Thr Thr
            180                 185                 190
Lys Gly Glu Asn Phe Thr Glu Thr Asp Val Lys Met Met Glu Arg Val
        195                 200                 205
Val Glu Gln Met Cys Val Thr Gln Tyr Gln Lys Glu Ser Gln Ala Tyr
    210                 215                 220
Tyr Asp Gly Arg Arg Ser Ser Ser Thr Val Leu Phe Ser Ser Pro Pro
225                 230                 235                 240
Val Ile Leu Leu Ile Ser Phe Leu Ile Phe Leu Ile Val Gly
                245                 250

<210> SEQ ID NO 8
<211> LENGTH: 256
<212> TYPE: PRT
<213> ORGANISM: Cervus elaphus

<400> SEQUENCE: 8

Met Val Lys Ser His Ile Gly Ser Trp Ile Leu Val Leu Phe Val Ala
  1               5                  10                  15
Met Trp Ser Asp Val Gly Leu Cys Lys Lys Arg Pro Lys Pro Gly Gly
            20                  25                  30
Gly Trp Asn Thr Gly Gly Ser Arg Tyr Pro Gly Gln Gly Ser Pro Gly
        35                  40                  45
Gly Asn Arg Tyr Pro Pro Gln Gly Gly Gly Trp Gly Gln Pro His
    50                  55                  60
Gly Gly Gly Trp Gly Gln Pro His Gly Gly Gly Trp Gly Gln Pro His
65                  70                  75                  80
Gly Gly Gly Trp Gly Gln Pro His Gly Gly Gly Trp Gly Gln Gly
                85                  90                  95
Gly Thr His Ser Gln Trp Asn Lys Pro Ser Lys Pro Lys Thr Asn Met
            100                 105                 110
Lys His Val Ala Gly Ala Ala Ala Gly Ala Val Val Gly Gly Leu
        115                 120                 125
Gly Gly Tyr Met Leu Gly Ser Ala Met Ser Arg Pro Leu Ile His Phe
    130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Gln Tyr Asn Asn Gln Asn
                165                 170                 175
Thr Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Met
        195                 200                 205
```

```
Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 9
<211> LENGTH: 256
<212> TYPE: PRT
<213> ORGANISM: Dama dama

<400> SEQUENCE: 9

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
                20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
                100                 105                 110

Lys His Val Ala Gly Ala Ala Ala Gly Ala Val Val Gly Gly Leu
            115                 120                 125

Gly Gly Tyr Met Leu Gly Ser Ala Met Asn Arg Pro Leu Ile His Phe
        130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 10
<211> LENGTH: 256
<212> TYPE: PRT
<213> ORGANISM: Odocoileus hemionus

<400> SEQUENCE: 10

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
                20                  25                  30
```

```
Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
        130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
        210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 11
<211> LENGTH: 256
<212> TYPE: PRT
<213> ORGANISM: Odocoileus virginianus

<400> SEQUENCE: 11

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
        130                 135                 140

Gly Asn Asp Tyr Glu Asp Arg Tyr Tyr Arg Glu Asn Met Tyr Arg Tyr
145                 150                 155                 160
```

```
Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 12
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 12

Lys Lys Arg Pro Lys
1               5

<210> SEQ ID NO 13
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 13

Met Ala Asn Leu Gly Cys Trp Met Leu Val Leu Phe Val Ala Thr Trp
1               5                   10                  15

Ser Asp Leu Gly Leu Cys
            20

<210> SEQ ID NO 14
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 14

Gly Gly Gly Gln Trp Asn Lys Pro Ser Lys Pro Lys Thr Asn
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 15

Gln Trp Asn Lys Pro Ser Lys Pro Lys Thr Asn Met Lys His Val
1               5                   10                  15

<210> SEQ ID NO 16
<211> LENGTH: 28
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: VARIANT
<222> LOCATION: 5
<223> OTHER INFORMATION: Xaa = Asn or Thr
<220> FEATURE:
<221> NAME/KEY: VARIANT
<222> LOCATION: 15
<223> OTHER INFORMATION: Xaa = Ile or Val
<220> FEATURE:
<221> NAME/KEY: VARIANT
<222> LOCATION: 17
<223> OTHER INFORMATION: Xaa = Gln or Glu

<400> SEQUENCE: 16

Asn Gln Asn Asn Xaa Phe Val His Asp Cys Val Asn Ile Thr Xaa Lys
1               5                   10                  15

Xaa His Thr Val Thr Thr Thr Thr Lys Gly Glu Asn
            20                  25

<210> SEQ ID NO 17
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 17

Thr Thr Lys Gly Glu Asn Phe Thr Glu Thr Asp
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 18

Gly Glu Asn Phe Thr Glu Thr Asp
1               5

<210> SEQ ID NO 19
<211> LENGTH: 38
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = Val or Ile
<220> FEATURE:
<221> NAME/KEY: VARIANT
<222> LOCATION: 11
<223> OTHER INFORMATION: Xaa = Met or Ile
<220> FEATURE:
<221> NAME/KEY: VARIANT
<222> LOCATION: 21
<223> OTHER INFORMATION: Xaa = Ile or Val
<220> FEATURE:
<221> NAME/KEY: VARIANT
<222> LOCATION: 25
<223> OTHER INFORMATION: Xaa = Glu or Gln
<220> FEATURE:
<221> NAME/KEY: VARIANT
<222> LOCATION: 32
<223> OTHER INFORMATION: Xaa = Gln or Asp
<220> FEATURE:
<221> NAME/KEY: VARIANT
<222> LOCATION: 36
```

<223> OTHER INFORMATION: Xaa = Gly or Ser
<220> FEATURE:
<221> NAME/KEY: VARIANT
<222> LOCATION: 37
<223> OTHER INFORMATION: Xaa = Ser or Ala

<400> SEQUENCE: 19

Gly Glu Asn Phe Thr Glu Thr Asp Xaa Lys Xaa Met Glu Arg Val Val
1               5                   10                  15

Glu Gln Met Cys Xaa Thr Gln Tyr Xaa Glu Ser Gln Ala Tyr Tyr Xaa
            20                  25                  30

Gly Arg Arg Xaa Xaa Ser
        35

<210> SEQ ID NO 20
<211> LENGTH: 63
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5
<223> OTHER INFORMATION: Xaa = Asn or Thr
<220> FEATURE:
<221> NAME/KEY: VARIANT
<222> LOCATION: 15, 46
<223> OTHER INFORMATION: Xaa = Ile or Val
<220> FEATURE:
<221> NAME/KEY: VARIANT
<222> LOCATION: 17
<223> OTHER INFORMATION: Xaa = Gln or Glu
<220> FEATURE:
<221> NAME/KEY: VARIANT
<222> LOCATION: 34
<223> OTHER INFORMATION: Xaa = Val or Ile
<220> FEATURE:
<221> NAME/KEY: VARIANT
<222> LOCATION: 36
<223> OTHER INFORMATION: Xaa = Met or Ile
<220> FEATURE:
<221> NAME/KEY: VARIANT
<222> LOCATION: 50
<223> OTHER INFORMATION: Xaa = Glu or Gln
<220> FEATURE:
<221> NAME/KEY: VARIANT
<222> LOCATION: 57
<223> OTHER INFORMATION: Xaa = Gln or Asp
<220> FEATURE:
<221> NAME/KEY: VARIANT
<222> LOCATION: 61
<223> OTHER INFORMATION: Xaa = Gly or Ser
<220> FEATURE:
<221> NAME/KEY: VARIANT
<222> LOCATION: 62
<223> OTHER INFORMATION: Xaa = Ser or Ala

<400> SEQUENCE: 20

Asn Gln Asn Asn Xaa Phe Val His Asp Cys Val Asn Ile Thr Xaa Lys
1               5                   10                  15

Xaa His Thr Val Thr Thr Thr Thr Lys Gly Glu Asn Phe Thr Glu Thr
            20                  25                  30

Asp Xaa Lys Xaa Met Glu Arg Val Val Glu Gln Met Cys Xaa Thr Gln Tyr
        35                  40                  45

Xaa Glu Ser Gln Ala Tyr Tyr Xaa Gly Arg Arg Xaa Xaa Ser
50                  55                  60

<210> SEQ ID NO 21
<211> LENGTH: 22
<212> TYPE: PRT

```
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Val, Thr or Met
<220> FEATURE:
<221> NAME/KEY: VARIANT
<222> LOCATION: 2
<223> OTHER INFORMATION: Xaa = Val or Ile
<220> FEATURE:
<221> NAME/KEY: VARIANT
<222> LOCATION: 20
<223> OTHER INFORMATION: Xaa = Ile or Met

<400> SEQUENCE: 21

Xaa Xaa Leu Phe Ser Ser Pro Pro Val Ile Leu Leu Ile Ser Phe Leu
 1               5                  10                  15

Ile Phe Leu Xaa Val Gly
            20

<210> SEQ ID NO 22
<211> LENGTH: 36
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Asn or Ser
<220> FEATURE:
<221> NAME/KEY: VARIANT
<222> LOCATION: 4
<223> OTHER INFORMATION: Xaa = Trp 0r Tyr
<220> FEATURE:
<221> NAME/KEY: VARIANT
<222> LOCATION: 14
<223> OTHER INFORMATION: Xaa = His or Tyr
<220> FEATURE:
<221> NAME/KEY: VARIANT
<222> LOCATION: 25
<223> OTHER INFORMATION: Xaa = Met or Val
<220> FEATURE:
<221> NAME/KEY: VARIANT
<222> LOCATION: 27
<223> OTHER INFORMATION: Xaa = Gln, Glu or Arg
<220> FEATURE:
<221> NAME/KEY: VARIANT
<222> LOCATION: 29
<223> OTHER INFORMATION: Xaa = Ser or Asn
<220> FEATURE:
<221> NAME/KEY: VARIANT
<222> LOCATION: 33
<223> OTHER INFORMATION: Xaa = Asn or Thr

<400> SEQUENCE: 22

Gly Xaa Asp Xaa Glu Asp Arg Tyr Tyr Arg Glu Asn Met Xaa Arg Tyr
 1               5                  10                  15

Pro Asn Gln Val Tyr Tyr Arg Pro Xaa Asp Xaa Tyr Xaa Asn Gln Asn
                20                  25                  30

Xaa Phe Val His
        35

<210> SEQ ID NO 23
<211> LENGTH: 22
<212> TYPE: PRT
<213> ORGANISM: Artificial Sequence
<220> FEATURE:
<223> OTHER INFORMATION: Synthetically generated peptide
<220> FEATURE:
```

```
<221> NAME/KEY: VARIANT
<222> LOCATION: 2
<223> OTHER INFORMATION: Xaa = Asn or Thr
<220> FEATURE:
<221> NAME/KEY: VARIANT
<222> LOCATION: 12
<223> OTHER INFORMATION: Xaa = Ile or Val
<220> FEATURE:
<221> NAME/KEY: VARIANT
<222> LOCATION: 14
<223> OTHER INFORMATION: Xaa = Gln or Glu

<400> SEQUENCE: 23

Asn Xaa Phe Val His Asp Cys Val Asn Ile Thr Xaa Lys Xaa His Thr
 1               5                  10                  15

Val Thr Thr Thr Thr Lys
            20

<210> SEQ ID NO 24
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 24

Val Tyr Tyr Arg
 1

<210> SEQ ID NO 25
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Met or Val
<220> FEATURE:
<221> NAME/KEY: VARIANT
<222> LOCATION: 13
<223> OTHER INFORMATION: Xaa = Gln, Glu or Arg

<400> SEQUENCE: 25

Arg Tyr Pro Asn Gln Val Tyr Tyr Arg Pro Xaa Asp Xaa
 1               5                  10

<210> SEQ ID NO 26
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 26

Lys Lys Arg Pro Lys Pro Gly Gly Gly Trp Asn Thr Gly Gly Ser Arg
 1               5                  10                  15

Tyr Pro Gly Gln Gly Ser Pro Gly Gly Asn Arg Tyr Pro Pro Gln Gly
            20                  25                  30

Gly

<210> SEQ ID NO 27
<211> LENGTH: 25
<212> TYPE: PRT
<213> ORGANISM: Artificial Sequence
<220> FEATURE:
<223> OTHER INFORMATION: Synthetically generated peptide
```

```
<400> SEQUENCE: 27

Trp Asn Thr Gly Gly Ser Arg Tyr Pro Gly Gln Gly Ser Pro Gly Gly
 1               5                  10                  15

Asn Arg Tyr Pro Pro Gln Gly Gly Gly
            20                  25

<210> SEQ ID NO 28
<211> LENGTH: 33
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 26
<223> OTHER INFORMATION: Xaa = Gly or Thr

<400> SEQUENCE: 28

Trp Asn Thr Gly Gly Ser Arg Tyr Pro Gly Gln Gly Ser Pro Gly Gly
 1               5                  10                  15

Asn Arg Tyr Pro Pro Gln Gly Gly Gly Xaa Trp Gly Gln Pro His Gly
            20                  25                  30

Gly

<210> SEQ ID NO 29
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 29

Gly Gly Trp Gly Gln Gly Gly Thr His Ser Gln Trp Asn Lys Pro
 1               5                  10                  15

Ser Lys Pro Lys Thr Asn
            20

<210> SEQ ID NO 30
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 30

Gly Gly Thr His Ser Gln Trp Asn Lys Pro Ser Lys Pro Lys Thr Asn
 1               5                  10                  15

<210> SEQ ID NO 31
<211> LENGTH: 49
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 26
<223> OTHER INFORMATION: Xaa = Gly or Thr

<400> SEQUENCE: 31

Trp Asn Thr Gly Gly Ser Arg Tyr Pro Gly Gln Gly Ser Pro Gly Gly
 1               5                  10                  15

Asn Arg Tyr Pro Pro Gln Gly Gly Gly Xaa Trp Gly Gln Pro His
            20                  25                  30
```

-continued

```
Gly Gly Gly Trp Gly Gln Pro His Gly Gly Gly Trp Gly Gln Pro His
            35                  40                  45

Gly Gly

<210> SEQ ID NO 32
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 32

Gly Gln Pro His Gly Gly Gly Trp
 1               5

<210> SEQ ID NO 33
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 33

Arg Pro Ile Ile His Phe Gly Ser Asp Tyr Glu Asp Arg Tyr Tyr Arg
 1               5                  10                  15

Glu Asn Met His Arg
            20

<210> SEQ ID NO 34
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 34

Arg Pro Met Ile His Phe Gly Asn Asp Trp Glu Asp Arg Tyr Tyr Arg
 1               5                  10                  15

Glu Asn Met Tyr Arg
            20

<210> SEQ ID NO 35
<211> LENGTH: 38
<212> TYPE: PRT
<213> ORGANISM: Artificial Sequence
<220> FEATURE:
<223> OTHER INFORMATION: Synthetically generated peptide

<400> SEQUENCE: 35

Gly Gly Gly Gly Cys Gly Gly Gly Gly Trp Gly Gln Gly Gly Gly Thr
 1               5                  10                  15

His Asn Gln Trp Asn Lys Pro Ser Lys Pro Lys Thr Asn Leu Lys His
            20                  25                  30

Val Gly Gly Gly Gly Cys
        35

<210> SEQ ID NO 36
<211> LENGTH: 30
<212> TYPE: PRT
<213> ORGANISM: Artificial Sequence
<220> FEATURE:
<223> OTHER INFORMATION: Synthetically generated peptide

<400> SEQUENCE: 36
```

```
Gly Gly Gly Gly Gly Gly Trp Gly Gln Gly Gly Gly Thr His Asn Gln
  1               5                  10                  15

Trp Asn Lys Pro Ser Lys Pro Lys Thr Asn Leu Lys His Val
             20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Synthetically generated peptide

<400> SEQUENCE: 37

Gly Gly Trp Gly Gln Gly Gly Gly Thr His Asn Gln Trp Asn Lys Pro
  1               5                  10                  15

Ser Lys Pro Lys Thr Asn Leu Lys His Val Gly Gly Gly Gly
             20                  25                  30

<210> SEQ ID NO 38
<211> LENGTH: 4
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Met or Leu
<220> FEATURE:
<221> NAME/KEY: VARIANT
<222> LOCATION: 4
<223> OTHER INFORMATION: Xaa = Met or Val

<400> SEQUENCE: 38

Xaa Lys His Xaa
  1

<210> SEQ ID NO 39
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 6
<223> OTHER INFORMATION: Xaa = Met or Leu
<220> FEATURE:
<221> NAME/KEY: VARIANT
<222> LOCATION: 9
<223> OTHER INFORMATION: Xaa = Met or Val

<400> SEQUENCE: 39

Lys Pro Lys Thr Asn Xaa Lys His Xaa
  1               5

<210> SEQ ID NO 40
<211> LENGTH: 34
<212> TYPE: PRT
<213> ORGANISM: Artificial Sequence
<220> FEATURE:
<223> OTHER INFORMATION: Synthetically generated peptide

<400> SEQUENCE: 40

Cys Gly Gly Gly Gly Trp Gly Gln Gly Gly Gly Thr His Asn Gln Trp
  1               5                  10                  15

Asn Lys Pro Ser Lys Pro Lys Thr Asn Leu Lys His Val Gly Gly Gly
```

```
                    20                  25                  30
Gly Cys

<210> SEQ ID NO 41
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 41

Ser Arg Pro Ile Ile His Phe Gly Ser Asp Tyr Glu Asp Arg Tyr Tyr
1               5                   10                  15

Arg Glu Asn Met His Arg Tyr Pro Asn
            20                  25

<210> SEQ ID NO 42
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 42

Pro Met Ile His Phe Gly Asn Asp Trp Glu Asp Arg Tyr Tyr Arg Glu
1               5                   10                  15

Asn Met Tyr Arg Pro Val Asp
            20

<210> SEQ ID NO 43
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 43

Ala Gly Ala Ala Ala Ala Gly Ala Val Val Gly Gly Leu Gly Gly Tyr
1               5                   10                  15

Met Leu Gly Ser Ala Met
            20

<210> SEQ ID NO 44
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 44

Arg Pro Met Ile His Phe Gly Asn Asp Trp Glu Asp Arg Tyr Tyr Arg
1               5                   10                  15

Glu Asn Met Tyr Arg Gly Gly Gly
            20

<210> SEQ ID NO 45
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 45

Gly Gly Gly Arg Pro Met Ile His Phe Gly Asn Asp Trp Glu Asp Arg
```

-continued

```
                1               5                  10                  15
Tyr Tyr Arg Glu Asn Met Tyr Arg Gly Gly
                20                  25

<210> SEQ ID NO 46
<211> LENGTH: 31
<212> TYPE: PRT
<213> ORGANISM: Artificial Sequence
<220> FEATURE:
<223> OTHER INFORMATION: Synthetically generated peptide

<400> SEQUENCE: 46

Gly Gly Cys Gly Gly Gly Arg Pro Met Ile His Phe Gly Asn Asp Trp
1               5                  10                  15

Glu Asp Arg Tyr Tyr Arg Glu Asn Met Tyr Arg Gly Gly Gly Cys
                20                  25                  30

<210> SEQ ID NO 47
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 47

Ala Gly Ala Ala Ala Ala Gly Ala Val Val Gly Gly Leu Gly Gly
1               5                  10                  15

<210> SEQ ID NO 48
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 48

Gly Gly Leu Gly Gly
1               5

<210> SEQ ID NO 49
<211> LENGTH: 3
<212> TYPE: PRT
<213> ORGANISM: Artificial Sequence
<220> FEATURE:
<223> OTHER INFORMATION: Synthetically generated peptide

<400> SEQUENCE: 49

Leu Gly Ser
1

<210> SEQ ID NO 50
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 50

Gln Trp Asn Lys Pro Ser Lys Pro Lys Thr Asn Gly Gly Gly
1               5                  10

<210> SEQ ID NO 51
<211> LENGTH: 25
<212> TYPE: PRT
<213> ORGANISM: Artificial Sequence
<220> FEATURE:
```

<223> OTHER INFORMATION: Synthetically generated peptide

<400> SEQUENCE: 51

Gln Trp Asn Lys Pro Ser Lys Pro Lys Thr Asn Gly Gly Gly Gln Trp
1               5                   10                  15

Asn Lys Pro Ser Lys Pro Lys Thr Asn
            20                  25

<210> SEQ ID NO 52
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 52

Gln Trp Asn Lys Pro Ser Lys Pro Lys Thr Asn Leu Lys His Val Gly
1               5                   10                  15

Gly Gly

<210> SEQ ID NO 53
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 53

Gly Gly Trp Gly Gln Gly Gly Thr His Asn Gln Trp Asn Lys Pro
1               5                   10                  15

Ser Lys Pro Lys Thr Asn
            20

<210> SEQ ID NO 54
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 54

Gly Gly Thr His Asn Gln Trp Asn Lys Pro Ser Lys Pro Lys Thr Asn
1               5                   10                  15

<210> SEQ ID NO 55
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 55

Gly Gly Gly Ala Gly Ala Ala Ala Gly Ala Val Val Gly Gly Leu
1               5                   10                  15

Gly Gly Tyr Met Leu Gly Ser Ala Met
            20                  25

<210> SEQ ID NO 56
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 56

```
Gly Gly Gly Ala Gly Ala Ala Ala Gly Ala Val Val Gly Gly Leu
 1               5                  10                 15

Gly Gly

<210> SEQ ID NO 57
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 57

Lys Lys Lys Ala Gly Ala Ala Ala Gly Ala Val Val Gly Gly Leu
 1               5                  10                 15

Gly Gly Tyr Met Leu Gly Ser Ala Met
            20                  25

<210> SEQ ID NO 58
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8
<223> OTHER INFORMATION: Xaa = Ser or Asn

<400> SEQUENCE: 58

Tyr Met Leu Gly Ser Ala Met Xaa Arg
 1               5

<210> SEQ ID NO 59
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ser or Asn
<220> FEATURE:
<221> NAME/KEY: VARIANT
<222> LOCATION: 4
<223> OTHER INFORMATION: Xaa = Met Ile or Leu
<220> FEATURE:
<221> NAME/KEY: VARIANT
<222> LOCATION: 5
<223> OTHER INFORMATION: Xaa = Ile or Leu

<400> SEQUENCE: 59

Xaa Arg Pro Xaa Xaa His
 1               5

<210> SEQ ID NO 60
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8
<223> OTHER INFORMATION: Xaa = Ser or Asn
<220> FEATURE:
<221> NAME/KEY: VARIANT
<222> LOCATION: 11
<223> OTHER INFORMATION: Xaa = Met, Ile or Leu
```

```
<220> FEATURE:
<221> NAME/KEY: VARIANT
<222> LOCATION: 12
<223> OTHER INFORMATION: Xaa = Ile or Leu

<400> SEQUENCE: 60

Tyr Met Leu Gly Ser Ala Met Xaa Arg Pro Xaa Xaa His
 1               5                  10

<210> SEQ ID NO 61
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8
<223> OTHER INFORMATION: Xaa = Ser or Asn
<220> FEATURE:
<221> NAME/KEY: VARIANT
<222> LOCATION: 11
<223> OTHER INFORMATION: Xaa = Met, Ile or Leu
<220> FEATURE:
<221> NAME/KEY: VARIANT
<222> LOCATION: 12
<223> OTHER INFORMATION: Xaa = Ile or Leu
<220> FEATURE:
<221> NAME/KEY: VARIANT
<222> LOCATION: 16
<223> OTHER INFORMATION: Xaa = Asn or Ser

<400> SEQUENCE: 61

Tyr Met Leu Gly Ser Ala Met Xaa Arg Pro Xaa Xaa His Phe Gly Xaa
 1               5                  10                  15

Asp

<210> SEQ ID NO 62
<211> LENGTH: 25
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Trp or Tyr
<220> FEATURE:
<221> NAME/KEY: VARIANT
<222> LOCATION: 11
<223> OTHER INFORMATION: Xaa = His or Tyr
<220> FEATURE:
<221> NAME/KEY: VARIANT
<222> LOCATION: 22
<223> OTHER INFORMATION: Xaa = Met or Val
<220> FEATURE:
<221> NAME/KEY: VARIANT
<222> LOCATION: 24
<223> OTHER INFORMATION: Xaa = Gln, Glu or Arg

<400> SEQUENCE: 62

Xaa Glu Asp Arg Tyr Tyr Arg Glu Asn Met Xaa Arg Tyr Pro Asn Gln
 1               5                  10                  15

Val Tyr Tyr Arg Pro Xaa Asp Xaa Tyr
                20                  25

<210> SEQ ID NO 63
<211> LENGTH: 30
<212> TYPE: PRT
<213> ORGANISM: Artificial Sequence
<220> FEATURE:
```

```
<223> OTHER INFORMATION: Synthetically generated peptide
<220> FEATURE:
<221> NAME/KEY: VARIANT
<222> LOCATION: 1
<223> OTHER INFORMATION: Xaa = Trp or Tyr
<220> FEATURE:
<221> NAME/KEY: VARIANT
<222> LOCATION: 11
<223> OTHER INFORMATION: Xaa = His or Tyr
<220> FEATURE:
<221> NAME/KEY: VARIANT
<222> LOCATION: 22
<223> OTHER INFORMATION: Xaa = Met or Val
<220> FEATURE:
<221> NAME/KEY: VARIANT
<222> LOCATION: 24
<223> OTHER INFORMATION: Xaa = Gln, Glu or Arg
<220> FEATURE:
<221> NAME/KEY: VARIANT
<222> LOCATION: 26
<223> OTHER INFORMATION: Xaa = Ser or Asn
<220> FEATURE:
<221> NAME/KEY: VARIANT
<222> LOCATION: 30
<223> OTHER INFORMATION: Xaa = Asn or Thr

<400> SEQUENCE: 63

Xaa Glu Asp Arg Tyr Tyr Arg Glu Asn Met Xaa Arg Tyr Pro Asn Gln
 1               5                  10                  15

Val Tyr Tyr Arg Pro Xaa Asp Xaa Tyr Xaa Asn Gln Asn Xaa
             20                  25                  30

<210> SEQ ID NO 64
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Gln, Glu or Arg
<220> FEATURE:
<221> NAME/KEY: VARIANT
<222> LOCATION: 4
<223> OTHER INFORMATION: Xaa = Ser or Asn
<220> FEATURE:
<221> NAME/KEY: VARIANT
<222> LOCATION: 8
<223> OTHER INFORMATION: Xaa = Asn or Thr

<400> SEQUENCE: 64

Asp Xaa Tyr Xaa Asn Gln Asn Xaa
 1               5

<210> SEQ ID NO 65
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 65

Lys Lys Lys Ala Gly Ala Ala Ala Ala Gly Ala Val Val Gly Gly Leu
 1               5                  10                  15

Gly Gly

<210> SEQ ID NO 66
<211> LENGTH: 24
<212> TYPE: PRT
<213> ORGANISM: Artificial Sequence
```

-continued

```
<220> FEATURE:
<223> OTHER INFORMATION: Synthetically generated peptide

<400> SEQUENCE: 66

Gly Gly Gly Lys Lys Arg Pro Lys Pro Gly Gly Trp Asn Thr Gly Gly
1               5                   10                  15

Ser Arg Tyr Pro Gly Gln Gly Ser
            20

<210> SEQ ID NO 67
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 67

Gly Gly Gly Lys Lys Arg Pro Lys Pro Gly Gly Trp Asn Thr Gly Gly
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 68

Gly Gly Gly Lys Lys Arg Pro Lys Pro Gly Gly
1               5                   10

<210> SEQ ID NO 69
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 69

Pro His Gly Gly Gly Trp Gly Gln His Gly Gly Ser Trp Gly Gln Pro
1               5                   10                  15

His Gly Gly Ser Trp Gly Gln
            20

<210> SEQ ID NO 70
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 70

Pro His Gly Gly Gly Trp Gly Gln Pro His Gly Gly Ser Trp Gly Gln
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 71

Pro His Gly Gly Gly Trp Gly Gln
1               5
```

<210> SEQ ID NO 72
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 72

Gly Gly Gly Lys Lys Arg Pro Lys Pro Gly Gly Gly Lys Lys Arg Pro
1               5                   10                  15

Lys Pro Gly Gly
            20

<210> SEQ ID NO 73
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 73

Gly Gly Gly Gly Pro Lys Arg Lys Gly Pro Lys
1               5                   10

<210> SEQ ID NO 74
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 74

Gly Gly Gly Trp Asn Thr Gly Gly Ser Arg Tyr Pro Gly Gln Gly Ser
1               5                   10                  15

<210> SEQ ID NO 75
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 75

Gly Gly Gly Trp Asn Lys Pro Ser Lys Pro Lys Thr
1               5                   10

<210> SEQ ID NO 76
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 76

Gly Gly Gly Arg Pro Met Ile His Phe Gly Asn Asp Trp Glu Asp Arg
1               5                   10                  15

Tyr Tyr Arg Glu Asn Met Tyr Arg Gly Gly Cys
            20                  25

<210> SEQ ID NO 77
<211> LENGTH: 18
<212> TYPE: PRT
<213> ORGANISM: Artificial Sequence
<220> FEATURE:
<223> OTHER INFORMATION: Synthetically generated peptide

```
<400> SEQUENCE: 77

Gln Trp Asn Lys Pro Ser Lys Pro Lys Thr Asn Leu Lys His Val Gly
 1               5                  10                  15

Gly Gly

<210> SEQ ID NO 78
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 78

Gly Gly Gly Ala Gly Ala Ala Ala Gly Ala Val Val Gly Gly Leu
 1               5                  10                  15

Gly Gly Tyr Met Leu Gly Ser Ala Met
            20                  25

<210> SEQ ID NO 79
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 79

Gly Gly Gly Asn Lys Pro Ser Lys Pro Lys
 1               5                  10

<210> SEQ ID NO 80
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 80

Gly Gly Gly Lys Pro Ser Lys Pro Lys
 1               5

<210> SEQ ID NO 81
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 81

Gly Gly Gly Lys Lys Arg Pro Lys Pro Gly Gly Gly Gln Trp Asn Lys
 1               5                  10                  15

Pro Ser Lys Pro Lys Thr Asn
            20

<210> SEQ ID NO 82
<211> LENGTH: 28
<212> TYPE: PRT
<213> ORGANISM: Artificial Sequence
<220> FEATURE:
<223> OTHER INFORMATION: Synthetically generated peptide

<400> SEQUENCE: 82

Lys Lys Lys Ala Gly Ala Ala Ala Gly Ala Val Val Gly Gly Leu
 1               5                  10                  15

Gly Gly Tyr Met Leu Gly Ser Ala Met Asp Asp Asp
```

```
            20                  25

<210> SEQ ID NO 83
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 83

Asp Asp Asp Ala Gly Ala Ala Ala Gly Ala Val Val Gly Gly Leu
 1               5                  10                  15

Gly Gly Tyr Met Leu Gly Ser Ala Met
            20                  25

<210> SEQ ID NO 84
<211> LENGTH: 28
<212> TYPE: PRT
<213> ORGANISM: Artificial Sequence
<220> FEATURE:
<223> OTHER INFORMATION: Synthetically generated peptide

<400> SEQUENCE: 84

Lys Lys Lys Ala Gly Ala Ala Ala Gly Ala Val Val Gly Gly Leu
 1               5                  10                  15

Gly Gly Tyr Met Leu Gly Ser Ala Met Lys Lys Lys
            20                  25

<210> SEQ ID NO 85
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 85

Gly Gly Gly Lys Lys Lys Lys Lys Lys Lys
 1               5                  10

<210> SEQ ID NO 86
<211> LENGTH: 28
<212> TYPE: PRT
<213> ORGANISM: Artificial Sequence
<220> FEATURE:
<223> OTHER INFORMATION: Synthetically generated peptide

<400> SEQUENCE: 86

Asp Asp Asp Ala Gly Ala Ala Ala Gly Ala Val Val Gly Gly Leu
 1               5                  10                  15

Gly Gly Tyr Met Leu Gly Ser Ala Met Asp Asp Asp
            20                  25

<210> SEQ ID NO 87
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 87

Gly Gly Gly Asn Asn Lys Gln Ser Pro Trp Pro Thr Lys Lys
 1               5                  10

<210> SEQ ID NO 88
<211> LENGTH: 21
```

```
<212> TYPE: PRT
<213> ORGANISM: Artificial Sequence
<220> FEATURE:
<223> OTHER INFORMATION: Synthetically generated peptide

<400> SEQUENCE: 88

Asp Lys Asp Lys Gly Gly Val Gly Ala Gly Ala Ala Val Ala Ala Gly
 1               5                  10                  15

Gly Asp Lys Asp Lys
            20

<210> SEQ ID NO 89
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 89

Gly Gly Gly Gln Ala Asn Lys Pro Ser Lys Pro Lys Thr Asn
 1               5                  10

<210> SEQ ID NO 90
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 90

Gly Gly Gly Gln Trp Asn Lys Ala Ser Lys Pro Lys Thr Asn
 1               5                  10

<210> SEQ ID NO 91
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 91

Gly Gly Gly Gln Trp Asn Lys Pro Ser Lys Ala Lys Thr Asn
 1               5                  10

<210> SEQ ID NO 92
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 92

Gly Gly Gly Gln Trp Asn Ala Pro Ser Lys Pro Lys Thr Asn
 1               5                  10

<210> SEQ ID NO 93
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 93

Gly Gly Gly Gln Trp Asn Lys Pro Ser Ala Pro Lys Thr Asn
 1               5                  10
```

<210> SEQ ID NO 94
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 94

Gly Gly Gly Gln Trp Asn Lys Pro Ser Lys Pro Ala Thr Asn
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 95

Gly Gly Gly Gln Trp Asn Lys Ala Ser Lys Ala Lys Thr Asn
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 96

Gly Gly Gly Lys Lys Arg Ala Lys Pro Gly Gly
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 97

Gly Gly Gly Lys Lys Arg Pro Lys Ala Gly Gly
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 98

Gly Gly Gly Lys Lys Arg Ala Lys Ala Gly Gly
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 99

Gly Gly Gly Gln Trp Asn Lys Ala Ser Lys Pro Lys Thr Asn
1               5                   10

<210> SEQ ID NO 100

-continued

```
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 100

Gly Gly Gly Gln Trp Ala Lys Pro Ser Lys Pro Lys Thr Asn
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 101

Gly Gly Gly Gln Trp Asn Lys Pro Ala Lys Pro Lys Thr Asn
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 102

Gly Gly Gly Gln Trp Asn Lys Pro Ser Lys Pro Lys Ala Asn
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 103

Gly Gly Gly Gln Trp Asn Lys Pro Ser Lys Pro Lys Thr Ala
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 104

Gly Gly Gly Ala Lys Arg Pro Lys Pro Gly Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 105

Gly Gly Gly Lys Ala Arg Pro Lys Pro Gly Gly
1               5                   10

<210> SEQ ID NO 106
<211> LENGTH: 11
```

```
<212> TYPE: PRT
<213> ORGANISM: Artificial Sequence
<220> FEATURE:
<223> OTHER INFORMATION: Synthetically generated peptide

<400> SEQUENCE: 106

Gly Gly Gly Lys Lys Ala Pro Lys Pro Gly Gly
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 107

Gly Gly Gly Lys Lys Arg Pro Ala Pro Gly Gly
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 108

Gly Gly Gly Lys Lys Ala Pro Lys Ala Gly Gly
1               5                   10

<210> SEQ ID NO 109
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 109

Gly Gly Gly Lys Lys Arg Pro Lys Pro Gly Gly Gly Trp Asn Thr Gly
1               5                   10                  15

Gly

<210> SEQ ID NO 110
<211> LENGTH: 39
<212> TYPE: PRT
<213> ORGANISM: Artificial Sequence
<220> FEATURE:
<223> OTHER INFORMATION: Synthetically generated peptide

<400> SEQUENCE: 110

Gln Trp Asn Lys Pro Ser Lys Pro Lys Thr Asn Gly Gly Gly Gln Trp
1               5                   10                  15

Asn Lys Pro Ser Lys Pro Lys Thr Asn Gly Gly Gly Gln Trp Asn Lys
            20                  25                  30

Pro Ser Lys Pro Lys Thr Asn
        35

<210> SEQ ID NO 111
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 111
```

```
Gln Trp Asn Lys Pro Ser Lys Pro Lys Thr Asn Gln Trp Asn Lys Pro
1               5                   10                  15

Ser Lys Pro Lys Thr Asn Lys
            20

<210> SEQ ID NO 112
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 112

Gly Gly Gly Lys Lys Arg Pro Lys Pro Gly Gly Trp Asn Thr Gly Gly
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 113

Gly Gly Gly Lys Lys Arg Pro Lys Pro Gly Gly Trp Asn Thr Gly Gly
1               5                   10                  15

Gly

<210> SEQ ID NO 114
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 114

Lys Lys Lys Ala Gly Ala Ala Ala Gly Ala Val Val Gly Gly Leu
1               5                   10                  15

Gly Gly

<210> SEQ ID NO 115
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 115

Asp Leu Gly Leu Cys Lys Lys Arg Pro Lys Pro Gly Gly Xaa Trp Asn
1               5                   10                  15

Thr Gly Gly

<210> SEQ ID NO 116
<211> LENGTH: 18
<212> TYPE: PRT
<213> ORGANISM: Artificial Sequence
<220> FEATURE:
<223> OTHER INFORMATION: Synthetically generated peptide
<220> FEATURE:
```

```
<221> NAME/KEY: VARIANT
<222> LOCATION: 14
<223> OTHER INFORMATION: Xaa = Any Amino Acid

<400> SEQUENCE: 116

Asp Leu Gly Leu Cys Lys Lys Arg Pro Lys Pro Gly Gly Xaa Trp Asn
1               5                   10                  15

Thr Gly

<210> SEQ ID NO 117
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 117

Asp Leu Gly Leu Cys Lys Lys Arg Pro Lys Pro Gly Gly Xaa Trp Asn
1               5                   10                  15

Thr

<210> SEQ ID NO 118
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 118

Asp Leu Gly Leu Cys Lys Lys Arg Pro Lys Pro Gly Gly Xaa Trp Asn
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14)
<223> OTHER INFORMATION: Xaa = Any Amino Acid

<400> SEQUENCE: 119

Asp Leu Gly Leu Cys Lys Lys Arg Pro Lys Pro Gly Gly Xaa Trp
1               5                   10                  15

<210> SEQ ID NO 120
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 120

Asp Leu Gly Leu Cys Lys Lys Arg Pro Lys Pro Gly Gly Xaa
```

<210> SEQ ID NO 121
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 121

Leu Gly Leu Cys Lys Lys Arg Pro Lys Pro Gly Gly Xaa Trp Asn Thr
 1               5                  10                  15

Gly

<210> SEQ ID NO 122
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 122

Leu Gly Leu Cys Lys Lys Arg Pro Lys Pro Gly Gly Xaa Trp Asn Thr
 1               5                  10                  15

<210> SEQ ID NO 123
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 123

Leu Gly Leu Cys Lys Lys Arg Pro Lys Pro Gly Gly Xaa Trp Asn
 1               5                  10                  15

<210> SEQ ID NO 124
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 124

Leu Gly Leu Cys Lys Lys Arg Pro Lys Pro Gly Gly Xaa Trp
 1               5                  10

<210> SEQ ID NO 125
<211> LENGTH: 13
<212> TYPE: PRT
<213> ORGANISM: Artificial Sequence
<220> FEATURE:
<223> OTHER INFORMATION: Synthetically generated peptide

```
<220> FEATURE:
<221> NAME/KEY: VARIANT
<222> LOCATION: 13
<223> OTHER INFORMATION: Xaa = Any Amino Acid

<400> SEQUENCE: 125

Leu Gly Leu Cys Lys Lys Arg Pro Lys Pro Gly Gly Xaa
  1               5                  10

<210> SEQ ID NO 126
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Any Amino Acid

<400> SEQUENCE: 126

Gly Leu Cys Lys Lys Arg Pro Lys Pro Gly Gly Xaa Trp Asn Thr Gly
  1               5                  10                  15

Gly

<210> SEQ ID NO 127
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Any Amino Acid

<400> SEQUENCE: 127

Gly Leu Cys Lys Lys Arg Pro Lys Pro Gly Gly Xaa Trp Asn Thr Gly
  1               5                  10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Any Amino Acid

<400> SEQUENCE: 128

Gly Leu Cys Lys Lys Arg Pro Lys Pro Gly Gly Xaa Trp Asn Thr
  1               5                  10                  15

<210> SEQ ID NO 129
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Any Amino Acid

<400> SEQUENCE: 129

Gly Leu Cys Lys Lys Arg Pro Lys Pro Gly Gly Xaa Trp Asn
  1               5                  10
```

<210> SEQ ID NO 130
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Any Amino Acid

<400> SEQUENCE: 130

Gly Leu Cys Lys Lys Arg Pro Lys Pro Gly Gly Xaa Trp
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Any Amino Acid

<400> SEQUENCE: 131

Gly Leu Cys Lys Lys Arg Pro Lys Pro Gly Gly Xaa
1               5                   10

<210> SEQ ID NO 132
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Any Amino Acid

<400> SEQUENCE: 132

Leu Cys Lys Lys Arg Pro Lys Pro Gly Gly Xaa Trp Asn Thr Gly Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Any Amino Acid

<400> SEQUENCE: 133

Leu Cys Lys Lys Arg Pro Lys Pro Gly Gly Xaa Trp Asn Thr Gly
1               5                   10                  15

<210> SEQ ID NO 134
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11)

```
<223> OTHER INFORMATION: Xaa = Any Amino Acid

<400> SEQUENCE: 134

Leu Cys Lys Lys Arg Pro Lys Pro Gly Gly Xaa Trp Asn Thr
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Any Amino Acid

<400> SEQUENCE: 135

Leu Cys Lys Lys Arg Pro Lys Pro Gly Gly Xaa Trp Asn
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Any Amino Acid

<400> SEQUENCE: 136

Leu Cys Lys Lys Arg Pro Lys Pro Gly Gly Xaa Trp
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Any Amino Acid

<400> SEQUENCE: 137

Leu Cys Lys Lys Arg Pro Lys Pro Gly Gly Xaa
1               5                   10

<210> SEQ ID NO 138
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Any Amino Acid

<400> SEQUENCE: 138

Cys Lys Lys Arg Pro Lys Pro Gly Gly Xaa Trp Asn Thr Gly Gly
1               5                   10                  15

<210> SEQ ID NO 139
<211> LENGTH: 14
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Any Amino Acid

<400> SEQUENCE: 139

Cys Lys Lys Arg Pro Lys Pro Gly Gly Xaa Trp Asn Thr Gly
 1               5                  10

<210> SEQ ID NO 140
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Any Amino Acid

<400> SEQUENCE: 140

Cys Lys Lys Arg Pro Lys Pro Gly Gly Xaa Trp Asn Thr
 1               5                  10

<210> SEQ ID NO 141
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Any Amino Acid

<400> SEQUENCE: 141

Cys Lys Lys Arg Pro Lys Pro Gly Gly Xaa Trp Asn
 1               5                  10

<210> SEQ ID NO 142
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Any Amino Acid

<400> SEQUENCE: 142

Cys Lys Lys Arg Pro Lys Pro Gly Gly Xaa Trp
 1               5                  10

<210> SEQ ID NO 143
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10<223> Xaa = Any Amino Acid

<400> SEQUENCE: 143

Cys Lys Lys Arg Pro Lys Pro Gly Gly Xaa
 1               5                  10
```

<210> SEQ ID NO 144
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = Any Amino Acid

<400> SEQUENCE: 144

Lys Lys Arg Pro Lys Pro Gly Gly Xaa Trp Asn Thr Gly Gly
 1               5                  10

<210> SEQ ID NO 145
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = Any Amino Acid

<400> SEQUENCE: 145

Lys Lys Arg Pro Lys Pro Gly Gly Xaa Trp Asn Thr Gly
 1               5                  10

<210> SEQ ID NO 146
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = Any Amino Acid

<400> SEQUENCE: 146

Lys Lys Arg Pro Lys Pro Gly Gly Xaa Trp Asn Thr
 1               5                  10

<210> SEQ ID NO 147
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = Any Amino Acid

<400> SEQUENCE: 147

Lys Lys Arg Pro Lys Pro Gly Gly Xaa Trp Asn
 1               5                  10

<210> SEQ ID NO 148
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9

```
<223> OTHER INFORMATION: Xaa = Any Amino Acid

<400> SEQUENCE: 148

Lys Lys Arg Pro Lys Pro Gly Gly Xaa Trp
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 9
<223> OTHER INFORMATION: Xaa = Any Amino Acid

<400> SEQUENCE: 149

Lys Lys Arg Pro Lys Pro Gly Gly Xaa
1               5

<210> SEQ ID NO 150
<211> LENGTH: 19
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 150

Asp Val Gly Leu Cys Lys Lys Arg Pro Lys Pro Gly Gly Xaa Trp Asn
1               5                   10                  15

Thr Gly Gly

<210> SEQ ID NO 151
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 151

Asp Val Gly Leu Cys Lys Lys Arg Pro Lys Pro Gly Gly Xaa Trp Asn
1               5                   10                  15

Thr Gly

<210> SEQ ID NO 152
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 152

Asp Val Gly Leu Cys Lys Lys Arg Pro Lys Pro Gly Gly Xaa Trp Asn
1               5                   10                  15
```

Thr

<210> SEQ ID NO 153
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 153

Asp Val Gly Leu Cys Lys Lys Arg Pro Lys Pro Gly Gly Xaa Trp Asn
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 154

Asp Val Gly Leu Cys Lys Lys Arg Pro Lys Pro Gly Gly Xaa Trp
1               5                   10                  15

<210> SEQ ID NO 155
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 14
<223> OTHER INFORMATION: Xaa = Any Amino Acid

<400> SEQUENCE: 155

Asp Val Gly Leu Cys Lys Lys Arg Pro Lys Pro Gly Gly Xaa
1               5                   10

<210> SEQ ID NO 156
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 156

Val Gly Leu Cys Lys Lys Arg Pro Lys Pro Gly Gly Xaa Trp Asn Thr
1               5                   10                  15

Gly

<210> SEQ ID NO 157
<211> LENGTH: 16
<212> TYPE: PRT
<213> ORGANISM: Artificial Sequence
<220> FEATURE:
<223> OTHER INFORMATION: Synthetically generated peptide

```
<220> FEATURE:
<221> NAME/KEY: VARIANT
<222> LOCATION: 13
<223> OTHER INFORMATION: Xaa = Any Amino Acid

<400> SEQUENCE: 157

Val Gly Leu Cys Lys Lys Arg Pro Lys Pro Gly Gly Xaa Trp Asn Thr
 1               5                  10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 158

Val Gly Leu Cys Lys Lys Arg Pro Lys Pro Gly Gly Xaa Trp Asn
 1               5                  10                  15

<210> SEQ ID NO 159
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 159

Val Gly Leu Cys Lys Lys Arg Pro Lys Pro Gly Gly Xaa Trp
 1               5                  10

<210> SEQ ID NO 160
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 13
<223> OTHER INFORMATION: Xaa = Any Amino Acid

<400> SEQUENCE: 160

Val Gly Leu Cys Lys Lys Arg Pro Lys Pro Gly Gly Xaa
 1               5                  10

<210> SEQ ID NO 161
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 161

Thr His Ser Gln Trp Asn Lys Pro Ser Lys Pro Lys Thr Asn Met Lys
 1               5                  10                  15

His Met

<210> SEQ ID NO 162
<211> LENGTH: 17
```

```
<212> TYPE: PRT
<213> ORGANISM: Artificial Sequence
<220> FEATURE:
<223> OTHER INFORMATION: Synthetically generated peptide

<400> SEQUENCE: 162

Thr His Ser Gln Trp Asn Lys Pro Ser Lys Pro Lys Thr Asn Met Lys
1               5                   10                  15
His

<210> SEQ ID NO 163
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 163

Thr His Ser Gln Trp Asn Lys Pro Ser Lys Pro Lys Thr Asn Met Lys
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 164

Thr His Ser Gln Trp Asn Lys Pro Ser Lys Pro Lys Thr Asn Met
1               5                   10                  15

<210> SEQ ID NO 165
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 165

Thr His Ser Gln Trp Asn Lys Pro Ser Lys Pro Lys Thr Asn
1               5                   10

<210> SEQ ID NO 166
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 166

His Ser Gln Trp Asn Lys Pro Ser Lys Pro Lys Thr Asn Met Lys His
1               5                   10                  15
Met

<210> SEQ ID NO 167
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 167

His Ser Gln Trp Asn Lys Pro Ser Lys Pro Lys Thr Asn Met Lys His
1               5                   10                  15
```

<210> SEQ ID NO 168
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 168

His Ser Gln Trp Asn Lys Pro Ser Lys Pro Lys Thr Asn Met Lys
1               5                   10                  15

<210> SEQ ID NO 169
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 169

His Ser Gln Trp Asn Lys Pro Ser Lys Pro Lys Thr Asn Met
1               5                   10

<210> SEQ ID NO 170
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 170

His Ser Gln Trp Asn Lys Pro Ser Lys Pro Lys Thr Asn
1               5                   10

<210> SEQ ID NO 171
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 171

Ser Gln Trp Asn Lys Pro Ser Lys Pro Lys Thr Asn Met Lys His Met
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 172

Ser Gln Trp Asn Lys Pro Ser Lys Pro Lys Thr Asn Met Lys His
1               5                   10                  15

<210> SEQ ID NO 173
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 173

Ser Gln Trp Asn Lys Pro Ser Lys Pro Lys Thr Asn Met Lys
1               5                   10

<210> SEQ ID NO 174
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 174

Ser Gln Trp Asn Lys Pro Ser Lys Pro Lys Thr Asn Met
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 175

Ser Gln Trp Asn Lys Pro Ser Lys Pro Lys Thr Asn
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 176

Gln Trp Asn Lys Pro Ser Lys Pro Lys Thr Asn Met Lys His Met
1               5                   10                  15

<210> SEQ ID NO 177
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 177

Gln Trp Asn Lys Pro Ser Lys Pro Lys Thr Asn Met Lys His
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 178

Gln Trp Asn Lys Pro Ser Lys Pro Lys Thr Asn Met Lys
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 179

Gln Trp Asn Lys Pro Ser Lys Pro Lys Thr Asn Met
1               5                   10

<210> SEQ ID NO 180

```
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 180

Thr His Ser Gln Trp Asn Lys Pro Ser Lys Pro Lys Thr Asn Met Lys
 1               5                  10                  15

His Val

<210> SEQ ID NO 181
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 181

His Ser Gln Trp Asn Lys Pro Ser Lys Pro Lys Thr Asn Met Lys His
 1               5                  10                  15

Val

<210> SEQ ID NO 182
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 182

Ser Gln Trp Asn Lys Pro Ser Lys Pro Lys Thr Asn Met Lys His Val
 1               5                  10                  15

<210> SEQ ID NO 183
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 183

Gln Trp Asn Lys Pro Ser Lys Pro Lys Thr Asn Met Lys His Val
 1               5                  10                  15

<210> SEQ ID NO 184
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 184

Thr His Gly Gln Trp Asn Lys Pro Ser Lys Pro Lys Thr Asn Met Lys
 1               5                  10                  15

His Met

<210> SEQ ID NO 185
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 185
```

```
Thr His Gly Gln Trp Asn Lys Pro Ser Lys Pro Lys Thr Asn Met Lys
1               5                   10                  15

His

<210> SEQ ID NO 186
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 186

Thr His Gly Gln Trp Asn Lys Pro Ser Lys Pro Lys Thr Asn Met Lys
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 187

Thr His Gly Gln Trp Asn Lys Pro Ser Lys Pro Lys Thr Asn Met
1               5                   10                  15

<210> SEQ ID NO 188
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 188

Thr His Gly Gln Trp Asn Lys Pro Ser Lys Pro Lys Thr Asn
1               5                   10

<210> SEQ ID NO 189
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 189

His Gly Gln Trp Asn Lys Pro Ser Lys Pro Lys Thr Asn Met Lys His
1               5                   10                  15

Met

<210> SEQ ID NO 190
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 190

His Gly Gln Trp Asn Lys Pro Ser Lys Pro Lys Thr Asn Met Lys His
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Synthetically generated peptide
```

```
<400> SEQUENCE: 191

His Gly Gln Trp Asn Lys Pro Ser Lys Pro Lys Thr Asn Met Lys
1               5                   10                  15

<210> SEQ ID NO 192
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 192

His Gly Gln Trp Asn Lys Pro Ser Lys Pro Lys Thr Asn Met
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 193

His Gly Gln Trp Asn Lys Pro Ser Lys Pro Lys Thr Asn
1               5                   10

<210> SEQ ID NO 194
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 194

Gly Gln Trp Asn Lys Pro Ser Lys Pro Lys Thr Asn Met Lys His Met
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 195

Gly Gln Trp Asn Lys Pro Ser Lys Pro Lys Thr Asn Met Lys His
1               5                   10                  15

<210> SEQ ID NO 196
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 196

Gly Gln Trp Asn Lys Pro Ser Lys Pro Lys Thr Asn Met Lys
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Synthetically generated peptide
```

-continued

<400> SEQUENCE: 197

Gly Gln Trp Asn Lys Pro Ser Lys Pro Lys Thr Asn Met
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 198

Gly Gln Trp Asn Lys Pro Ser Lys Pro Lys Thr Asn
1               5                   10

<210> SEQ ID NO 199
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 199

Thr His Gly Gln Trp Asn Lys Pro Ser Lys Pro Lys Thr Asn Met Lys
1               5                   10                  15

His Val

<210> SEQ ID NO 200
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 200

His Gly Gln Trp Asn Lys Pro Ser Lys Pro Lys Thr Asn Met Lys His
1               5                   10                  15

Val

<210> SEQ ID NO 201
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 201

Gly Gln Trp Asn Lys Pro Ser Lys Pro Lys Thr Asn Met Lys His Val
1               5                   10                  15

<210> SEQ ID NO 202
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 202

Thr His Asn Gln Trp Asn Lys Pro Ser Lys Pro Lys Thr Asn Met Lys
1               5                   10                  15

His Met

<210> SEQ ID NO 203
<211> LENGTH: 17

```
<212> TYPE: PRT
<213> ORGANISM: Artificial Sequence
<220> FEATURE:
<223> OTHER INFORMATION: Synthetically generated peptide

<400> SEQUENCE: 203

Thr His Asn Gln Trp Asn Lys Pro Ser Lys Pro Lys Thr Asn Met Lys
1               5                   10                  15
His

<210> SEQ ID NO 204
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 204

Thr His Asn Gln Trp Asn Lys Pro Ser Lys Pro Lys Thr Asn Met Lys
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 205

Thr His Asn Gln Trp Asn Lys Pro Ser Lys Pro Lys Thr Asn Met
1               5                   10                  15

<210> SEQ ID NO 206
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 206

Thr His Asn Gln Trp Asn Lys Pro Ser Lys Pro Lys Thr Asn
1               5                   10

<210> SEQ ID NO 207
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 207

His Asn Gln Trp Asn Lys Pro Ser Lys Pro Lys Thr Asn Met Lys His
1               5                   10                  15
Met

<210> SEQ ID NO 208
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 208

His Asn Gln Trp Asn Lys Pro Ser Lys Pro Lys Thr Asn Met Lys His
1               5                   10                  15
```

<210> SEQ ID NO 209
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 209

His Asn Gln Trp Asn Lys Pro Ser Lys Pro Lys Thr Asn Met Lys
1               5                   10                  15

<210> SEQ ID NO 210
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 210

His Asn Gln Trp Asn Lys Pro Ser Lys Pro Lys Thr Asn Met
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 211

His Asn Gln Trp Asn Lys Pro Ser Lys Pro Lys Thr Asn
1               5                   10

<210> SEQ ID NO 212
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 212

Asn Gln Trp Asn Lys Pro Ser Lys Pro Lys Thr Asn Met Lys His Met
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 213

Asn Gln Trp Asn Lys Pro Ser Lys Pro Lys Thr Asn Met Lys His
1               5                   10                  15

<210> SEQ ID NO 214
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 214

Asn Gln Trp Asn Lys Pro Ser Lys Pro Lys Thr Asn Met Lys
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 215

Asn Gln Trp Asn Lys Pro Ser Lys Pro Lys Thr Asn Met
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 216

Asn Gln Trp Asn Lys Pro Ser Lys Pro Lys Thr Asn
1               5                   10

<210> SEQ ID NO 217
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 217

Thr His Asn Gln Trp Asn Lys Pro Ser Lys Pro Lys Thr Asn Met Lys
1               5                   10                  15

His Val

<210> SEQ ID NO 218
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 218

His Asn Gln Trp Asn Lys Pro Ser Lys Pro Lys Thr Asn Met Lys His
1               5                   10                  15

Val

<210> SEQ ID NO 219
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 219

Asn Gln Trp Asn Lys Pro Ser Lys Pro Lys Thr Asn Met Lys His Val
1               5                   10                  15

<210> SEQ ID NO 220
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 220

Pro His Gly Gly Gly Trp Gly Gln Pro His Gly Gly Gly Trp Gly Gln

```
                1               5                   10                  15
Pro His Gly Gly Gly Trp Gly Gln
                20
```

<210> SEQ ID NO 221
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 221

```
Gly Gly Trp Gly Gln Gly Gly Gly Thr His Ser Gln Trp Asn Lys Pro
 1               5                   10                  15
Ser Lys Pro Lys Thr Asn Met Lys His Met
                20                  25
```

<210> SEQ ID NO 222
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 222

```
Gln Trp Asn Lys Pro Ser Lys Pro Lys Thr Asn Met Lys His Met Gly
 1               5                   10                  15
Gly Gly Gln Trp Asn Lys Pro Ser Lys Pro Lys Thr Asn Met Lys His
                20                  25                  30
Met
```

<210> SEQ ID NO 223
<211> LENGTH: 30
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11
<223> OTHER INFORMATION: Xaa = Asn or Ser
<220> FEATURE:
<221> NAME/KEY: VARIANT
<222> LOCATION: 23
<223> OTHER INFORMATION: Xaa = Leu or Met
<220> FEATURE:
<221> NAME/KEY: VARIANT
<222> LOCATION: 26
<223> OTHER INFORMATION: Xaa = Val or Met

<400> SEQUENCE: 223

```
Gly Gly Trp Gly Gln Gly Gly Gly Thr His Xaa Gln Trp Asn Lys Pro
 1               5                   10                  15
Ser Lys Pro Lys Thr Asn Xaa Lys His Xaa Gly Gly Gly Gly
                20                  25                  30
```

<210> SEQ ID NO 224
<211> LENGTH: 23
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 11, 20
<223> OTHER INFORMATION: Xaa = Gly or Ser

```
<400> SEQUENCE: 224

Pro His Gly Gly Gly Trp Gly Gln His Gly Xaa Ser Trp Gly Gln Pro
 1               5                  10                  15

His Gly Gly Xaa Trp Gly Gln
            20

<210> SEQ ID NO 225
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 12
<223> OTHER INFORMATION: Xaa = Leu or Met
<220> FEATURE:
<221> NAME/KEY: VARIANT
<222> LOCATION: 15
<223> OTHER INFORMATION: Xaa = Val or Met

<400> SEQUENCE: 225

Gln Trp Asn Lys Pro Ser Lys Pro Lys Thr Asn Xaa Lys His Xaa Gly
 1               5                  10                  15

Gly Gly

<210> SEQ ID NO 226
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 226

Gly Gly Gly Ala Trp Asn Lys Pro Ser Lys Pro Lys Thr Asn
 1               5                  10

<210> SEQ ID NO 227
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 227

Gly Gly Gly Gln Trp Asn Lys Pro Ser Lys Pro Lys Thr Asn Gly Gly
 1               5                  10                  15

Gly

<210> SEQ ID NO 228
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 228

Gly Gly Gly Lys Lys Arg Pro Lys Pro Gly Gly Trp Asn Thr Gly Gly
 1               5                  10                  15

Gly

<210> SEQ ID NO 229
<211> LENGTH: 5
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: VARIANT
<222> LOCATION: 1, 2, 3, 4, 5
<223> OTHER INFORMATION: Xaa = N-(4-aminobutyl)glycine

<400> SEQUENCE: 229

Xaa Xaa Xaa Xaa Xaa
 1               5

<210> SEQ ID NO 230
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2, 5
<223> OTHER INFORMATION: Xaa = N-(4-aminobutyl)glycine
<220> FEATURE:
<221> NAME/KEY: VARIANT
<222> LOCATION: 3
<223> OTHER INFORMATION: Xaa = N-(4-guanidinobutyl)glycine
<220> FEATURE:
<221> NAME/KEY: VARIANT
<222> LOCATION: 4, 6
<223> OTHER INFORMATION: Xaa = (S)-N-(1-phenylethyl)glycine

<400> SEQUENCE: 230

Xaa Xaa Xaa Xaa Xaa Xaa
 1               5

<210> SEQ ID NO 231
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 4, 7
<223> OTHER INFORMATION: Xaa = N-(4-aminoethyl)glycine
<220> FEATURE:
<221> NAME/KEY: VARIANT
<222> LOCATION: 2, 3, 5, 6, 8, 9
<223> OTHER INFORMATION: Xaa = N-(2-(4-methoxyphenyl)ethyl)glycine

<400> SEQUENCE: 231

Xaa Xaa Xaa Xaa Xaa Xaa Xaa Xaa Xaa
 1               5

<210> SEQ ID NO 232
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 10
<223> OTHER INFORMATION: Xaa = N-(2-methoxyethyl)glycine
<220> FEATURE:
<221> NAME/KEY: VARIANT
<222> LOCATION: 2
<223> OTHER INFORMATION: Xaa = N-(2-3'-indolylethyl)glycine
<220> FEATURE:
<221> NAME/KEY: VARIANT
<222> LOCATION: 4, 7
<223> OTHER INFORMATION: Xaa = N-(4-aminobutyl)glycine
<220> FEATURE:
<221> NAME/KEY: VARIANT
```

```
<222> LOCATION: 5, 8
<223> OTHER INFORMATION: Xaa = (S)-N-(1-phenylethyl)glycine
<220> FEATURE:
<221> NAME/KEY: VARIANT
<222> LOCATION: 6, 9
<223> OTHER INFORMATION: Xaa = N-(2-hydroxyethyl)glycine

<400> SEQUENCE: 232

Xaa Xaa Xaa Xaa Xaa Xaa Xaa Xaa Xaa Xaa
 1               5                  10

<210> SEQ ID NO 233
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 5, 6, 8, 10, 11
<223> OTHER INFORMATION: Xaa = (S)-N-(1-phenylethyl)glycine
<220> FEATURE:
<221> NAME/KEY: VARIANT
<222> LOCATION: 2, 4, 7, 9
<223> OTHER INFORMATION: Xaa = N-(4-aminobutyl)glycine

<400> SEQUENCE: 233

Xaa Xaa Xaa Xaa Xaa Xaa Xaa Xaa Xaa Xaa Xaa
 1               5                  10

<210> SEQ ID NO 234
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 5, 6, 8, 10, 11
<223> OTHER INFORMATION: Xaa = N-benzylglycine
<220> FEATURE:
<221> NAME/KEY: VARIANT
<222> LOCATION: 2, 4, 7, 9
<223> OTHER INFORMATION: Xaa = N-(4-aminobutyl)glycine

<400> SEQUENCE: 234

Xaa Xaa Xaa Xaa Xaa Xaa Xaa Xaa Xaa Xaa Xaa
 1               5                  10

<210> SEQ ID NO 235
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 6, 10, 11
<223> OTHER INFORMATION: Xaa = N-(2-methoxyethyl)glycine
<220> FEATURE:
<221> NAME/KEY: VARIANT
<222> LOCATION: 2, 4, 7, 9
<223> OTHER INFORMATION: Xaa = N-(4-aminobutyl)glycine
<220> FEATURE:
<221> NAME/KEY: VARIANT
<222> LOCATION: 5, 8
<223> OTHER INFORMATION: Xaa = N-((8'-naphthyl)methyl)glycine

<400> SEQUENCE: 235

Xaa Xaa Xaa Xaa Xaa Xaa Xaa Xaa Xaa Xaa Xaa
 1               5                  10
```

```
<210> SEQ ID NO 236
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 5, 6, 8, 10, 11
<223> OTHER INFORMATION: Xaa = N-(2-methoxyethyl)glycine
<220> FEATURE:
<221> NAME/KEY: VARIANT
<222> LOCATION: 2, 4, 7, 9
<223> OTHER INFORMATION: Xaa = N-(4-aminobutyl)glycine

<400> SEQUENCE: 236

Xaa Xaa Xaa Xaa Xaa Xaa Xaa Xaa Xaa Xaa Xaa
 1               5                  10

<210> SEQ ID NO 237
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2, 3, 5
<223> OTHER INFORMATION: Xaa = N-(4-aminobutyl)glycine
<220> FEATURE:
<221> NAME/KEY: VARIANT
<222> LOCATION: 4, 6
<223> OTHER INFORMATION: Xaa = (S)-N-(1-phenylethyl)glycine

<400> SEQUENCE: 237

Xaa Xaa Xaa Xaa Xaa Xaa
 1               5

<210> SEQ ID NO 238
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 4, 6
<223> OTHER INFORMATION: Xaa = N-(4-aminobutyl)glycine
<220> FEATURE:
<221> NAME/KEY: VARIANT
<222> LOCATION: 2, 5
<223> OTHER INFORMATION: Xaa = (S)-N-(1-phenylethyl)glycine

<400> SEQUENCE: 238

Xaa Xaa Xaa Xaa Xaa Xaa
 1               5

<210> SEQ ID NO 239
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2, 3, 5
<223> OTHER INFORMATION: Xaa = N-(4-aminobutyl)glycine
<220> FEATURE:
<221> NAME/KEY: VARIANT
<222> LOCATION: 4, 6
<223> OTHER INFORMATION: Xaa = (S)-N-(1-phenylethyl)glycine
```

```
<400> SEQUENCE: 239

Xaa Xaa Xaa Xaa Xaa Xaa
1               5

<210> SEQ ID NO 240
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2, 3, 5
<223> OTHER INFORMATION: Xaa = N-(4-aminobutyl)glycine
<220> FEATURE:
<221> NAME/KEY: VARIANT
<222> LOCATION: 4, 6
<223> OTHER INFORMATION: Xaa = N-benzylglycine

<400> SEQUENCE: 240

Xaa Xaa Xaa Xaa Xaa Xaa
1               5

<210> SEQ ID NO 241
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3, 5
<223> OTHER INFORMATION: Xaa = N-(2-methoxyethyl)glycine
<220> FEATURE:
<221> NAME/KEY: VARIANT
<222> LOCATION: 2, 4, 6
<223> OTHER INFORMATION: Xaa = N-benzylglycine

<400> SEQUENCE: 241

Xaa Xaa Xaa Xaa Xaa Xaa
1               5
```